(12) United States Patent
Ries et al.

(10) Patent No.: US 6,200,976 B1
(45) Date of Patent: Mar. 13, 2001

(54) ANTITHROMBOTIC QUINOXAZOLINES

(75) Inventors: Uwe Ries, Biberach; Norbert Hauel, Schemmerhofen; Henning Priepke, Warthausen; Herbert Nar, Mittelbiberach; Jean Marie Stassen, Warthausen; Wolfgang Wienen, Biberach, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/280,248

(22) Filed: Mar. 29, 1999

Related U.S. Application Data
(60) Provisional application No. 60/088,175, filed on Jun. 5, 1998.

(30) Foreign Application Priority Data

Jan. 11, 1999 (DE) ............................................... 198 16 983

(51) Int. Cl.[7] ........................ A61K 31/498; C07D 403/08
(52) U.S. Cl. ............................ 514/249; 544/353; 544/354

(58) Field of Search .............................. 514/249; 544/354, 544/353

(56) References Cited

FOREIGN PATENT DOCUMENTS

| 3-210368 | * 9/1991 | (JP) . |
| WO97 21437 | 6/1997 | (WO) . |
| WO99 00371 | 1/1999 | (WO) . |

* cited by examiner

Primary Examiner—Richard L. Raymond
(74) Attorney, Agent, or Firm—Robert P. Raymond; Alan R. Stempel; Mary-Ellen M. Devlin

(57) ABSTRACT

Quinoxazolines having antithrombotic activity. Exemplary of those disclosed are:

4-{[6-(N-carboxymethyl-quinolin-8-yl-sulphonylamino)-1-methyl-2-oxo-1,2-dihydroquinoxalin-3-yl]-methyl}-benzamidine, 4-{[6-(1-(N-cyclopentyl-carboxymethylcarbonylamino)-cyclo-propyl)-1-methyl-2-oxo-1,2-dihydroquinoxalin-3-yl]-methyl}-benzamidine, and 4-{[7-(N-carboxymethylaminocarbonyl-ethylamino)-4-methyl-quinolin-2-yl]-oxo}-benzamidine.

11 Claims, No Drawings

ANTITHROMBOTIC QUINOXAZOLINES

RELATED APPLICATIONS

The benefit of prior provisional application Serial No. 60/088,175, filed on Jun. 5, 1998, is hereby claimed.

DESCRIPTION OF THE INVENTION

The present invention relates to bicyclic compounds of general formula

$$R_a—Het—A—Ar—R_b, \quad (I)$$

their tautomers, stereoisomers, mixtures thereof and the salts thereof, particularly the physiologically acceptable salts thereof with inorganic or organic acids or bases, which have valuable properties.

The compounds of the above general formula I, wherein $R_b$ denotes a cyano group, are useful intermediates for preparing the other compounds of general formula I, and the compounds of the above general formula I, wherein $R_b$ denotes one of the following amidino groups, and the tautomers and stereoisomers thereof, have valuable pharmacological properties, particularly an antithrombotic activity.

The present application thus relates to the new compounds of the above general formula I and the preparation thereof, pharmaceutical compositions containing the pharmacologically actve compounds and their use.

In the above general formula

A denotes an oxygen or sulphur atom, a difluoromethylene, carbonyl, sulphinyl or sulphonyl group, an imino group optionally substituted by a $C_{1-3}$-alkyl group, a methylene group optionally mono- or disubstituted by a carboxy-$C_{1-3}$-alkyl group, Ar denotes a phenylene or naphthylene group optionally substituted by a fluorine, chlorine or bromine atom, by a trifluoromethyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon structure by a $C_{1-3}$-alkyl group, Het denotes a 1-($C_{1-3}$-alkyl)-2-oxo-1,2-dihydro-thieno[2,3-b]-pyrazinyl group, a quinolinylene, isoquinolinylene, quinazolinylene, phthalazinylene, cinnolinylene or quinoxazolinylene ring, which may be substituted in the aromatic heterocyclic moiety by a $C_{1-3}$-alkyl, amino, $C_{1-3}$-alkylamino or di-($C_{1-3}$-alkyl)amino group, a quinolinylene, isoquinolinylene, quinazolinylene or quinoxazolinylene ring, which are di- or tetrahydrogenated in the heterocyclic moiety, whilst in one of the abovementioned dihydrogenated rings, which may additionally be substituted by a $C_{1-3}$-alkyl group, a methylene group adjacent to a nitrogen atom is replaced by a carbonyl or thiocarbonyl group, or in one of the abovementioned tetrahydrogenated rings, which may additionally be substituted by one or two $C_{1-3}$-alkyl groups, two methylene groups adjacent to a nitrogen atom are each replaced by a carbonyl group, and the phenyl moiety of the abovementioned bicyclic rings, wherein additionally a methine group may be replaced by a nitrogen atom, is linked to the group $R_a$, $R_a$ denotes a hydrogen, fluorine, chlorine or bromine atom, a $C_{1-3}$-alkyl, $C_{1-3}$-alkoxy, $C_{2-3}$-alkenyl or $C_{2-3}$-alkynyl group, which may be substituted by a hydroxymethyl or carboxy group, a $C_{1-3}$-alkyl group, which is substituted by a $C_{1-3}$-alkanoylamino or carboxy-$C_{1-3}$-alkylcarbonylamino group, a $R_1$—CO—$CH_2$ group which may be substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, carboxy-$C_{1-3}$-alkylaminocarbonyl or di-($C_{1-3}$-alkyl)-amino-n-$C_{2-4}$-alkyl group and a phenyl group may additionally be fused to the abovementioned pyrrolidino and piperidino moieties via two adjacent carbon atoms, a phenyl, naphthyl or monocyclic 5 or 6 membered heteroaryl group optionally substituted by a $C_{1-3}$-alkyl group, whereby a 6 membered heteroaryl group contains one, two or three nitrogen atoms and a 5 membered heteroaryl group contains an imino group optionally substituted by a $C_{1-3}$-alkyl group, an oxygen or sulphur atom group or an imino group optionally substituted by a $C_{1-3}$-alkyl group and an oxygen or sulphur atom or one or two nitrogen atoms and the before mentioned alkyl substituent may be substituted by a carboxy, carboxy-$C_{1-3}$-alkoxy, carboxy-$C_{1-3}$-alkylamino or N—($C_{1-3}$-alkyl)-carboxy-$C_{1-3}$-alkylamino group, a $C_{1-4}$-alkyl group which is substituted by one or two carboxy groups, a $C_{1-4}$-alkyl group which is substituted
by a $C_{1-3}$-alkyl-$Y_1$-$C_{1-3}$-alkyl, HOOC—$C_{1-3}$-alkyl-$Y_1$-$C_{1-3}$-alkyl, tetrazoly-$C_{1-3}$-alkyl-$Y_2$—, $R_2NR_3$— or $R_2NR_3$—$C_{1-3}$-alkyl group and by a carboxy, aminocarbonyl, $C_{1-3}$-alkylaminocarbonyl, di-($C_{1-3}$-alkyl)-aminocarbonyl or $C_{5-7}$-cycloalkyleniminocarbonyl group, whereby the $C_{5-7}$-cycloalkylenimino moiety in the before mentioned groups may be substituted by one or two $C_{1-3}$-alkyl groups and at the same time additionally one alkyl moiety or alkyl substituent of the before mentioned $C_{1-3}$-alkylaminocarbonyl, di-($C_{1-3}$-alkyl)-aminocarbonyl or $C_{5-7}$-cycloalkyleniminocarbonyl groups may be substituted by a carboxy group, and the remaining hydrogen atoms of a $C_{1-4}$-alkyl group may be totally or partly replaced by fluorine atoms, wherein $R_2$ denotes a hydrogen atom or a $C_{1-3}$-alkyl group optionally substituted by a carboxy group and $R_3$ denotes a $C_{1-3}$-alkyl-$Y_1$-$C_{1-3}$-alkyl-$Y_2$, carboxy-$C_{1-3}$-alkyl-$Y_1$-$C_{1-3}$-alkyl-$Y_2$, $C_{1-3}$-alkyl-$Y_2$ or carboxy-$C_{1-3}$-alkyl-$Y_2$ group or $R_2$ and $R_3$ together with the attached nitrogen atom denotes a $C_{3-7}$-cycloalkylenimino group optionaylly substituted by a carboxy, $C_{1-3}$-alkyl or carboxy-$C_{1-3}$-alkyl group, wherein $Y_1$ denotes a carbon-carbon bond, an oxygen atom, a sulphenyl, sulphinyl, sulphonyl, —NH—, —NH—CO— or —NH—CO—NH— group and $Y_2$ denotes a carbon-nitrogen bond or a carbonyl, sulphonyl or —NH—CO— group, whereby the carbonyl group of the —NH—CO— group is attached to the nitrogen atom of the $R_2NR_3$ group, and the imino groups mentioned at the definition of the radicals $Y_1$ and $Y_2$ may be additionally substituted by a $C_{1-3}$-alkyl or carboxy-$C_{1-3}$-alkyl group, a nitro group or an amino group optionally substituted by a $C_{1-3}$-alkanoyl or carboxy-$C_{1-4}$-alkyl group, a hydroxyimino-$C_{1-3}$-alkylene group which may be substituted at the oxygen atom by a carboxy-$C_{1-3}$-alkyl group, a $C_{3-7}$-cycloalkyl or $C_{5-6}$-cycloalkenyl group, a phenyl group which may be substituted by a $C_{1-3}$-alkyl, $C_{2-3}$-alkenyl, carboxy, nitro or amino group, whilst the amino group may additionally be substituted by a $C_{1-3}$-alkanoyl, carboxy-$C_{1-3}$-alkyl, carboxy-$C_{1-3}$-alkylcarbonyl or carboxy-$C_{1-3}$-alkylamino-carbonyl group, a phenyl group which is substituted by a $C_{1-3}$-alkyl group and by a carboxy or carboxy-$C_{1-3}$-alkylaminocarbonyl group, a carbonyl group which is substituted by a $C_{1-6}$-alkyl, $C_{5-7}$-cycloalkyl, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl or tetrazolyl-$C_{1-3}$-alkyl group, a carboxy-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, carboxy-$C_{1-3}$-alkylsulphonyl, tetrazolyl-$C_{1-3}$-alkylcarbonyl or carboxy-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl group, which may additionally be substituted by a $C_{1-5}$-alkyl group, a phenylsulphonyl group or a $C_{1-5}$-alkylsulphonyl group wherein the alkyl moiety may be substituted by an amino, $C_{1-3}$-alkylamino or di-($C_{1-3}$-alkyl)-amino group, an imidazolidin-2-on-1-yl group which may be substituted in the 3 position by a carboxy-$C_{1-3}$-alkyl group, a $C_{3-7}$-cycloalkyl group which is substituted in the 1 position by a $C_{4-7}$-cycloalkylamino or $C_{1-4}$-alkylamino group, wherein the hydrogen atom of the amino moiety may be replaced by a carboxy-$C_{1-3}$-alkylcarbonyl group, and $R_b$ denotes a cyano group or an amidino group.

The carboxy groups mentioned above at the definition of the radicals may be replaced by a group convertable in-vivo into a carboxy group or by a group convertable under physiologically conditions into a negatively charged group or the amino or imino groups groups mentioned above at the definition of the radicals may be substituted by a group which can be splitt off in-vivo.

By a group which can be converted in-vivo into a carboxy group is meant, for example, a hydroxymethyl group, a carboxy group esterified with an alcohol wherein the alcoholic moiety is preferably a $C_{1-6}$-alkanol, a phenyl-$C_{1-3}$-alkanol, a $C_{3-9}$-cyclo-alkanol, whereby a $C_{5-8}$-cycloalkanol may be additionally substituted by one or two $C_{1-3}$-alkyl groups, a $C_{5-8}$-cycloalkanol wherein one methylene group in 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may be additionally substituted by one or two $C_{1-3}$-alkyl groups, a $C_{4-7}$-cycloalkenol, $C_{3-5}$-alkenol, phenyl-$C_{3-5}$-alkenol or phenyl-$C_{3-5}$-alkinol group with the proviso that no bond from a carbon atom to an oxygene atom exists to which carbon atom is attached a double or triple bond, a bicycloalkanol containing a total of 8 to 10 carbon atoms which may be additionally subtituted in the bicyloalkyl moiety by one or two $C_{1-3}$-alkyl groups, a 1,3-dihydro-3-oxo-1-isobenzfuranyl group or an alcohol of the formula

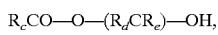

wherein $R_c$ denotes a $C_{1-8}$-alkyl, $C_{5-7}$-cycloalkyl, phenyl or phenyl-$C_{1-3}$-alkyl group, $R_d$ denotes a hydrogen atom, a $C_{1-3}$-alkyl, $C_{5-7}$-cycloalkyl or phenyl group and $R_e$ denotes a hydrogen atom or a $C_{1-3}$-alkyl group, by a group convertable under physiologically conditions into a negatively charged group is meant a group such as a tetrazol-5-yl, phenylcarbonylaminocarbonyl, trifluoromethylcarbonyl-aminocarbonyl, $C_{1-6}$-alkylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved from an imino or amino group in-vivo is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl or $C_{1-3}$-alkoxy-$C_{2-4}$-alkoxycarbonyl group, a steroidal alcohol group bound via a carbonyl group such as the 17-(1,5-dimethyl-hexyl)-10,13-dimethyl-2,3,4,7,8,9,10, 11,12,13,14,15,16,17-tetradecahydro-1H-cyclopenta[a]phenanthren-3-yl]-oxycarbonyl group or a $R_cCO-O-(R_dCR_e)-O-CO$ group wherein $R_c$ to $R_e$ are as hereinbefore defined.

Moreover, the saturated alkyl and alkoxy moieties which contain more than 2 carbon atoms as mentioned above in the definitions also include the branched isomers thereof, such as, for example, the isopropyl, tert.butyl, isobutyl groups, etc.

Preferred compounds of the abovementioned general formula I are those, wherein

A denotes an oxygen or sulphur atom, a difluoromethylene, carbonyl, sulphinyl or sulphonyl group, an imino group optionally substituted by a $C_{1-3}$-alkyl group, a methylene group optionally mono- or disubstituted by a carboxy-$C_{1-3}$-alkyl or $C_{1-3}$-alkoxy-carbonyl-$C_{1-3}$-alkyl group, Ar denotes a phenylene or naphthylene group optionally substituted by a fluorine, chlorine or bromine atom, by a trifluoro-methyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon structure by a $C_{1-3}$-alkyl group, Het denotes a 1-($C_{1-3}$-alkyl)-2-oxo-1,2-dihydro-thieno[2,3-b]-pyrazinyl group, a quinolinylene, isoquinolinylene, quinazolinylene, phthalazinylene, cinnolinylene or quinoxazolinylene ring, which may be substituted in the aromatic heterocyclic moiety by a $C_{1-3}$-alkyl, amino, $C_{1-3}$-alkylamino or di-($C_{1-3}$-alkyl)amino group, a quinolinylene, isoquinolinylene, quinazolinylene or quinoxazolinylene ring, which are di- or tetrahydrogenated in the heterocyclic moiety, whilst in one of the abovementioned dihydrogenated rings, which may additionally be substituted by a $C_{1-3}$-alkyl group, a methylene group adjacent to a nitrogen atom is replaced by a carbonyl or thiocarbonyl group, or in one of the abovementioned tetrahydrogenated rings, which may additionally be substituted by one or two $C_{1-3}$-alkyl groups, two methylene groups adjacent to a nitrogen atom are each replaced by a carbonyl group, and the phenyl moiety of the abovementioned bicyclic rings, wherein additionally a methine group may be replaced by a nitrogen atom, is linked to the group $R_a$, $R_a$ denotes a hydrogen, fluorine, chlorine or bromine atom, a $C_{1-3}$-alkyl, $C_{1-3}$-alkoxy, $C_{2-3}$-alkenyl or $C_{2-3}$-alkynyl group, which may be substituted by a hydroxymethyl, carboxy or $C_{1-3}$-alkoxycarbonyl group, a $C_{1-3}$-alkyl group, which is substituted by a $C_{1-3}$-alkanoylamino, carboxy-$C_{1-3}$-alkylcarbonylamino or $C_{1-3}$-alkoxycarbonyl-$C_{1-3}$-alkyl-carbonylamino group, a $C_{1-4}$-alkyl group which is substituted by one or two carboxy or $C_{1-3}$-alkoxycarbonyl groups or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkyl-amino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a nitro group or an amino group optionally substituted by a $C_{1-3}$-alkanoyl, carboxy-$C_{1-4}$-alkyl or $C_{1-3}$-alkoxycarbonyl-$C_{1-4}$-alkyl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a $C_{3-7}$-cycloalkyl or $C_{5-6}$-cycloalkenyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylcarbonyl, $C_{1-3}$-alkoxycarbonyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkyl-sulphonamido, phenylsulphonylamino, naphthylsulphonylamino, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a phenylsulphonyl group or a $C_{1-3}$-alkylsulphonyl group wherein the alkyl moiety may be substituted by an amino, $C_{1-3}$-alkylamino or di-($C_{1-3}$-alkyl)-amino group, an imidazolidin-2-on-1-yl group which may be substituted in the 3 position by a carboxy-$C_{1-3}$-alkyl or $C_{1-3}$-alkoxycarbonyl-$C_{1-3}$-alkyl group, a $C_{3-5}$-cycloalkyl group which is substituted in the 1 position by a $C_{4-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, a $R_1$—CO—$CH_2$ group which may be substituted in the methylene moiety by one or two $C_{1-3}$-alkyl groups, or a $C_{3-5}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl, $C_{1-3}$-alkoxycarbonyl-$C_{1-3}$-alkylaminocarbonyl or di-($C_{1-3}$-alkyl)-amino-n-$C_{2-4}$-alkyl group and a phenyl group may additionally be fused to the abovementioned pyrrolidino and piperidino moieties via two adjacent carbon atoms, or a pyrazolyl group optionally substituted by a $C_{1-3}$-alkyl group, and $R_b$ denotes a cyano group or an amidino group optionally substituted by a hydroxy, by one or two $C_{1-3}$-alkyl groups or by a $C_{1-16}$-alkoxycarbonyl group, especially those compounds, wherein A denotes an oxygen or sulphur atom, a difluoromethylene, carbonyl, sulphinyl or sulphonyl group, an imino group optionally substituted by a $C_{1-3}$-alkyl group, a methylene group optionally mono- or disubstituted by a carboxy-$C_{1-3}$-alkyl or $C_{1-3}$-alkoxy-carbonyl-$C_{1-3}$-alkyl group, Ar denotes a phenylene or naphthylene group optionally substituted by a fluorine, chlorine or bromine atom, by a trifluoromethyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon structure by a $C_{1-3}$-alkyl group, Het denotes a 1-($C_{1-3}$-alkyl)-2-oxo-1,2-dihydro-thieno[2,3-b]-pyrazinyl group, a quinolinylene, isoquinolinylene, quinazolinylene, phthalazinylene, cinnolinylene or quinoxazolinylene ring, which may be substituted in the aromatic heterocyclic moiety by a $C_{1-3}$-alkyl, amino, $C_{1-3}$-alkylamino or di-($C_{1-3}$-alkyl)amino group, a quinolinylene, isoquinolinylene, quinazolinylene or quinoxazolinylene ring, which are di- or tetrahydrogenated in the heterocyclic moiety, whilst in one of the abovementioned dihydrogenated rings, which may additionally be substituted by a $C_{1-3}$-alkyl group, a methylene group adjacent to a nitrogen atom is replaced by a carbonyl or thiocarbonyl group, or in one of the abovementioned tetrahydrogenated rings, which may additionally be substituted by one or two $C_{1-3}$-alkyl groups, two methylene groups adjacent to a nitrogen atom are each replaced by a carbonyl group, and the phenyl moiety of the abovementioned bicyclic rings, wherein additionally a methine group may be replaced by a nitrogen atom, is linked to the group $R_a$, $R_a$ denotes a hydrogen, fluorine, chlorine or bromine atom, a $C_{1-3}$-alkyl, $C_{2-3}$-alkenyl or $C_{2-3}$-alkynyl group, which may be substituted by a hydroxymethyl, carboxy or $C_{1-3}$-alkoxycarbonyl group, a $C_{1-3}$-alkyl group, which is substituted by a $C_{1-3}$-alkanoylamino, carboxy-$C_{1-3}$-alkylcarbonylamino or $C_{1-3}$-alkoxycarbonyl-$C_{1-3}$-alkyl-carbonylamino group, a $C_{1-3}$-alkyl group which is substituted by one or two carboxy or $C_{1-3}$-alkoxycarbonyl groups or by a pyrrolidinocarbonyl or piperidinocarbonyl group and by a carboxy, $C_{1-3}$-alkoxycarbonyl, carboxy-$C_{1-3}$-alkylcarbonylamino or $C_{1-3}$-alkoxycarbonyl-$C_{1-3}$-alkyl-carbonylamino group, whilst the abovementioned pyrrolidino and piperidino moieties may additionally be substituted by one or two $C_{1-3}$-alkyl groups, a nitro group or an amino group optionally substituted by a $C_{1-3}$-alkanoyl, carboxy-$C_{1-4}$-alkyl or $C_{1-3}$-alkoxycarbonyl-$C_{1-4}$-alkyl group, a hydroxyimino-$C_{1-3}$-alkylene group which may be substituted at the oxygen atom by a carboxy-$C_{1-3}$-alkyl or $C_{1-3}$-alkoxy-carbonyl-$C_{1-3}$-alkyl group, a $C_{3-7}$-cycloalkyl or $C_{5-6}$-cycloalkenyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylcarbonyl, $C_{1-3}$-alkoxycarbonyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkyl-sulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a phenylsulphonyl group or a $C_{1-5}$-alkylsulphonyl group wherein the alkyl moiety may be substituted by an amino, $C_{1-3}$-alkylamino or di-($C_{1-3}$-alkyl)-amino group, an imidazolidin-2-on-1-yl group which may be substituted in the 3 position by a carboxy-$C_{1-3}$-alkyl or $C_{1-3}$-alkoxycarbonyl-$C_{1-3}$-alkyl group, a $C_{3-7}$-cycloalkyl group which is substituted in the 1 position by a $C_{4-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, a $R_1$—CO—$CH_2$ group which is substituted in the methylene moiety by two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl- or $C_{1-3}$-alkoxycarbonyl-$C_{1-3}$-alkyl-aminocarbonyl group and a phenyl group may additionally be fused to the abovementioned pyrrolidino and piperidino moieties via two adjacent carbon atoms, and $R_b$ denotes a cyano group or an amidino group which may be substituted by a hydroxy group, by one or two $C_{1-3}$-alkyl groups or by a $C_{1-16}$-alkoxycarbonyl group, whereby Het denotes preferably a 1,3-dioxo-3,4-dihydro-1H-isoquinolin-2-yl, 1-oxo-1,2-dihydro-1H-isoquinolin-2-yl, quinolin-2-yl, 1,4-dihydro-2H-quinazolin-2,4-dion-3-yl, 4H-quinazolin-4-on-3-yl, 4-oxo-3,4-dihydro-quinazolin-2-yl, 2-oxo-1,2-dihydro-quinoxalin-3-yl, 2-thio-1,2-dihydro-quinoxalin-3-yl, 1,8-naphthyridin-2-yl, 3-oxo-3,4-dihydro-pyrido[2,3-b]pyrazin-2-yl or 2-oxo-1,2-dihydro-pyrido[2,3-b]pyrazin-3-yl-group, the tautomers, stereoisomers and salts thereof.

Particularly preferred compounds of general formula I are those wherein

A denotes an oxygen atom, a methylene or imino group,

Ar denotes a phenylene or naphthylene group optionally substituted by a fluorine, chlorine or bromine atom, by a trifluoromethyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon structure by a $C_{1-3}$-alkyl group, Het denotes a 4,4-di-($C_{1-3}$-alkyl)-1,3-dioxo-3,4-dihydro-1H-isoquinolinyl-2-yl, 4-($C_{1-3}$-alkyl)-1-oxo-1,2-dihydro-1H-isoquinolinyl-2-yl, 4-($C_{1-3}$-alkyl)-quinolinyl-2-yl, 4-amino-quinazolin-2-yl, 4-($C_{1-3}$-alkylamino)-quinazolin-2-yl, 4-[di-($C_{1-3}$-alkyl)-amino]-quinazolin-2-yl, 4-($C_{1-3}$-alkyl)-quinazolin-2-yl, 3-($C_{1-3}$-alkyl)-4H-quinazolin-4-on-2-yl, 3-($C_{1-3}$-alkyl)-4-oxo-3,4-dihydro-quinazolin-2-yl, 1-($C_{1-3}$-alkyl)-2-oxo-1,2-dihydro-quinazolin-3-yl, 1-($C_{1-3}$-alkyl)-2-thio-1,2-dihydro-quinazolin-3-yl-, 1-($C_{1-3}$-alkyl)-1,8-naphthyridin-2-yl, 3-oxo-3,4-dihydro-pyrido[2,3-b]pyrazin-2-yl or 2-oxo-1,2-dihydro-pyrido[2,3-b]pyrazin-3-yl group each attached via the phenyl moiety with the radical $R_a$, $R_a$ denotes a hydrogen, chlorine or bromine atom, a $C_{1-3}$-alkyl, $C_{2-3}$-alkenyl or $C_{2-3}$-alkynyl group, which may be substituted by a hydroxymethyl, carboxy or $C_{1-3}$-alkoxycarbonyl group, a $C_{1-3}$-alkyl group, which is substituted by a $C_{1-3}$-alkanoylamino, carboxy-$C_{1-3}$-alkylcarbonylamino or $C_{1-3}$-alkoxycarbonyl-$C_{1-3}$-alkyl-carbonylamino group, a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkyl-amino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a nitro group or an amino group optionally substituted by a $C_{1-3}$-alkanoyl, carboxy-$C_{1-4}$-alkyl or $C_{1-3}$-alkoxycarbonyl-$C_{1-4}$-alkyl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a $C_{3-7}$-cycloalkyl or $C_{5-6}$-cycloalkenyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylcarbonyl, $C_{1-3}$-alkoxycarbonyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkyl-sulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a piperidino group, wherein a methylene group in the 2 position is replaced by a carbonyl or sulphonyl group, a tetrazolyl group optionally substituted by a $C_{1-3}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-3}$-alkyl group, a phenylsulphonyl group or a $C_{1-5}$-alkylsulphonyl group wherein the alkyl moiety may be substituted by a di-($C_{1-3}$-alkyl)-amino group, an imidazolidin-2-on-1-yl group which may be substituted in the 3 position by a carboxy-$C_{1-3}$-alkyl or $C_{1-3}$-alkoxycarbonyl-$C_{1-3}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, a $R_1$—CO—$CH_2$ group which is substituted in the methylene moiety by one or two $C_{1-3}$-alkyl groups, or a $C_{3-6}$-cycloalkylene group which is substituted in the 1 position tion by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fused to the abovementioned pyrrolidino and piperidino moieties via two adjacent carbon atoms, or a pyrazolyl group optionally substituted by a $C_{1-3}$-alkyl group, and $R_b$ denotes a cyano group or an amidino group optionally substituted by a hydroxy, $C_{1-6}$-alkoxycarbonyl or 17-(1,5-dimethyl-hexyl)-10,13-dimethyl-2,3,4,7,8,9,10,11,12,13,14,15,16,17-tetradecahydro-1H-cyclopenta[a]phe-nanthren-3-yl]-oxy-carbonyl group, the tautomers, stereoisomers and salts thereof.

Most particularly preferred compounds of general formula I are those wherein

A denotes an oxygen atom, a methylene or imino group,

Ar denotes a phenylene group, preferably a 1,4-phenylene group,

Het denotes a 4-($C_{1-3}$-alkyl)-quinolinyl-2-yl or 1-($C_{1-3}$-alkyl)-2-oxo-1,2-dihydro-quinazolin-3-yl group each attached via the phenyl moiety with the radical $R_a$, $R_a$ denotes a hydrogen, chlorine or bromine atom, a $C_{1-3}$-alkyl group which is substituted by a $C_{1-3}$-alkanoylamino, z-carboxy-$C_{1-3}$-alkylcarbonylamino or $C_{1-3}$-alkoxycarbonyl-$C_{1-3}$-alkyl-carbonylamino group, a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkyl-amino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a $R_1$—CO—$CH_2$ group which is substituted in the methylene moiety by one or two $C_{1-3}$-alkyl groups, or a $C_{3-6}$-cycloalkylene group which is substituted in the 1 position tion by an $R_1$—CO group, whilst $R_1$ is a hydroxy, $C_{1-3}$-alkoxy, amino, $C_{1-3}$-alkylamino, pyrrolidino, piperidino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fused to the abovementioned pyrrolidino and piperidino moieties via two adjacent carbon atoms, or a pyrazolyl group optionally substituted by a $C_{1-3}$-alkyl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkyl-aminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, and $R_b$ denotes an amidino group optionally substituted by a hydroxy, $C_{1-16}$-alkoxycarbonyl or 17-(1,5-dimethyl-hexyl)-10,13-dimethyl-2,3,4,7,8,9,10,11,12,13,14,15,16,17-tetradecahydro-1H-cyclopenta[a]phe-nanthren-3-yl]-oxycarbonyl group, particulary the compounds wherein A denotes an oxygen atom, a methylene or imino group, Ar denotes a 1,4-phenylene group, Het denotes a 4-methyl-quinolinyl-2-yl or 1-methyl-2-oxo-1,2-dihydro-quinazolin-3-yl group each attached via the phenyl moiety with the radical $R_a$, $R_a$ denotes a hydrogen atom, a $C_{1-3}$-alkyl group which is substituted by a $C_{1-3}$-alkanoylamino, carboxy-$C_{1-3}$-alkylcarbonylamino or $C_{1-3}$-alkoxycarbonyl-$C_{1-3}$-alkyl-carbonylamino group, a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkyl-amino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two methyl groups, a $R_1$—CO—$CH_2$ group which is substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino or N—($C_{1-3}$-alkyl)- piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fused to the abovementioned pyrrolidino and piperidino moieties via two adjacent carbon atoms, or a 1-($C_{1-3}$-alkyl)-pyrazol-5-yl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl or amino group, whilst the amino group may additionally be substituted by a carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group, a phenyl group which is substituted by a methyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, and $R_b$ denotes an amidino group optionally substituted by a hydroxy, $C_{1-16}$-alkoxycarbonyl or 17-(1,5-dimethyl-hexyl)-10,13-dimethyl-2,3,4,7,8,9,10,11,12,13,14,15,16,17-tetradecahydro-1H-cyclopenta[a]phenanthren-3-yl3-oxycarbonyl group, the tautomers, stereoisomers and salts thereof.

The following are examples of particularly preferred compounds:

(a) 4-{[6-(N-carboxymethyl-quinolin-8-yl-sulphonylamino)-1-methyl-2-oxo-1,2-dihydroquinoxalin-3-yl]-methyl}-benzamidine, (b) 4-{[6-(1-(N-cyclopentyl-carboxymethylcarbonylamino)-cyclo-propyl)-1-methyl-2-oxo-1,2-dihydroquinoxalin-3-yl]-methyl}-benzamidine, (c) 4-{[7-(N-carboxymethylaminocarbonyl-ethylamino)-4-methyl-quinolin-2-yl]-oxo}-benzamidine, (d) 4-{[7-(N-(pyridin-2-yl)-N-(2-carboxyethyl)-aminocarbonyl)-4-methyl-quinolin-2-yl]-oxo}-benzamidine, (e) 4-{[6-(1-methyl-1-(pyrrolidin-1-yl-carbonyl)-ethyl)-1-methyl-2-oxo-1,2-dihydroquinoxalin-3-yl]-methyl}-benzamidine, (f) 4-{[6-(1-(pyrrolidin-1-yl-carbonyl)-cyclopropyl)-1-methyl-2-oxo-1,2-dihydroquinoxalin-3-yl]-methyl}-benzamidine, (g) 4-{[6-(1-(N-methyl-carboxymethylcarbonylaminomethyl)-1-(pyrrolidin-1-yl-carbonyl)-ethyl)-2-oxo-1,2-dihydroquinoxalin-3-yl]-methyl}-benzamidine and the salts thereof.

According to the invention the compounds of general formula I are obtained by known methods, e.g. by the following processes:

a) In order to prepare a compound of general formula I wherein A denotes a methylene group, Het denotes a 1,4-dihydro-2H-quinazolin-2,4-dion-3-yl group and $R_b$ denotes a cyano group:

cyclising a compound of general formula

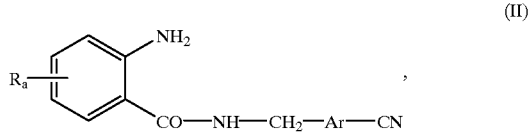

(II)

wherein

Ar and $R_a$ are as hereinbefore defined, in the presence of a carbonic acid diester derivative.

The cyclisation is conveniently carried out in a solvent or mixture of solvents such as glacial acetic acid, benzene, chlorobenzene, toluene, xylene, glycol, glycol monomethyl ether, pyridine, diethyleneglycol dimethyl ether, sulpholane, dimethylformamide or tetralin in the presence of a carbonic acid diester derivative such as phosgene or triphosgene at temperatures between 0 and 250° C., but preferably at the boiling temperature of the reaction mixture.

b) In order to prepare a compound of general formula I wherein A denotes a methylene group, Het denotes a 4-oxo-3,4-dihydroquinazolin-2-yl group and $R_b$ denotes a cyano group:

cyclising a compound of general formula

(III)

wherein

Ar and $R_a$ are as hereinbefore defined and $Z_1$ denotes a leaving group such as a halogen atom, an alkoxy, phenylalkoxy or phenoxy group, e.g. a methoxy or ethoxy group, in the presence of an ammonium salt.

The reaction is preferably carried out in the presence of an ammonium salt such as ammonium chloride and in the presence of a condensing agent such as phosphorus pentoxide and in the presence of a tertiary organic base such as N,N-dimethylcyclohexylamine at elevated temperatures, e.g. at temperatures between 150 and 250° C., preferably at 190° C.

c) In order to prepare a compound of general formula I wherein A denotes a methylene group, Het denotes a 2-oxo-1,2-dihydroquinoxalin-3-yl group and $R_b$ denotes a cyano group:

reacting a diamine of general formula

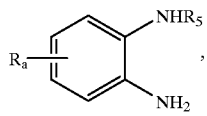
(IV)

wherein $R_a$ is as hereinbefore defined and $R_5$ denotes a hydrogen atom or a $C_{1-3}$-alkyl group, with a ketone of general formula

HOCO—CO—CH$_2$—Ar—CN, (V)

wherein

Ar is as hereinbefore defined, or the reactive derivatives thereof.

The reaction is preferably carried out with a reactive derivative of the ketone of formula V such as the ethyl or phenylester, conveniently in a solvent such as ethanol at elevated temperatures, e.g. at the boiling temperature of the solvent used.

d) In order to prepare a compound of general formula I wherein A denotes a methylene group, Het denotes a 4-oxo-3,4-dihydroquinazolin-2-yl group and $R_b$ denotes a cyano group:

cyclising a compound of general formula

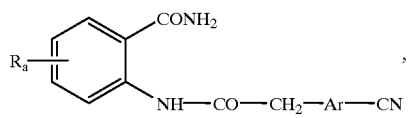
(VI)

wherein

Ar and $R_a$ are as hereinbefore defined, in the presence of a basic condensing agent.

The cyclisation is carried out in the presence of a basic condensing agent such as an alkoxide, e.g. sodium ethoxide, preferably in a solvent such as ethanol at elevated temperatures, preferably at the boiling temperature of the solvent used.

e) In order to prepare a compound of general formula I wherein Het is linked to A via a nitrogen atom and A denotes a methylene group and $R_b$ denotes a cyano group:

reacting a compound of general formula

$R_a$—Het—H, (VII)

wherein $R_a$ is as hereinbefore defined and

Het contains a hydrogen atom bound to a cyclic nitrogen atom, with a compound of general formula

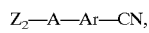
Z$_2$—A—Ar—CN, (VIII)

wherein

A and Ar are as hereinbefore defined and

Z$_2$ denotes a leaving group such as a halogen atom, e.g. a chlorine, bromine or iodine atom.

The reaction is conveniently carried out in a solvent or mixture of solvents such as water, methylene chloride, chloroform, ether, tetrahydrofuran, dioxan or dimethylformamide optionally in the presence of an inorganic or organic base, such as sodium hydroxide, potassium carbonate, triethylamine or pyridine, whilst the last two may simultaneously act as solvent, at temperatures between −25 and 100° C., but preferably at temperatures between −10 and 80° C.

f) In order to prepare a compound of general formula I wherein Het is linked to A via a $C_{1-3}$-alkylimino group, an oxygen, sulphur or nitrogen atom and A denotes a methylene group and $R_b$ denotes a cyano group:

reacting a compound of general formula

$R_a$—Het—Z$_3$, (IX)

wherein $R_a$ and Het are as hereinbefore defined, with the proviso that

Z$_3$ is linked to a carbon atom of the Het group and denotes a leaving group such as a halogen atom, e.g. a chlorine, bromine or iodine atom, with a compound of general formula

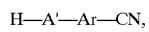
H—A'—Ar—CN, (X)

wherein

Ar is as hereinbefore defined and

A' denotes an imino or $C_{1-3}$-alkylimino group, an oxygen or sulphur atom.

The reaction is conveniently carried out in a solvent or mixture of solvents such as water, methylene chloride, chloroform, ether, tetrahydrofuran, dioxan or dimethylformamide optionally in the presence of an inorganic or organic base, such as sodium hydroxide, potassium carbonate, triethylamine or pyridine, whilst the last two may simultaneously act as solvent, at temperatures between −25 and 100° C., but preferably at temperatures between −10 and 80° C.

g) In order to prepare a compound of general formula I wherein $R_a$ denotes one of the optionally substituted —CONH— and —SO$_2$NH— groups mentioned for $R_a$ hereinbefore which is linked to the Het group either via the nitrogen atom or via the carbonyl or sulphonyl group:

reacting a compound of general formula

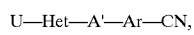
U—Het—A'—Ar—CN, (XI)

with a compound of general formula

V—$R_a$', (XII)

wherein

A, Ar and Het are as hereinbefore defined, one of the groups U or V denotes an HOCO— or HOSO$_2$— group or the reactive derivatives thereof and the other one of the groups U or V denotes one of the optionally substituted amino groups mentioned for $R_a$ hereinbefore, which is linked to the Het group either via the nitrogen atom or via the carbonyl or sulphonyl group.

The reaction of an acid with an amine is optionally carried out in a solvent or mixture of solvents such as methylene chloride, dimethylformamide, benzene, toluene, chlorobenzene, tetrahydrofuran, benzene/tetrahydrofuran or dioxan or in an excess of the amine used conveniently in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C.

The reaction of a corresponding reactive compound of general formula X or XI such as the esters, imidazolides or halides thereof with a corresponding amine is preferably carried out in a corresponding amine as the solvent, optionally in the presence of another solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

h) In order to prepare a compound of general formula I wherein $R_a$ denotes one of the optionally substituted phenyl and alkenyl groups mentioned for $R_a$ hereinbefore and $R_b$ denotes a cyano group:

reacting a compound of general formula

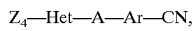
Z₄—Het—A—Ar—CN, (XIII)

wherein

Ar and Het are as hereinbefore defined and $Z_4$ denotes a trifluoromethanesulphonyloxy group, a bromine or iodine atom, with a compound of general formula

R₆—Z₅, (XIV)

wherein $R_6$ denotes on of the optionally substituted phenyl and alkenyl groups mentioned for $R_a$ hereinbefore and $Z_5$ denotes a boric acid group or a tri-($C_{1-4}$-alkyl)-tin group.

The reaction is preferably carried out in a solvent such as toluene/water, dimethoxyethane or dimethylformamide in the presence of a metal catalyst such as bis(triphenylphosphine)-palladium-(II)chloride or tetrakis-(triphenylphosphine)-palladium (0) in the presence of a base such as sodium carbonate or caesium carbonate at temperatures between 20 and 100° C., preferably at temperatures between 40 and 80° C.

i) In order to prepare a compound of general formula I wherein $R_b$ denotes an amidino group, which may be substituted by a hydroxy group, by one or two $C_{1-3}$-alkyl groups:

reacting a compound of general formula

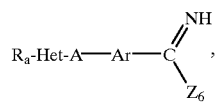

(XV)

optionally formed in the reaction mixture wherein

A, Ar, Het and $R_a$ are as hereinbefore defined and $Z_6$ denotes an alkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula

R₆NH—R₇, (XVI)

wherein $R_6$ denotes a hydrogen atom, a $C_{1-3}$-alkyl or a hydroxy group and $R_7$ denotes a hydrogen atom or a $C_{1-3}$-alkyl group.

The reaction is conveniently carried out in a solvent such as methanol, ethanol, n-propanol, water, methanol/water, tetrahydrofuran or dioxan at temperatures between 0 and 150° C., preferably at temperatures between 20 and 120° C., with a compound of general formula XVI or with a corresponding acid addition salt such as for example ammonium carbonate.

A compound of general formula XV is obtained for example by reacting a corresponding cyano compound of general formula I with a corresponding alcohol such as methanol, ethanol, n-propanol, isopropanol or benzyl alcohol in the presence of an acid such as hydrochloric acid at temperatures between 0 and 500° C., but preferably at 20° C., or a corresponding nitrile with hydrogen sulphide, conveniently in a solvent such as pyridine or dimethylformamide and in the presence of a base such as triethylamine and subsequent alkylation of the thioamide formed with a corresponding alkyl or aralkylhalide.

A hydroxyamidino compound thus obtained may subsequently, if desired, be converted into the corresponding amidino compound by means of reduction, preferably by means of catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar.

j) In order to prepare a compound of general formula I wherein $R_b$ denotes an amidino group substituted by a prodrug group:

reacting a compound of general formula

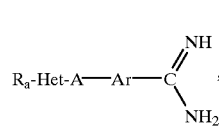

(XVII)

wherein

A, Ar, Het and $R_a$ are as hereinbefore defined, with a compound of general formula

Z₇—R₈, (XVIII)

wherein

R$_8$ denotes one of the abovementioned prodrug groups and

Z$_7$ denotes a leaving group such as a halogen atom, e.g. a chlorine or bromine atom, or a p-nitrophenyl group.

The reaction is conveniently carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of an organic base such as triethylamine, N-ethyl-diisopropylamine, N-methyl-morpholine or pyridine, which may simultaneously serve as solvent, at temperatures between −30 and 100° C., but preferably at temperatures between −10 and 60° C.

If according to the invention a compound of general formula I is obtained which contains an esterified carboxy group, this may be converted by hydrolysis into a corresponding carboxy compound or if a compound of general formula I is obtained which contains a nitro group, this may be converted by reduction into a corresponding amino compound or if a compound of general formula I is obtained which contains an imino group in the Het moiety, this may be converted by alkylation into a corresponding alkylated compound or if a compound of general formula I is obtained which contains a primary or secondary amino group, this may be converted by alkylation or reductive alkylation into a corresponding alkyl or dialkyl compound or if a compound of general formula I is obtained which contains a primary or secondary amino group, this may be converted by acylation into a corresponding acyl compound or if a compound of general formula I is obtained which contains a carbonyl group in the Het moiety, this may be converted by means of a sulphurising agent into a corresponding thiocarbonyl compound or if a compound of general formula I is obtained which contains a carbonyl group in the Het moiety, this may be converted by means of a halogen-introducing agent and subsequent reaction with an amine into a corresponding amino compound, or if a compound of general formula I is obtained which contains an alkenyl or alkynyl function, this may be converted by catalytic hydrogenation into a corresponding saturated compound or if a compound of general formula I is obtained which contains an alkenyl function, this may be converted by oxidation into a corresponding carboxylic acid or if a compound of general formula I is obtained which contains an enolether group, this may be converted by hydrolysis into a corresponding carbonyl compound or if a compound of general formula I is obtained which contains an aliphatic carbonyl group, this may be converted by reaction with a hydroxylamine into a corresponding oxime.

The subsequent hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxan at temperatures between −10 and 120° C., e.g. at temperatures between ambient temperature and the boiling temperature of the reaction mixture.

The subsequent reduction of a nitro group is preferably carried out in a solvent such as water, water/ethanol, methanol, glacial acetic acid, ethyl acetate or dimethylformamide, conveniently with hydrogen in the presence of a hydrogenation catalyst such as Raney nickel, platinum or palladium/charcoal, with metals such as iron, tin or zinc in the presence of an acid, with salts such as iron(II)sulphate, tin(II)chloride, sodium sulphide, sodium hydrogen sulphite or sodium dithionite, or with hydrazine in the presence of Raney nickel at temperatures between 0 and 80° C., but preferably at temperatures between 20 and 40° C.

The subsequent alkylation is conveniently carried out in a solvent such as methylene chloride, tetrahydrofuran, dioxane, dimethylsulphoxide, dimethylformamide or acetone optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously act as solvent, or optionally in the presence of silver carbonate or silver oxide at temperatures between −30 and 100° C., but preferably at temperatures between −10 and 80° C.

The subsequent reductive alkylation is preferably carried out in a suitable solvent such as methanol, methanol/water, methanol/water/ammonia, ethanol, ether, tetrahydrofuran, dioxane or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0 and 100° C., preferably at temperatures between 20 and 80° C.

The subsequent acylation is conveniently carried out with an acid halide or anhydride in a solvent or mixture of solvents such as water, methylene chloride, chloroform, ether, tetrahydrofuran, dioxane or dimethylformamide optionally in the presence of an inorganic or organic base, such as sodium hydroxide, potassium carbonate, triethylamine or pyridine, whilst the last two may simultaneously act as solvent, at temperatures between −25 and 100° C., but preferably at temperatures between −10 and 80° C. However, with a corresponding acid, this is preferably carried out in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxy-succinimide, N,N'-carbonyldiimidazole or N,N'-thionyldiimidazole or triphenylphosphine/carbon tetrachloride, and optionally in the presence of an inorganic base such as sodium carbonate or an organic base such as triethylamine or pyridine, which may simultaneously serve as solvent, at temperatures between −25° C. and 150° C., but preferably at temperatures between −10° C. and the boiling temperature of the solvent used.

The subsequent conversion of a carbonyl group into the corresponding thiocarbonyl group is carried out with a sulphurising agent such as phosphorus pentasulphide or 2,4-bis(4-methoxyphenyl)-1,3-di-thia-2,4-diphosphetan-2,4-disulphide, conveniently in a solvent such as toluene or xylene at temperatures between 50 and 150° C., e.g. at the boiling temperature of the reaction mixture.

The subsequent conversion of a carbonyl group into a halomethyl group in the Het moiety is preferably carried out with a halogen-introducing agent such as a phosphorus oxyhalide or a phosphorus pentahalide at elevated temperatures, e.g. at the boiling temperature of the phosphorus oxychloride used, and the subsequent reaction with a corresponding amine is carried out in a solvent such as ethanol or isopropanol at temperatures between 0 and 50° C.

The subsequent catalytic hydrogenation is carried out with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar.

The subsequent conversion of an alkenyl compound into a corresponding carboxylic acid is conveniently carried out with an oxidising agent such as sodium periodate in the presence of a catalyst such as ruthenium trichloride in a solvent such as methylene chloride, acetonitrile or methylene chloride/acetonitrile hydrochloric acid at temperatures between 0 and 50° C., but preferably at ambient temperature.

The subsequent oxime formation is preferably carried out in a solvent such as methanol, toluene or methanol/toluene optionally in the presence of a tertiary organic base such as triethylamine and in the presence of a water-eliminating agent, e.g. in the presence of a molecular sieve, at elevated temperatures, but preferably at the boiling temperature of the solvent used.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (O) preferably in a solvent such as tetrahydrofuran and preferably in the presence of an excess of a base such as morpholine or 1,3-dimedone at temperatures between 0 and 100° C., preferably at ambient temperature and under inert gas, or by treating with a catalytic amount of tris-(triphenylphosphine)-rho-dium(I)chloride in a solvent such as aqueous ethanol and optionally in the presence of a base such as 1,4-diazabicyclo-[2.2.2]octane at temperatures between 20 and 70° C.

The compounds of general formulae II to XVII used as starting materials, some of which are known from the literature, are obtained by methods known from the literature, moreover their preparation is described in the Examples.

The preparation of a compound of general formula II is described for example in J. Org. Chem. 8, 168–171 (1943), a compound of general formula III in Arzneim. Forsch. 26, 516–517 (1976) and a compound of general formula V in Liebigs Ann. Chem. 1980, 611–621.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereo-chemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl group.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the new compounds of general formula I and the salts thereof have valuable properties. Thus, the compounds of general formula I wherein $R_b$ denotes a cyano group are valuable intermediate products for preparing the other compounds of general formula I and the compounds of general formula I wherein $R_b$ denotes one of the abovementioned amidino groups and the tautomers, the stereoisomers and the physiologically acceptable salts thereof have valuable pharmacological properties, particularly an antithrombotic activity which is preferably based on a thrombin- or factor Xa-influencing effect, e.g. a thrombin-inhibiting or factor Xa-inhibiting effect, an effect of prolonging the aPTT time and an inhibitory effect on related serine proteases such as e.g. trypsin, urokinase factor VIIa, factor IX, factor XI and factor XII.

For example, the following compounds:

A = 4-{[6-(N-carboxymethyl-quinolin-8-yl-sulphonylamino)-1-methyl-2-oxo-1,2-dihydroquinoxalin-3-yl]-methyl}-benzamidine-hydrochloride, B = 4-{[6-(1-(N-cyclopentyl-carboxymethylcarbonylamino)-cyclopropyl)-1-methyl-2-oxo-1,2-dihydroquinoxalin-3-yl]-methyl}-benzamidine-hydrochloride, C=4-{[7-(N-carboxymethylaminocarbonyl-ethylamino)-4-methyl-quinolin-2-yl]-oxo}-benzamidine-hydrochloride, D=4-{[7-(N-(pyridin-2-yl)-N-(2-carboxyethyl)-aminocarbonyl)-4-methyl-quinolin-2-yl]-oxo}-benzamidine-hydrochloride, E=4-{[6-(1-methyl-1-(pyrrolidin-1-yl-carbonyl)-ethyl)-1-methyl-2-oxo-1,2-dihydroquinoxalin-3-yl]-methyl}-benzamidine-hydrochloride, F=4-{[6-(1-(pyrrolidin-1-yl-carbonyl)-cyclopropyl)-1-methyl-2-oxo-1,2-dihydroquinoxalin-3-yl]-methyl}-benzamidine-hydrochloride and G = 4-{[6-(1-(N-methyl-carboxymethylcarbonylaminomethyl)-1-(pyrrolidin-1-yl-carbonyl)-ethyl)-2-oxo-1,2-dihydroquinoxalin-3-yl]-methyl}-benzamidine-hydrochloride were investigated as follows for their effect on prolonging the aPTT time:

Materials: plasma, from human citrated blood.

PTT-reagent, Boehringer Mannheim (524298),
  calcium solution (0.025 mol/l), Behring Werke, Marburg (ORH 056/57),
    diethylbarbiturate acetate buffer, Behring Werke, Marburg (ORWH 60/61),
    Biomatic B10 Koagulometer, Desaga, Wiesloch.

Method:

The aPTT time was determined using a Biomatic B10 coagulometer made by Messrs. Desaga.

The test substance was placed in the test vessels prescribed by the manufacturer with 0.1 ml of human citrated plasma and 0.1 ml of PTT reagent. The mixture was incubated for three minutes at 37° C. The clotting reaction was started by the addition of 0.1 ml of calcium solution. The time is measured using the apparatus from the addition of the calcium solution up to the clotting of the mixture. Mixtures to which 0.1 ml of DBA buffer were added were used as the controls.

According to the definition, a dosage-activity curve was used to determine the effective concentration of the substance, i.e. the concentration at which the aPTT time is double compared with the control.

The Table which follows contains the results found:

| Substance | aPTT-time ($ED_{200}$ in $\mu M$) |
| --- | --- |
| A | 0.950 |
| B | 0.470 |
| C | 0.550 |
| D | 0.370 |
| E | 0.160 |
| F | 0.095 |
| G | 0.170 |

The compounds are well tolerated as no toxic side effects were observed at therapeutic doses.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE 1

4-[(7-benzolsulphonylamino-4,4-dimethyl-1,3-dioxo-3,4-dihydro-1H-isoguinolin-2-yl)-methyl]-benzamidine-hydrochloride a. 4,4-dimethyl-2H-3,4-dihydro-isocuinolin-1,3-dione To 100 ml of glacial acetic acid are added, batchwise, 38.5 g (0.4 mol) ammonium carbonate and then 38 g (0.2 mol) dimethylhomophthalic acid anhydride. Then the mixture is heated for 3 minutes to 130° C. and for 2 hours to 180° C. After cooling the reaction solution is poured onto ice, the product precipitated is suction filtered and dried.

Yield: 31.5 g (83.5% of theory), $R_f$ value: 0,17 (silica gel; methylene chloride).

b. 4,4-dimethyl-7-nitro-2H-3,4-dihydro-isoquinolin-1,3-dione

To 60 ml of fuming nitric acid are added at 15° C. batchwise 18.9 g (0.1 mol) of 4,4-dimethyl-2H-3,4-dihydro-isoquinolin-1,3-dione. The solution is stirred for 60 minutes at 15° C. and poured onto ice water. The product precipitated is suction filtered and dried.

Yield: 22.1 g (95.4% of theory), $R_f$ value: 0.35 (silica gel; methylene chloride/ethanol=19:1).

c. 4-[(4,4-dimethyl-7-nitro-1,3-dioxo-3,4-dihydro-1H-isoquinolin-2-yl)-methyl]-benzonitrile 4.7 g (0, 02 mol) of 4,4-dimethyl-7-nitro-2H-3,4-dihydro-isoquinolin-1,3-dione are dissolved in 40 ml dimethylsulphoxide and after the addition of 2.2 g (0,02 mol) of potassium-tert.butoxide stirred for 15 minutes at ambient temperature. After the addition of 4.3 g (0.022 mol) of 4-bromomethylbenzonitrile the reaction mixture is stirred for 60 minutes, subsequently poured onto water. The product precipitated is suction filtered, the residue is dissolved in ethyl acetate, dried and filtered through activated charcoal. After evaporation of the solvent the product is digested with ether, suction filtered and dried.

Yield: 6.0 g (86% of theory), $R_f$ value: 0.62 (silica gel; methylene chloride/ethanol=50:1); melting point: 172–174° C.

d. 4-[(7-amino-4,4-dimethyl-1,3-dioxo-3,4-dihydro-1H-isoquinolin-2-yl)-methyl]-benzonitrile 3.5 g (0.01 mol) of 4-[(4,4-dimethyl-7-nitro-1,3-dioxo-3,4-dihydro-1H-isoquinolin-2-yl)-methyl]-benzonitrile are suspended in 100 ml methanol and 100 ml ethanol and after the addition of 1.0 g palladium on activated charcoal the mixture is hydrogenated with hydrogen. The catalyst is filtered off and the filtrate is evaporated down.

Yield: 1.7 g (54.7% of theory), $R_f$ value: 0.37 (silica gel; methylene chloride/ethanol 50:1).

e. 4-[(7-benzenesulphonylamino-4,4-dimethyl-1,3-dioxo-3,4-dihydro-1H-isoquinolin-2-yl)-methyl]-benzonitrile 638 mg (2 mmol) of 4-[(7-amino-4,4-dimethyl-1,3-dioxo-3,4-dihydro-1H-isoquinolin-2-yl)-methyl]-benzonitrile are dissolved in 30 ml pyridine and after the addition of 0.26 ml (2 mmol) of benzenesulphonic acid chloride the mixture is heated over a steam bath for 30 minutes. Then the mixture is distilled off in vacuo, the residue chromatographed on silica gel and eluted with methylene chloride/ethanol (99:1). The desired fractions are evaporated down, triturated with ether and acetone, suction filtered and dried.

Yield: 610 mg (66.5% of theory), $R_f$ value: 0.11 (silica gel; methylene chloride).

f. 4-[(7-benzenesulphonylamino-4,4-dimethyl-1,3-dioxo-3,4-dihydro-1H-isoquinolin-2-yl)-methyl]-benzamidine-hydrochloride 550 mg (1.2 mmol) of 4-[(7-benzenesulphonylamino-4,4-dimethyl-1,3-di-oxo-3,4-dihydro-1H-isoquinolin-2-yl)-methyl]-benzonitrile are dissolved in 50 ml of saturated ethanolic hydrochloric acid and stirred for 18 hours at ambient temperature. The solvent is distilled off, the residue is dissolved in 60 ml of absolute ethanol and mixed with 1.0 g (12 mmol) of ammonium carbonate. After 60 hours at ambient temperature the mixture is evaporated to dryness. The residue is chromatographed on silica gel and eluted with methylene chloride/methanol (90:10 and 85:15). The desired fractions are concentrated by evaporation, triturated with ether and suction filtered.

Yield: 500 mg (81.5% of theory), $C_{25}H_{24}N_4O_4S \times HCl$ (476.57/513.03); mass spectrum: $(M+H)^+=477$.

The following compound is prepared analogously:

(1) 4-{[7-(naphthalin-1-yl-sulphonylamino)-4,4-dimethyl-1,3-dioxo-3,4-dihydro-1H-isoquinolin-2-yl]-methyl}-benzamidine-hydrochloride Yield: 69% of theory, $C_{29}H_{26}N_4O_4S \times HCl$ (526.63/563.09); mass spectrum: $(M+H)^+=527$.

EXAMPLE 2

4-[(7-benzenesulphonylamino-4-methyl-1-oxo-1,2-dihydro-1H-isoquinolin-2-yl)-methyl]-benzamidine-hydrochloride a. N-allyl-2-bromo-5-nitro-benzamide To a solution of 2.5 g (0.01 mol) of 2-bromo-5-nitro-benzoic acid in 70 ml tetrahydrofuran are added dropwise 3.2 g (0.01 mol) of O-(benzotriazol-1-yl)-N,N,N'N'-tetramethyluronium-tetrafluoroborate, 5 ml triethylamine and a solution of 570 mg (0.01 mol) of allylamine in 5 ml tetrahydrofuran. After 60 minutes at ambient temperature the mixture is poured onto ice water, the product precipitated is suction filtered, washed with water and dried.

Yield: 1.6 g (54.4% of theory), $R_f$ value: 0.57 (silica gel; ethyl acetate/petroleum ether).

b. 4-methyl-7-nitro-2H-isoquinolin-1-one 1.4 g (5 mmol) of N-allyl-2-bromo-5-nitro-benzamide are heated to 110° C. with 160 mg palladium(II)-acetate, 160 mg triphenylphosphine and 1.2 ml triethylamine in 2.5 ml dimethylformamide under a nitrogen atmosphere for 2 hours. Then the mixture is stirred into ice water and adjusted to pH 5 with glacial acetic acid. The crystalline product with the catalyst is suction filtered and dried. The residue is chromatographed on silica gel and eluted with methylene chloride/ethanol 50:1 and 25:1. The desired fractions are combined and evaporated down. Yield: 95 mg (9.3% of theory), 4-methyl-7-nitro-2H-isoquinolin-1-one.

$R_f$ value: 0.46 (silica gel; methylene chloride/ethanol=19:1).

c. 4-[(7-nitro-4-methyl-1-oxo-1,2-dihydro-1H-isoquinolin-2-yl)-methyl]-benzonitrile 505 mg (2.5 mmol) of 4-methyl-7-nitro-2H-isoquinolin-1-one are dissolved in 50 ml dimethylsulphoxide and after the addition of 1 g potassium carbonate stirred for 15 minutes under a nitrogen atmosphere. After the addition of 588 mg (3 mmol) of 4-(bromomethyl)-benzonitrile the reaction mixture is stirred for 2 hours at ambient temperature and subsequently stirred into ice water. The product precipitated is suction filtered, washed with water and dried.

Yield: 505 mg (63.6% of theory), $R_f$ value: 0.63 (silica gel; methylene chloride/ethanol=19:1).

d. 4-[(7-amino-4-methyl-1-oxo-1,2-dihydro-1H-isoquinolin-2-yl)-methyl]-benzonitrile 500 mg (1.5 mmol) of 4-[(7-nitro-4-methyl-1-oxo-1,2-dihydro-1H-isoquinolin-2-yl)-methyl]-benzonitrile are dissolved in 20 ml methylene chloride and 80 ml ethanol and after the addition of 0.5 g palladium on activated charcoal (10%) hydrogenated with hydrogen for 1 hour. Then the mixture is filtered off from the catalyst and evaporated down. The residue is triturated with ether, suction filtered and dried.

Yield: 395 mg (91% of theory), $R_f$ value: 0.26 (silica gel; methylene chloride/ethanol=19:1).

e. 4-[(7-benzenesulphonylamino-4-methyl-1-oxo-1,2-dihydro-1H-isoquinolin-2-yl)-methyl]-benzonitrile 375 mg (1.3 mmol) of 4-[(7-amino-4-methyl-1-oxo-1,2-dihydro-1H-isoquinolin-2-yl)-methyl]-benzonitrile, 264 mg (1.5 mmol) of benzenesulphonic acid chloride and 50 mg dimethylaminopyridine are stirred in 25 ml pyridine under a nitrogen atmosphere for 18 hours at ambient temperature. Then the mixture is poured onto ice water and adjusted to pH 4 with acetic acid. The precipitate formed is suction filtered, washed with water and dried.

Yield: 360 mg (64.9% of theory), $R_f$ value: 0.54 (silica gel; methylene chloride/ethanol=19:1).

f. 4-[(7-benzenesulphonylamino-4-methyl-1-oxo-1,2-dihydro-1H-isoquinolin-2-yl)-methyl]-benzamidine-hydrochloride Prepared analogously to Example 1f from 4-[(7-benzenesulphonylamino-4-methyl-1-oxo-1,2-dihydro-1H-isoquinolin-2-yl)-methyl]-benzonitrile and hydrochloric acid/ammonium carbonate in ethanol.

Yield: 57.4% of theory, $C_{24}H_{23}N_4O_3S\times HCl$ (446.5/492.97); mass spectrum: $(M+H)^+=447$.

EXAMPLE 3

4-[(7-benzenesulphonylamino-1-n-propyl-1,4-dihydro-2H-quinazolin-2,4-dion-3-yl)-methyl]-benzamidine-hydrochloride a. 2-amino-N-(4-cyano-benzyl)-4-nitro-benzamide 31.7 g (0.17 mol) of 4-nitro-anthranilic acid are dissolved in 350 ml dimethylformamide and after the addition of 45.4 g (0.28 mol) of N,N'-carbonyldiimidazole stirred for 30 minutes at 50° C. Then a solution of 23 g (0.17 mol) of 4-aminomethyl-benzonitrile in 100 ml dimethylformamide is added dropwise and stirred for 2 hours at 50° C. The solution is evaporated down, dissolved in ethyl acetate and extracted with sodium hydrogen carbonate solution. The combined organic extracts are dried and evaporated down. The residue is chromatographed on silica gel and eluted with methylene chloride/ethanol (97:3).

Yield: 33.8 g (66% of theory), $R_f$ value: 0.65 (silica gel; petroleum ether/ethyl acetate=1:1).

b. 4-[(7-nitro-1,4-dihydro-2H-quinazolin-2,4-dion-3-yl)-methyl]-benzonitrile 33.5 g (0.11 mol) of 2-amino-N-(4-cyano-benzyl)-4-nitro-benzamide are dissolved in 275 ml pyridine and 33.6 g (0.11 mol) of triphosgene are added batchwise whilst the temperature rises to 50° C. After for 2 hours at 70° C. the pyridine is distilled off in vacuo, the residue is triturated with water, suction filtered and dried.

Yield: 35.8 g (98% of theory), $R_f$ value: 0.5 (silica gel; methylene chloride/acetone=9:1).

c. 4-[(7-nitro-1-n-propyl-1,4-dihydro-2H-quinazolin-2,4-dion-3-yl)-methyl]-benzonitrile Prepared analogously to Example 1c from 4-[(7-nitro-1,4-dihydro-2H-quinazolin-2,4-dion-3-yl)-methyl]-benzonitrile, propyl iodide and potassium carbonate in dimethyl sulphoxide.

Yield: 86% of theory, $R_f$ value: 0.76 (silica gel; petroleum ether/ethyl acetate=2:1).

d. 4-[(7-amino-1-n-propyl-1,4-dihydro-2H-quinazolin-2,4-dion-3-yl)-methyl]-benzonitrile 5.0 g (0.014 mol) of 4-[(7-nitro-1-n-propyl-1,4-dihydro-2H-quinazolin-2,4-dion-3-yl)-methyl]-benzonitrile are dissolved in 150 ml methanol and 150 ml methylene chloride and after the addition of 4 g Raney nickel hydrogenated for 7 hours with hydrogen. The catalyst is filtered off, the solvent is distilled off and the residue is chromatographed on silica gel, eluting with methylene chloride/ethyl acetate/ammonia (97:3:0.3). The desired fractions are combined and evaporated down.

Yield: 1.9 g (40% of theory), $R_f$ value: 0.5 (silica gel; methylene chloride/ethyl acetate/ammonia=9:1:0.1).

e. 4-[(7-benzenesulphonylamino-1-n-propyl-1,4-dihydro-2H-quinazolin-2,4-dion-3-yl)-methyl]-benzonitrile Prepared analogously to Example 1e from 4-[(7-amino-1-n-propyl-1,4-dihydro-2H-quinazolin-2,4-dion-3-yl)-methyl]-benzonitrile, benzenesulphonic acid chloride and dimethylaminopyridine in pyridine.

Yield: 89% of theory, $R_f$ value: 0.88 (silica gel; ethyl acetate/ethanol=9:1).

f. 4-[(7-benzenesulphonylamino-1-n-propyl-1,4-dihydro-2H-quinazolin-2,4-dion-3-yl)-methyl]-benzamidine-hydrochloride Prepared analogously to Example 1f from 4-[(7-benzenesulphonylamino-1-n-propyl-1,4-dihydro-2H-quinazolin-2,4-dion-3-yl)-methyl]-benzonitrile and hydrochloric acid/ammonium carbonate in ethanol.

Yield: 50% of theory, $C_{25}H_{25}N_5O_4S\times HCl$ (491,57/528,03); mass spectrum: $(M+H)^+=492$.

The following compounds are prepared analogously:

(1) 4-{[7-(quinolin-8-yl-sulphonylamino)-1-n-propyl-1,4-dihydro-2H-quinazolin-2,4-dion-3-yl]-methyl}-benzamidine-hydrochloride Yield: 66% of theory, $C_{28}H_{27}N_6O_4S\times HCl$ (542,63/579,10); mass spectrum: $(M+H)^+=543$;

$(M+Na)^+=565$;

$(M+2Na)^{++}=294$.

(2) 4-{[7-(naphthalin-1-yl-sulphonylamino)-1-n-propyl-1,4-dihydro-2H-quinazolin-2,4-dion-3-yl]-methyl}-benzamidine-hydrochloride Yield: 80% of theory, $C_{29}H_{27}N_5O_4S\times HCl$ (541.64/578.11); mass spectrum: $(M+H)^+=542$;

$(M+Na)^+=564$.

(3) 4-{[7-(naphthalin-2-yl-sulphonylamino)-1-n-propyl-1,4-dihydro-2H-quinazolin-2,4-dion-3-yl]-methyl}-benzamidine-hydrochloride Yield: 98% of theory, $C_{29}H_{27}N_5O_4S\times HCl$ (541.64/578.11); mass spectrum: $(M+H)^+=542$.

(4) 4-[(7-benzenesulphonylamino-1-ethoxycarbonylmethyl-1,4-dihydro-2H-quinazolin-2,4-dion-3-yl)-methyl]-benzamidine-hydrochloride Yield: 59% of theory, $C_{26}H_{25}N_5O_6S\times HCl$ (535.59/572.06); mass spectrum: $(M+H)^+=536$.

EXAMPLE 4

4-{[7-(N-(2-dimethylaminoethyl)-quinolin-8-yl-sulphonylamino)-1-n-propyl-1,4-dihydro-2H-quinazolin-2,4-dion-3-yl)methyl}-benzamidine-dihydrochloride a. 4-{[7-(N-(2-dimethylaminoethyl)-quinolin-8-ylsulphonylamino)-1-n-propyl-1,4-dihydro-2H-quinazolin-2,4-dion-3-yl]-methyl}benzonitrile 800 mg (1.52 mmol) of 4-{[7-(quinolin-8-yl-sulphonylamino)-1-n-propyl-1,4-dihydro-2H-quinazolin-2,4-dion-3-yl]-methyl}-benzonitrile, 260 mg (1.8 mmol) of dimethylaminoethylchloride, 350 mg (2.3 mmol) of 1,8-diazabicyclo[5.4.0]undec-7-ene and 1.5 g potassium carbonate are refluxed in 120 ml acetone for 30 hours. The solvent is distilled off and mixed with water. The crystalline product is suction filtered and washed with water. The residue is chromatographed on silica gel and eluted with methylene chloride/ethanol (97.5:2.5).

Yield: 500 mg (55% of theory), $R_f$ value: 0.21 (silica gel; methylene chloride/ethanol=9.5:0.5).

b. 4-{[7-(N-(2-dimethylaminoethyl)-quinolin-8-yl-sulphonylamino)-1-n-propyl-1,4-dihydro-2H-quinazolin-2,4-dion-3-yl)-methyl-benzamidine-dihydrochloride Prepared analogously to Example 1f from 4-{[7-(N-(2-dimethylaminoethyl)-quinolin-8-yl-sulphonylamino)-1-n-propyl-1,4-dihydro-2H-quinazolin-2,4-dion-3-yl)-methyl-benzonitrile and hydrochloric acid/ammonium carbonate in ethanol.

Yield: 92% of theory, $C_{32}H_{35}N_7O_4S \times 2$ HCl (613,75/686, 67); mass spectrum: $(M+H)^+=614$;

$(M+2H)^{++}=307.6$.

EXAMPLE 5

4-[(7-benzenesulphonylamino-2-methyl-4H-quinazolin-4-on-3-yl)-methyl]-benzamidine-hydrochloride a. 2-methyl-7-nitro-3H-quinazolin-4-one 18.2 g (0.1 mol) of 2-amino-4-nitro-benzoic acid are dissolved in 100 ml ethyleneglycol monoethyl ether and after the addition of 18.6 g (0.15 mol) of ethyl acetimidate and 24 ml (0.17 mol) of triethylamine refluxed for 9 hours. After cooling the precipitate is suction filtered, the residue is chromatographed on silica gel and eluted with methylene chloride/ethanol (97:3).

Yield: 7.3 g (35.8% of theory), $R_f$ value: 0.62 (silica gel; methylene chloride/ethanol=9:1).

b. 4-[(2-methyl-7-nitro-4-oxo-4H-quinazolin-3-yl)-methyl]-benzonitrile 8.0 g (0.04 mol) of 2-methyl-7-nitro-3H-quinazolin-4-one are stirred in 100 ml acetone and after the addition of 5.5 g (0.04 mol) of potassium carbonate and 7.8 g (0.04 mol) of p-cyanobenzylbromide stirred for 4 hours at ambient temperature and 4 hours at 50° C. After filtration the mother liquor is evaporated down and the residue is chromatographed on silica gel eluting with methylene chloride/ethanol (99:1 and 98:2). The desired fractions are combined and evaporated down.

Yield: 4.2 g (34% of theory), $R_f$ value: 0.53 (silica gel; methylene chloride/ethanol=9,5:0.5).

c. [4-(7-amino-2-methyl-4-oxo-4H-quinazolin-3-yl)-methyl]-benzonitrile

Prepared analogously to Example 3d from 4-[(2-methyl-7-nitro-4-oxo-4H-quinazolin-3-yl)-methyl]-benzonitrile and Raney nickel/hydrogen in methylene chloride/methanol.

Yield: 72% of theory, $R_f$ value: 0.3 (silica gel; methylene chloride/ethanol=9.5:0.5).

d. 4-[(7-benzenesulphonylamino-2-methyl-4H-quinazolin-4-on-3-yl)-methyl]-benzonitrile Prepared analogously to Example 1e from 4-[(7-amino-2-methyl-4-oxo-4H-quinazolin-3-yl)-methyl]-benzonitrile, benzenesulphonic acid chloride and dimethylaminopyridine in pyridine.

Yield: 90% of theory, $R_f$ value: 0.58 (silica gel; methylene chloride/ethanol=9:1).

e. 4-[(7-benzenesulphonylamino-2-methyl-4H-quinazolin-4-on-3-yl)-methyl]-benzamidine-hydrochloride Prepared analogously to Example 1f from 4-[(7-benzenesulphonylamino-2-methyl-4H-quinazolin-4-on-3-yl)-methyl]-benzonitriue and hydrochloric acid/ammonium carbonate in ethanol.

Yield: 91% of theory, $C_{23}H_{21}N_5O_3S \times HCl$ (447,53/484, 00); mass spectrum: $(M+H)^+=448$.

The following compounds are prepared analogously:

(1) 4-{[7-(N-(2-dimethylaminoethyl)-benzenesulphonylamino)-2-methyl-4H-quinazolin-4-on-3-yl)-methyl]-benzamidine-dihydrochloride Yield: 65% of theory, $C_{27}H_{30}N_6O_3S \times HCl$ (518.65/555, 12); mass spectrum: $(M+H)^+=519$;

$(M+2H)^{++}=260$.

(2) 4-[(6-benzenesulphonylamino-2-methyl-4H-quinazolin-4-on-3-yl)-methyl]-benzamidine-hydrochloride Yield: 100% of theory, $C_{23}H_{21}N_5O_3S \times HCl$ (447.53/484.00); mass spectrum: $(M+H)^+=448$.

(3) 4-{[6-(N-(2-dimethylaminoethyl)-benzenesulphonylamino)-2-methyl-4H-quinazolin-4-on-3-yl]-methyl}-benzamidine-dihydrochloride Yield: 93% of theory, $C_{27}H_{30}N_6O_3S \times HCl$ (518.65/555, 12); mass spectrum: $(M+H)^+=519$;

$(M+2H)^{++}=260$.

EXAMPLE 6

4-[(6-benzenesulphonylamino-4-oxo-3,4-dihydroquinazolin-2-yl)-methyl]-benzamidine-hydrochloride a. Methyl (4-cyano-phenyl)-acetate 30.0 g (0.15 mol) of 4-bromomethyl-benzonitrile, 2.0 ml (0.12 mol) of iron pentacarbonyl, 29.0 g potassium carbonate, 10.0 ml mesitylene and 250 ml absolute methanol are placed in a pressure vessel and about 3.5 l carbon monoxide gas is introduced. The reaction mixture is shaken for 16 hours at ambient temperature, mixed with water, neutralised with hydrochloric acid and extracted with ethyl acetate. The combined organic extracts are washed with sodium hydrogen carbonate solution, dried and evaporated down. The residue is chromatographed on silica gel and eluted with petroleum ether/ethyl acetate (9:1, 8:2 and 7:3). The desired fractions are combined and evaporated down.

Yield: 18.3 g (69.4% of theory), $C_{10}H_9NO_2$ (175.2); mass spectrum: $M^+=175$.

b. (4-cyano-phenyl)-acetic acid 14.2 g (0.081 mol) of methyl(4-cyano-phenyl)-acetate are dissolved in 100 ml ethanol and after the addition of 20 ml 2N sodium hydroxide solution stirred for 1 hour at ambient temperature. The solvent is distilled off, the residue is mixed with ice water and glacial acetic acid. The substance precipitated is suction filtered and dried.

Yield: 10.3 g (78% of theory).

c. Methyl 2-[2-(4-cyano-phenyl)-acetylamino]-5-nitro-benzoate 4.8 g (3 mmol) of (4-cyano-phenyl)-acetic acid are suspended in 25 ml of methylene chloride and refluxed for 15 minutes after the addition of 5 ml thionyl chloride. The solvent is distilled off, the residue dissolved in 100 ml chlorobenzene and after the addition of 4.9 g (2.5 mmol) of methyl 2-amino-5-nitro-benzoate refluxed for 2 hours. Three-quarters of the volume of chlorobenzene is distilled off and the residue is combined with ether/petroleum ether. The crystalline product is suction filtered and dried.

Yield: 5.7 g (69.4% of theory).

d. 4-[(6-nitro-4-oxo-3,4-dihydro-quinazolin-2-yl)-methyl]-benzonitrile 1.6 g (5 mmol) of methyl 2-[2-(4-cyano-phenyl)-acetylamino]-5-nitro-benzoate, 1.1 g (20 mmol) of ammonium chloride, 3.0 g (21 mmol) of phosphorus pentoxide and 2.5 g (20 mmol) of N,N-dimethylcyclohexylamine are stirred at 190° C. for 30 minutes. Then the mixture is cooled to 100° C., adjusted to pH 8 with 2N sodium hydroxide solution and stirred for 1 hour at 80° C. The precipitate formed is suction filtered, washed with water and dried. The residue is chromatographed on silica gel and eluted initially with petroleum ether/ethyl acetate (1:1) and then with ethyl acetate/ethanol (9:1). The desired fractions are combined and evaporated down.

Yield: 365 mg (23.8% of theory), $R_f$ value: 0.63 (silica gel; methylene chloride/ethanol=19:1).

e. 4-[(6-amino-4-oxo-3,4-dihydro-quinazolin-2-yl)-methyl]-benzonitrile

Prepared analogously to Example 1d from 4-[(6-nitro-4-oxo-3,4-dihydro-quinazolin-2-yl)-methyl]-benzonitrile and palladium on activated charcoal/hydrogen in methylene chloride/ethanol.

Yield: 71% of theory, $R_f$ value: 0.26 (silica gel; methylene chloride/ethanol=19:1).

f. 4-[(6-benzenesulphonylamino-4-oxo-3,4-dihydroquinazolin-2-yl)-methyl]-benzonitrile Prepared analogously to Example 1e from 4-[(6-amino-4-oxo-3,4-dihydro-quinazolin-2-yl)-methyl]-benzonitrile, benzenesulphonic acid chloride and dimethylaminopyridine in pyridine.

Yield: 80.5% of theory, melting point: 235–237° C.

g. 4-[(6-benzenesulphonylamino-4-oxo-3,4-dihydroquinazolin-2-yl)-methyl]-benzamidine-hydrochloride Prepared analogously to Example 1f from 4-[(6-benzenesulphonylamino-4-oxo-3,4-dihydroquinazolin-2-yl)-methyl]-benzonitrile and hydrochloric acid/ammonium carbonate in ethanol.

Yield: 48.3% of theory, $C_{22}H_{19}N_5O_3S \times HCl$ (433.49/469.95); mass spectrum: $(M+H)^+=434$.

The following compounds are prepared analogously:

(1) 4-[(6-(quinolin-8-yl-sulphonylamino)-4-oxo-3,4-dihydroquinazolin-2-yl)-methyl]-benzamidine-hydrochloride Yield: 28.7% of theory, $C_{25}H_{20}N_6O_3S \times HCl$ (484.54/521,00); mass spectrum: $(M+H)^+=485$.

(2) 4-[(6-benzenesulphonylamino-3-methyl-4-oxo-3,4-dihydroquinazolin-2-yl)-methyl]-benzamidine-hydrochloride Yield: 20.9% of theory, $C_{23}H_{21}N_5O_3S \times HCl$ (447.51/483.97); mass spectrum: $(M+H)^+=448$.

EXAMPLE 7

4-[(6-benzenesulphonylamino-1-methyl-2-oxo-1,2-dihydroquinoxalin-3-yl)-methyl]-benzamidine-hydrochloride a. 2-methylamino-5-nitro-aniline 3.3 g (20 mmol) of 2-fluoro-5-nitro-aniline are dissolved in 50 ml of methylamine solution (40%) and stirred for 3 days at ambient temperature. The precipitate is suction filtered and dried.

Yield: 3.3 g (98.8% of theory), $R_f$ value: 0.65 (silica gel; ethyl acetate).

b. Diethyl 2-acetylamino-2-(4-cyano-benzyl)-malonate 3.0 g sodium are dissolved in 100 ml ethanol and subsequently combined with a solution of 27.7 g (0.127 mol) of diethyl acetamidomalonate and 6.4 g (0.04 mol) of potassium iodide in 200 ml dioxane. Then a solution of 25 g (0.127 mol) of 4-cyanobenzylbromide in 200 ml dioxane is added dropwise and the reaction mixture is refluxed for 3 hours. After 12 hours at ambient temperature the mixture is filtered, the filtrate is evaporated down, the residue is crystallised with petroleum ether and suction filtered.

Yield: 41.1 g (97% of theory), $R_f$ value: 0.62 (silica gel; methylethylketone/xylene 1:1); melting point: 177–78° C.

c. 2-amino-3-(4-cyano-phenyl)-provionic acid 40 g (0.12 mol) of diethyl 2-acetylamino-2-(4-cyano-benzyl)-malonate are dissolved in 110 ml glacial acetic acid, 50 ml concentrated hydrochloric acid and 135 ml water and refluxed for 8 hours. The solution is evaporated down in vacuo, the residue is crystallised with isopropanol/ether, suction filtered and dried.

Yield: 18.6 g (68% of theory), $R_f$ value: 0.37 (silica gel; methylethylketone/xylene=1:1).

d. 4-[(5-oxo-2-trifluoromethyl-4,5-dihydro-oxazol-4-yl)-methyl]-benzonitrile 5.7 g (2.5 mmol) of 2-amino-3-(4-cyano-phenyl)-propionic acid are dissolved in 26.3 g (12.5 mmol) of trifluoroacetic acid anhydride and refluxed for 24 hours. Then the solution is evaporated down in vacuo, the residue is chromatographed on silica gel and eluted with methylene chloride. The desired fractions are combined and evaporated down.

Yield: 3.6 g (53% of theory), $R_f$ value: 0.71 (silica gel; methylethylketone/xylene=1:1).

e. 3-(4-cyano-phenyl)-2-oxo-propionic acid 3.5 g (0.013 mol) of 4-(5-oxo-2-trifluoromethyl-4,5-dihydrooxazol-4-yl)-methyl-benzonitrile are dissolved in 20 ml of 70% trifluoroacetic acid and stirred for 24 hours at ambient temperature. The solid formed is suction filtered, washed with water and dried.

Yield: 1.8 g (75% of theory), $R_f$ value: 0.2 (silica gel; methylene chloride/ethanol=9:1).

f. 4-[(6-nitro-1-methyl-2-oxo-1,2-dihydroquinoxalin-3-yl)-methyl]-benzonitrile 1.0 g (6.3 mmol) of 2-methylamino-5-nitro-aniline and 1.2 g (6.3 mmol) of 3-(4-cyano-phenyl)-2-oxo-propionic acid are refluxed for 15 hours in 15 ml ethanol. Then the mixture is cooled, the precipitate formed is suction filtered and dried.

Yield: 1.3 g (64.3% of theory), $R_f$ value: 0.76 (silica gel; ethyl acetate).

g. 4-[(6-amino-1-methyl-2-oxo-1,2-dihydroquinoxalin-3-yl)-methyl]-benzonitrile

Prepared analogously to Example 3d from 4-[(6-nitro-1-methyl-2-oxo-1,2-dihydroquinoxalin-3-yl)-methyl]-benzonitrile and palladium on activated charcoal/hydrogen in methylene chloride/methanol.

Yield: 100% of theory, $R_f$ value: 0.3 (silica gel; ethyl acetate).

h. 4-[(6-benzenesulphonylamino-1-methyl-2-oxo-1,2-dihydroquinoxalin-3-yl)-methyl]-benzonitrile Prepared analogously to Example 1e from 4-[(6-amino-1-methyl-2-oxo-1,2-dihydroquinoxalin-3-yl)-methyl]-benzonitrile and benzenesulphonic acid chloride in pyridine.

Yield: 90.9% of theory, $R_f$ value: 0.71 (silica gel; ethyl acetate).

i. 4-[(6-benzenesulphonylamino-1-methyl-2-oxo-1,2-dihydroquinoxalin-3-yl)-methyl]-benzamidine-hydrochloride Prepared analogously to Example 1f from 4-[(6-benzenesulphonylamino-1-methyl-2-oxo-1,2-dihydroquinoxalin-3-yl)-methyl]-benzonitrile and hydrochloric acid/ammonium carbonate in ethanol.

Yield: 49.5% of theory, $C_{23}H_{21}N_5O_3S \times HCl$ (447.51/483.97); mass spectrum: $(M+H)^+=448$.

The following compounds are prepared analogously:

(1) 4-[(6-(quinolin-8-yl-sulphonylamino)-1-methyl-2-oxo-1,2-dihydroquinoxalin-3-yl)-methyl]-benzamidine-hydrochloride Yield: 47.7% of theory, $C_{26}H_{22}N_6O_3S \times HCl$ (498.56/535.02); mass spectrum: $(M+H)^+=499$.

(2) 4-[(6-tert.butylcarbonyl-1-methyl-2-oxo-1,2-dihydroquinoxalin-3-yl)-methyl]-benzamidine-hydrochloride Yield: 37% of theory, $C_{22}H_{24}N_4O_2 \times HCl$ (376.5/412.9); mass spectrum: $(M+H)^+=377$.

(3) 4-[(6-(1-methyl-cyclopentan-1-yl-carbonyl)-1-methyl-2-oxo-1,2-dihydroquinoxalin-3-yl)-methyl]-benzamidine-hydrochloride Yield: 47% of theory, $C_{24}H_{26}N_4O_2 \times HCl$ (402.5/439.0); mass spectrum: $(M+H)^+=403$.

(4) 4-[(6-bromo-1-methyl-2-oxo-1,2-dihydroquinoxalin-3-yl)-methyl]-benzamidine-hydrochloride Yield: 80% of theory, $C_{17}H_{15}BrN_4O \times HCl$ (371.26/407.72); mass spectrum: $M^+=370/2$ (Br).

(5) 4-[(6-(2-methyl-propionyl)-1-methyl-2-oxo-1,2-dihydroquinoxalin-3-yl)-methyl]-benzamidine-hydrochloride Yield: 74.9% of theory, $C_{21}H_{22}N_4O_2 \times HCl$ (362.44/398.9); mass spectrum: $(M+H)^+=363$.

(6) 4-[(6-(1-ethoxycarbonylmethyloxyimino-ethylidene)-1-methyl-2-oxo-1,2-dihydroquinoxalin-3-yl)-methyl]-benzamidine-hydrochloride Yield: 98% of theory, $C_{23}H_{25}N_5O_4 \times HCl$ (435.49/471.96). mass spectrum: $(M+H)^+=436$.

(7) 4-[(6-propionyl-1-methyl-2-oxo-1,2-dihydroquinoxalin-3-yl)-methyl]-benzamidine-hydrochloride Yield: 100% of theory, $C_{20}H_{20}N_4O_2 \times HCl$ (348.40/384.88); mass spectrum: $M^+=348$.

EXAMPLE 8

4-{[6-(N-methoxycarbonylmethyl-quinolin-8-yl-sulphonylamino)-1-methyl-2-oxo-1,2-dihydroquinoxalin-3-yl]-methyl}-benzamidine-hydrochloride a. 4-{[6-(N-methoxycarbonylmethyl-quinolin-8-yl-sulphonylamino)-1-methyl-2-oxo-1,2-dihydroquinoxalin-3-yl]-methyl}-benzonitrile 2.0 g (4.15 mmol) of 4-{[6-(quinolin-8-yl-sulphonylamino)-1-methyl-2-oxo-1,2-dihydroquinoxalin-3-yl]-methyl}-benzonitrile are dissolved in 150 ml tetrahydrofuran and after the addition of 0.2 g (4.15 mmol) of sodium hydride (50% in oil) stirred for 2 hours at ambient temperature. After the addition of 0.47 ml (4.15 mmol) of ethyl bromoacetate the reaction mixture was stirred for 5 hours. The precipitate is suction filtered, the mother liquor is evaporated down and chromatographed on silica gel, eluting initially with petroleum ether and then with petroleum ether/ethyl acetate (55:45). The desired fractions are combined and evaporated down.

Yield: 1.7 g (59.1% of theory), $R_f$ value: 0.4 (silica gel; ethyl acetate/petroleum ether=3:1).

b. 4-{[6-(N-methoxycarbonylmethyl-quinolin-8-yl-sulphonylamino)-1-methyl-2-oxo-1,2-dihydroquinoxalin-3-yl]-methyl}-benzamidine-hydrochloride Prepared analogously to Example 1f from 4-{[6-(N-methoxycarbonylmethyl-quinolin-8-yl-sulphonylamino)-1-methyl-2-oxo-1,2-dihydroquinoxalin-3-yl]-methyl}-benzonitrile and hydrochloric acid/ammonium carbonate in ethanol.

Yield: 62.5% of theory, $C_{29}H_{26}N_6O_5S \times HCl$ (570.61/607,08); mass spectrum: $(M+H)^+=571$.

EXAMPLE 9

4-{[6-(N-methoxycarbonylmethyl-quinolin-8-yl-sulphonylamino]-1-methyl-2-oxo-1,2-dihydroquinoxalin-3-yl]-methyl}-N'-ethoxy-carbonyl-benzamidine 450 mg (0.74 mmol) of 4-{[6-(N-methoxycarbonylmethyl-quinolin-8-yl-sulphonylamino)-1-methyl-2-oxo-1,2-dihydroquinoxalin-3-yl]-methyl}benzamidine-hydrochloride are dissolved in 30 ml tetrahydrofuran and 5 ml water and after the addition of 0.3 g (2.2 mmol) of potassium carbonate, stirred for 10 minutes at ambient temperature. Then 0.07 ml (0.74 mmol) of ethyl chloroformate are added and stirred for a further 1 hour. The aqueous phase is separated off, the organic phase is dried and evaporated down.

Yield: 430 mg (89.6% of theory), $C_{32}H_{30}N_6O_5S$ (642.68); mass spectrum: $(M+H)^+=643$;

$(M+Na)^+=665$.

The following compounds are prepared analogously:

(1) 4-{[6-(N-methoxycarbonylmethyl-quinolin-8-yl-sulphonylamino)-1-methyl-2-oxo-1,2-dihydroquinoxalin-3-yl]-methyl}-N'-cyclohexyloxycarbonyl-benzamidine Yield: 63.7% of theory, $C_{36}H_{36}N_6O_7S$ (696.78); mass spectrum: $(M+H)^+=697$.

(2) 4-{[6-(N-ethoxycarbonylmethylquinolin-8-yl-sulphonylamino)-1-methyl-2-oxo-1,2-dihydroquinoxalin-3-yl]-methyl}-N'-methoxycarbonyl-benzamidine Yield: 23.2% of theory, $C_{32}H_{30}N_6O_7S \times HCl$ (642.69); mass spectrum: $(M+H)^+=643$.

(3) 4-{[6-(N-ethoxycarbonylmethylquinolin-8-yl-sulphonylamino)-1-methyl-2-oxo-1,2-dihydroquinoxalin-3-yl]-methyl}-N'-benzyloxycarbonyl-benzamidine Yield: 20.7% of theory, $C_{38}H_{34}N_6O_7S$ (718.78); mass spectrum: $(M+H)^+=719$;

$(M+Na)^+=741$.

(4) 4-{[6-(N-ethoxycarbonylmethylquinolin-8-yl-sulphonylamino)-1-methyl-2-oxo-1,2-dihydroquinoxalin-3-yl]-methyl}-N'-[17-(1,5-dimethyl-hexyl)-10,13-dimethyl-2,3,4,7,8,9,10,11,12,13,14,15,–16,17-tetradecahydro-1H-cyclopenta[a]phenanthren-3-yl]-oxycarbonyl-benzamidine Yield: 31% of theory, $C_{58}H_{72}N_6O_7S$ (997,32); mass spectrum: $(M+H)^+=997$;

$(M+Na)^+=1019$.

(5) 4-{[6-(N-ethoxycarbonylmethyl-quinolin-8-yl-sulphonylamino)-1-methyl-2-oxo-1,2-dihydroquinoxalin-3-yl]-methyl}-N'-n-octyloxycarbonyl-benzamidine Yield: 81.8% of theory, $C_{39}H_{44}N_6O_7S$ (740.78); mass spectrum: $(M+H)^+=741$;

$(M+2H)^{++}=371$.

(6) 4-{[6-(N-ethoxycarbonylmethyl-quinolin-8-yl-sulphonylamino)-1-methyl-2-oxo-1,2-dihydroquinoxalin-3-yl]-methyl}-N-(n-hexyloxycarbonyl)-benzamidine Yield: 73.4% of theory, $C_{37}H_{40}N_6O_7S$ (712.82); mass spectrum: $(M+H)^+=713$.

(7) 4-{[6-(N-ethoxycarbonylmethyl-quinolin-8-yl-sulphonylamino)-1-methyl-2-oxo-1,2-dihydroquinoxalin-3-yl]-methyl}-N-(n-hexyloxycarbonyl)-benzamidine Yield: 72% of theory, $C_{38}H_{42}N_6O_7S$ (726.85); mass spectrum: $(M+H)^+=727$.

(8) 4-{[6-(N-ethoxycarbonylmethyl-quinolin-8-yl-sulphonylamino)-1-methyl-2-oxo-1,2-dihydroquinoxalin-3-yl]-methyl}-N-(n-hexyloxycarbonyl)-benzamidine Yield: 87.4% of theory, $C_{47}H_{60}N_6O_7S$ (853.10); mass spectrum: $(M+H)^+=853$;

$(M+Na)^+=875$.

(9) 4-{[6-(N-ethoxycarbonylmethyl-quinolin-8-yl-sulphonylamino)-1-methyl-2-oxo-1,2-dihydroquinoxalin-3-yl]-methyl}-N-(2-methoxyethyloxycarbonyl)-benzamidine Yield: 68.5% of theory, $C_{34}H_{34}N_6O_8S$ (686.75); mass spectrum: $(M+H)^+=687$.

EXAMPLE 10

4-{[6-(N-carboxymethyl-quinolin-8-yl-sulphonylamino)-1-methyl-2-oxo-1,2-dihydroquinoxalin-3-yl]-methyl}-benzamidine-hydrochloride 300 mg (0.49 mmol) of 4-{[6-(N-ethoxycarbonylmethyl-quinolin-8-yl-sulphonylamino)-1-methyl-2-oxo-1,2- dihydroquinoxalin-3-yl]-methyl}-benzamidine-hydrochloride are dissolved in 5 ml ethanol and, after the addition of 4.9 ml 1N sodium hydroxide solution, stirred for 1 hour at ambient temperature. The solvent is distilled off, the residue is acidified with hydrochloric acid and stirred for 5 hours. Then the mixture is evaporated down, mixed with water and stirred overnight. The precipitate is suction filtered and dried.

Yield: 220 mg (75.9% of theory), $C_{28}H_{24}N_6O_5S \times HCl$ (556.60/593,06); mass spectrum: $(M+H)^+=557$;

$(M+Na)^+=579$.

The following compounds are prepared analogously:

(1) 4-{[6-(N-(2-carboxyethyl)-N-isobutyl-aminocarbonyl)-1-methyl-2-oxo-1,2-dihydroquinoxalin-3-yl]-methyl}-benzamidine-hydrochloride Yield: 43% of theory, $C_{25}H_{29}N_5O_4 \times HCl$ (463.5/500.0); mass spectrum: $(M+H)^+=464$.

(2) 4-{[6-(N-(2-carboxyethyl)-N-phenyl-aminocarbonyl)-1-methyl-2-oxo-1,2-dihydroquinoxalin-3-yl]-methyl}-benzamidine-hydrochloride Yield: 44% of theory, $C_{27}H_{25}N_5O_4 \times HCl$ (483.54/520.01); mass spectrum: $(M+H)^+=484$;

$(M+Na)^+=506$.

(3) 4-{[6-(N-(2-carboxyethyl)-4-isobutyl-imidazol-5-yl)-1-methyl-2-oxo-1,2-dihydroquinoxalin-3-yl]-methyl}-benzamidine-hydrochloride Yield: 51% of theory, $C_{26}H_{28}N_6O_3 \times HCl$ (472.56/509.02); mass spectrum: $(M+H)^+=473$.

$(M+2H)^{++}=237$.

(4) 4-{[6-(N-cyclopentyl-carboxymethylsulphonylamino)-1-methyl-2-oxo-1,2-dihydroquinoxalin-3-yl]-methyl}-benzamidine-hydrochloride Yield: 28.8% of theory, $C_{24}H_{27}N_5O_5S \times HCl$ (497.59/534.05); mass spectrum: $(M+H)^+=498$;

$(M+Na)^+=520$.

(5) 4-{[6-(1-carboxymethylaminocarbonyl-1-methyl-ethyl)-1-methyl-2-oxo-1,2-dihydroquinoxalin-3-yl]-methyl}-benzamidine-hydrochloride Yield: 69.8% of theory, $C_{23}H_{25}N_5O_4 \times HCl$ (435.9/472.36); mass spectrum: $(M+H)^+=436$.

(6) 4-{[6-(1-carboxymethylaminocarbonyl-cyclopropyl)-1-methyl-2-oxo-1,2-dihydroquinoxalin-3-yl]-methyl}-benzamidine-hydrochloride Yield: 65.7% of theory, $C_{23}H_{23}N_5O_4 \times HCl$ (433.48/469.94); mass spectrum: $(M+H)^+=434$.

(7) 4-{[6-(1-carboxymethylcarbonylamino-1-(pyrrolidin-1-yl-carbonyl)-ethyl)-1-methyl-2-oxo-1,2-dihydroquinoxalin-3-yl]-methyl}-benzamidine-hydrochloride Yield: 97% of theory, $C_{27}H_{36}N_6O_5 \times HCl$ (518.58/555.05); mass spectrum: $(M+H)^+=519$;

$(M+Na)^+=541$.

(8) 4-{[6-(N-methyl-carboxymethylaminocarbonyl)-1-methyl-ethyl)-1-methyl-2-oxo-1,2-dihydroquinoxalin-3-yl]-methyl}-benzamidine-hydrochloride Yield: 58% of theory, $C_{24}H_{27}N_5O_4 \times HCl$ (449.52/485.99); mass spectrum: $(M+H)^+=450$.

(9) 4-{[6-(1-carboxymethyloxyimino-ethylidene)-1-methyl-2-oxo-1,2-dihydroquinoxalin-3-yl]-methyl}-benzamidine-hydrochloride Yield: 56% of theory, $C_{21}H_{21}N_5O_4 \times HCl$ (407.44/443.9); mass spectrum: $(M+H)^+=408$.

(10) 4-{[6-(1-(N-methyl-N-(2-carboxy-ethyl)-aminocarbonyl)-cyclopropyl)-1-methyl-2-oxo-1,2-dihydroquinoxalin-3-yl]-methyl}-benzamidine-hydrochloride Yield: 95% of theory, $C_{25}H_{27}N_5O_4 \times HCl$ (461.53/498.0); mass spectrum: $(M+H)^+=462$;

$(M+Na)^+=484$.

(11) 4-{[6-(1-(pyrrolidin-1-yl-carbonyl)-2-carboxymethyl-ethyl)-1-methyl-2-oxo-1,2-dihydroquinoxalin-3-yl]-methyl}-benzamidine-hydrochloride Yield: 65.2% of theory, $C_{25}H_{27}N_5O_4 \times HCl$ (461.50/497.99); mass spectrum: $(M+H)^+=462$;

$(M+Na)^+=484$.

(12) 4-{[6-(1-(N-cyclopentyl-carboxymethylcarbonylamino)-cyclopropyl)-1-methyl-2-oxo-1,2-dihydroquinoxalin-3-yl]-methyl}-benzamidine-hydrochloride Yield: 54 6 of theory; $C_{28}H_{31}N_5O_4 \times HCl$ (501.59/538.06); mass spectrum: $(M+H)^+=502$;

$(M+Na)^+=524$.

(13) 4-{[7-(2-carboxyethyl-phenyl)-4-methyl-quinolin-2-yl]-oxo}-benzamidine-hydrochloride Yield: 79% of theory, $C_{26}H_{23}N_3O_3 \times HCl$ (425.49/461.95); mass spectrum: $(M+H)^+=426$;

$(M+Na)^+=448$.

(14) 4-{[7-(2-(E)-carboxyethenyl-phenyl)-4-methyl-quinolin-2-yl]-oxo}-benzamidine-hydrochloride Yield: 33% of theory, $C_{26}H_{21}N_3O_3 \times HCl$ (423.47/459.94); mass spectrum: $(M+H)^+=424$;

$(M+Na)^+=446$.

(15) 4-[7-(3-carboxymethylamino-phenyl)-4-methyl-quinolin-2-yl]-oxo}-benzamidine-hydrochloride Yield: 79% of theory, $C_{25}H_{22}N_4O_3 \times HCl$ (426.48/462.94); mass spectrum: $(M+H)^+=427$;

$(M+Na)^+=449$;

$(M+2Na)^{++}=236$.

(16) 4-{[7-(2-carboxy-2-methyl-ethyl)-4-methyl-quinolin-2-yl]-oxo}-benzamidine-hydrochloride Yield: 96% of theory, $C_{21}H_{21}N_3O_3 \times HCl$ (363.42/399.88); mass spectrum: $(M+H)^+=364$;

$(M+Na)^+=386$.

(17) 4-{[7-(4-carboxymethylaminocarbonyl-phenyl)-4-methyl-quinolin-2-yl]-oxo}-benzamidine-hydrochloride Yield: 92% of theory, $C_{26}H_{22}N_4O_4 \times HCl$ (454.49/490.96); mass spectrum: $(M+H)^+=455$.

(18) 4-[(7-carboxymethyl-4-methyl-quinolin-2-yl)-oxo]-benzamidine-hydrochloride

Yield: 75% of theory, $C_{19}H_{17}N_3O_3 \times HCl$ (335.37/371.83); mass spectrum: $(M+H)^+=336$;

$(M+Na)^+=358$.

(19) 4-{[7-(2-methyl-5-carboxymethylaminocarbonyl-phenyl)-4-methyl-quinolin-2-yl]-oxo}-benzamidine-hydrochloride Yield: 66% of theory, $C_{27}H_{24}N_4O_4 \times HCl$ (468.57/505.03); mass spectrum: $(M+H)^+=469$;

$(M+Na)^+=491$.

(20) 4-{[7-((E)-2-carboxy-1-methyl-ethenyl)-4-methyl-quinolin-2-yl]-oxo}-benzamidine-hydrochloride Yield: 75% of theory, $C_{21}H_{19}N_3O_3 \times HCl$ (361.41/397.87); mass spectrum: $(M+H)^+=362$.

(21) 4-{[7-(2-carboxy-1-methyl-ethyl)-4-methyl-quinolin-2-yl]-oxo}-benzamidine-hydrochloride Yield: 59% of theory, $C_{21}H_{21}N_3O_3 \times HCl$ (363.42/399.88); mass spectrum: $(M+H)^+=364$;

$(M+Na)^+=386$.

(22) 4-{[(7-(2-carboxymethylaminocarbonyl-1-methyl-ethyl)-4-methyl-quinolin-2-yl]-oxo}-benzamidine-hydrochloride Yield: 91% of theory, $C_{23}H_{24}N_4O_4 \times HCl$ (420.48/456.94); mass spectrum: $(M+H)^+=421$;

$(M+Na)^+=443$.

(23) 4-{[7-(1-carboxymethylaminocarbonyl-1-methyl-ethyl)-4-methyl-quinolin-2-yl]-oxo}-benzamidine-hydrochloride Yield: 96% of theory, $C_{23}H_{24}N_4O_4 \times HCl$ (420.47/456.94); mass spectrum: $(M+H)^+=421$;

$(M+Na)^+=443$.

(24) 4-{(7-(3-carboxymethyl-4,5-dihydroimidazol-2-on-1-yl)-4-methyl-quinolin-2-yl]-oxo}-benzamidine-hydrochloride Yield: 52.7% of theory, $C_{22}H_{21}N_5O_4 \times HCl$ (419.4/479.5); mass spectrum: $(M+H)^+=420$;

$(M+Na)^+=442$.

(25) 4-{[7-(N-ethyl-carboxymethylcarbonylamino)-4-methyl-quinolin-2-yl]-oxo}-benzamidine-hydrochloride Yield: 11.3% of theory, $C_{22}H_{22}N_4O_4 \times HCl$ (406.4/442.87); mass spectrum: $(M+H)^+=407$;

$(M+Na)^+=429$.

(26) 4-{[7-(N-carboxymethylaminocarbonyl-ethylamino)-4-methyl-quinolin-2-yl]-oxo}-benzamidine-hydrochloride Yield: 39.6% of theory, $C_{22}H_{23}N_5O_4 \times HCl$ (421.5/461.6); mass spectrum: $(M+H)^+=422$;

$(M+Na)^+=444$.

(27) 4-{[7-(N-(pyridin-2-yl)-N-(2-carboxy-ethyl)-aminocarbonyl)-4-methyl-quinolin-2-yl]-oxo}-benzamidine-hydrochloride Yield: 79% of theory, $C_{26}H_{23}N_5O_4 \times HCl$ (469.51/505.98); mass spectrum: $(M+H)^+=470$;

$(M+Na)^+=492$;

$(M-H+2Na)^+=514$.

(28) 4-{[7-(1-carboxymethyloxyimino-ethylidene)-4-methyl-quinolin-2-yl]-amino}-benzamidine-hydrochloride Yield: 98% of theory, $C_{21}H_{21}N_5O_3 \times HCl$ (391.44/427.9); mass spectrum: $(M+H)^+=392$;

$(M+Na)^+=414$;

$(M-H)^-=390$.

(29) 4-[(6-carboxymethyloxy-4-methyl-quinolin-2-yl)-oxo]-benzamidine-hydrochloride Yield: 59% of theory, $C_{19}H_{17}N_3O_4 \times HCl$ (351.37/387.83); mass spectrum: $(M+H)^+=352$;

$(M+Na)^+=374$.

(30) 4-{[7-(1-(2-carboxyethyl)-carbonylamino)-1-methyl-ethyl)-4-methyl-quinolin-2-yl]-oxo}-benzamidine-hydrochloride Yield: 85% of theory, $C_{24}H_{26}N_4O_4 \times HCl$ (434.5/470.97); mass spectrum: $(M+H)^+=435$;

$(M+Na)^+=457$;

$(M+K)^+=473$.

(31) 4-{[6-(N-carboxymethyl-quinolin-8-yl-sulphonylamino)-1-methyl-2-oxo-1,2-dihydroquinoxalin-3-yl]-difluoromethyl}-benzamidine-hydrochloride

(32) 2-{[6-(N-carboxymethyl-quinolin-8-yl-sulphonylamino)-1-methyl-2-oxo-1,2-dihydroquinoxalin-3-yl]-methyl}-thiophen-5-yl-amidine-hydrochloride

(33) 2-{[6-(N-carboxymethyl-quinolin-8-yl-sulphonylamino)-1-methyl-2-oxo-1,2-dihydroquinoxalin-3-yl]-methyl}-thiazol-5-yl-amidine-hydrochloride

(34) 5-{[6-(N-carboxymethyl-quinolin-8-yl-sulphonylamino)-1-methyl-2-oxo-1,2-dihydroquinoxalin-3-yl]-methyl}-pyridin-2-yl-amidine-hydrochloride

(35) 2-{[6-(N-carboxymethyl-quinolin-8-yl-sulphonylamino)-1-methyl-2-oxo-1,2-dihydroquinoxalin-3-yl]-methyl}-pyridin-5-yl-amidine-hydrochloride

(36) 4-{[6-(N-(2-carboxyethyl)-N-(2-pyridyl)-aminocarbonyl)-1-methyl-2-oxo-1,2-dihydroquinoxalin-3-yl]-methyl}-benzamidine-hydrochloride

(37) 4-{[6-(1-(2-carboxyethyl)-4-isobutyl-imidazol-5-yl)-1-methyl-2-oxo-1,2-dihydroquinoxalin-3-yl]-methyl}-benzamidine-hydrochloride

(38) 4-{[6-(N-cyclopentyl-2-carboxyethylsulphonylamino)-1-methyl-2-oxo-1,2-dihydroquinoxalin-3-yl]-methyl}-benzamidine-hydrochloride

(39) 4-{[6-(1-(2-carboxyethylamino)-1-methyl-1-(pyrrolidin-1-yl-carbonyl)-ethyl)-1-methyl-2-oxo-1,2-dihydroquinoxalin-3-yl]-methyl}-benzamidine-hydrochloride

(40) 4-{[6-(1-(N-cyclopentyl-carboxymethylcarbonylamino)-cycopropyl)-1-methyl-2-oxo-1,2-dihydroquinoxalin-3-yl]-difluoromethyl}-benzamidine-hydrochloride

(41) 2-{[(6-(1-(N-cyclopentyl-carboxymethylcarbonylamino)-cyclopropyl)-1-methyl-2-oxo-1,2-dihydroquinoxalin-3-yl]-methyl}-thiophen-5-yl-amidine-hydrochloride

(42) 2-{[6-(1-(N-cyclopentyl-carboxymethylcarbonylamino)-cyclopropyl)-1-methyl-2-oxo-1,2-dihydroquinoxalin-3-yl]-methyl}-thiazol-5-yl-amidine-hydrochloride

(43) 5-{[6-(1-(N-cyclopentyl-carboxymethylcarbonylamino)-cyclopropyl)-1-methyl-2-oxo-1,2-dihydroquinoxalin-3-yl]-methyl}-pyridin-2-yl-amidine-hydrochloride

(44) 2-{[6-(1-(N-cyclopentyl-carboxymethylcarbonylamino)-cyclopropyl)-1-methyl-2-oxo-1,2-dihydroquinoxalin-3-yl]-methyl}-pyridin-5-yl-amidine-hydrochloride

(45) 5-{[6-(1-(N-methyl-carboxymethylcarbonylaminomethyl)-1-(pyrrolidin-1-yl-carbonyl)-ethyl)-2-oxo-1,2-dihydroquinoxalin-3-yl]-methyl}-benzamidine-hydrochloride Yield: 87% of theory, $C_{29}H_{34}N_6O_5 \times HCl$ (546.63/583.09); mass spectrum: $(M+H)^+=547$;

$(M-H)^+=545$;

$(M+Na)^+=569$.

(46) 5-{[6-(1-(carboxymethylamino)-1-(pyrrolidin-1-yl-carbonyl)-ethyl)-1-methyl-2-oxo-1,2-dihydroquinoxalin-3-yl]-methyl}-benzamidine-hydrochloride Yield: % of theory; $C_{26}H_{30}N_6O_4 \times HCl$ (490.57/527.02); mass spectrum: $(M+H)^+=491$.

EXAMPLE 11

4-{[6-(2-dimethylaminoethylsulphonyl)-1-methyl-2-oxo-1,2-dihydroquinoxalin-3-yl]-methyl}-benzamidine-dihydrochloride a. [2-(4-chlorobenzenesulphonyl)-ethyl]-dimethyl-amine 50 ml of dimethylamine are placed in a pressure vessel at −50° C. and 23 g (0.1 mol) of 2-chloroethyl-(4-chlorophenyl)-sulphone are added batchwise. After 5 hours at 80° C. the reaction mixture is cooled to ambient temperature, taken up in methylene chloride, washed with water, dried and evaporated down. The residue is chromatographed on silica gel and eluted with methylene chloride/ethanol (99:1 and 98:1). The desired fractions are combined and evaporated down.

Yield: 17 g (71.5% of theory), $R_f$ value: 0.46 (silica gel; methylene chloride/ethanol=19:1).

b. [4-(2-dimethylamino-ethansulphonyl)-2-nitro-phenyl]-methyl-amine 16 ml conc. sulphuric acid are added to 8.0 g (32.4 mmol) of [2-(4-chloro-benzenesulphonyl)-ethyl]-dimethyl-amine, the reaction being strongly exothermic. Then the mixture is cooled to ambient temperature, and 6 ml conc. nitric acid are added dropwise. The reaction mixture is heated to 53° C. for 5 hours and 105° C. for 3 hours and subsequently poured onto ice water. After the addition of 150 ml methylamine solution with cooling the reaction mixture is stirred over a weekend at ambient temperature. The crystalline product is suction filtered and dried. The residue is chromatographed on silica gel and eluted with methylene chloride/ethanol (99:1). The desired fractions are combined and evaporated down.

Yield: 3.5 g (37.6% of theory), $R_f$ value: 0.28 (silica gel; methylene chloride/ethanol=19:1).

c. [4-(2-dimethylamino-ethanesulphonyl)-2-amino-phenyl]-methyl-amine

Prepared analogously to Example 1d from [4-(2-dimethylaminoethanesulphonyl)-2-nitro-phenyl]-methyl-amine and palladium on activated charcoal/hydrogen in methylene chloride/methanol.

Yield: 92.5% of theory, $R_f$ value: 0.1 (silica gel; methylene chloride/ethanol=19:1).

d. 4-{[6-(2-dimethylaminoethylsulphonyl)-1-methyl-2-oxo-1,2-dihydroquinoxalin-3-yl]-methyl}-benzonitrile Prepared analogously to Example 7f from [4-(2-dimethylaminoethane-sulphonyl)-2-amino-phenyl]-methyl-amine and 4-(2-oxo-propionic acid)-benzonitrile in ethanol.

Yield: 52% of theory, $R_f$ value: 0.65 (silica gel; methylene chloride/ethanol=19:1).

e. 4-{[6-(2-dimethylaminoethylsulphonyl)-1-methyl-2-oxo-1,2-dihydroquinoxalin-3-yl]-methyl}-benzamidine-hydrochloride Prepared analogously to Example 1f from 4-{[6-(2-dimethylaminoethylsulphonyl)-1-methyl-2-oxo-1,2-dihydroquinoxalin-3-yl]-methyl}-benzonitrile and hydrochloric acid/ammonium carbonate in ethanol.

Yield: 39% of theory, $C_{21}H_{25}N_5O_3S\times HCl$ (427,54/500.47); mass spectrum: $(M+H)^+=428$; $(M+2H)^+=214.6$.

The following compound is prepared analogously:

(1) 4-[(6-benzenesulphonyl-1-methyl-2-oxo-1,2-dihydroquinoxalin-3-yl)-methyl]-benzamidine-hydrochloride Yield: 89.8% of theory, $C_{23}H_{20}N_4O_3S\times HCl$ (432.50/468.96); mass spectrum: $(M+H)^+=433$.

EXAMPLE 12

4-{[6-(2-oxo-piperidin-1-yl)-1-methyl-2-oxo-1,2-dihydroquinoxalin-3-yl]-methyl}-benzamidine-hydrochloride a. 4-fluoro-3-nitro-N-(5-brombutyloxy)-aniline To a solution of 3.7 g (0.024 mol) of 4-fluoro-3-nitro-aniline in 100 ml tetrahydrofuran, 4.8 g (0.024 mol) of 5-bromovaleric acid chloride are added dropwise after the addition of 3 ml triethylamine at ambient temperature. Then the mixture is stirred for two hours at ambient temperature and evaporated down. The residue is chromatographed on silica gel and eluted with methylene chloride. The desired fractions are combined and concentrated by evaporation.

Yield: 7.0 g (92% of theory), $R_f$ value: 0.6 (silica gel; petroleum ether/ethyl acetate=3:7).

b. 4-(2-oxo-piperidin-1-yl)-2-nitro-fluorobenzene

To a suspension of 1.0 g (21.9 mmol) of sodium hydride (50% in oil) in 200 ml tetrahydrofuran, a solution of 7.0 g (21.9 mmol) of 4-fluoro-3-nitro-N-(5-brombutyloxy)-aniline in 50 ml tetrahydrofuran is added dropwise at ambient temperature. After 30 minutes the mixture is poured onto ice water, the tetrahydrofuran is distilled off and the aqueous phase is extracted with methylene chloride. The combined organic extracts are dried and concentrated by evaporation. The residue is chromatographed on silica gel and eluted with petroleum ether/ethyl acetate (7:3).

Yield: 4.1 g (79% of theory), $R_f$ value: 0.4 (silica gel; petroleum ether/ethyl acetate=3:7).

c. 4-(2-oxo-piperidin-1-yl)-2-nitro-N-methyl-aniline 4.1 g (0.017 mol) of 4-(2-oxo-piperidin-1-yl)-2-nitro-fluoro-benzene are stirred in 50 ml methylamine solution (40% in $H_2O$) in a sealed vessel for 1 hour at ambient temperature. Then the mixture is diluted with water, suction filtered and dried.

Yield: 3.9 g (92% of theory), $R_f$ value: 0.35 (silica gel; petroleum ether/ethyl acetate=1.9).

d. 4-(2-oxo-piperidin-1-yl)-2-amino-N-methyl-aniline

Prepared analogously to Example 1d from 4-(2-oxo-piperidin-1-yl)-2-nitro-N-methyl-aniline and palladium on activated charcoal/hydrogen in methanol.

Yield: 97% of theory, $R_f$ value: 0.25 (silica gel; methylene chloride/ethanol=19:1).

e. 4-{[6-(2-oxo-piperidin-1-yl)-1-methyl-2-oxo-1,2-dihydroquinoxalin-3-yl]-methyl}-benzonitrile Prepared analogously to Example 7f from 4-(2-oxo-piperidin-1-yl)-2-amino-N-methyl-aniline and 4-(2-oxo-propionic acid)-benzonitrile in ethanol.

Yield: 50% of theory, $R_f$ value: 0.28 (silica gel; methylene chloride/ethanol=19:1).

f. 4-{[6-(2-oxo-piperidin-1-yl)-1-methyl-2-oxo-1,2-dihydroquinoxalin-3-yl]-methyl}-benzamidine-hydrochloride Prepared analogously to Example 1f from 4-(6-(2-oxo-piperidin-1-yl)-1-methyl-2-oxo-1,2-dihydroquinoxalin-3-yl)-methyl-benzonitrile and hydrochloric acid/ammonium carbonate in ethanol.

Yield: 60% of theory, $C_{22}H_{23}N_5O_2\times HCl$ (389.5/425.9); mass spectrum: $(M+H)^+=390$.

The following compound is prepared analogously:

(1) 4-{[6-(n-butanesultam-2-yl)-1-methyl-2-oxo-1,2-dihydroquinoxalin-3-yl]-methyl}-benzamidine-hydrochloride Yield: 46% of theory, $C_{21}H_{23}N_5O_3S\times HCl$ (425.5/462.0); mass spectrum: $(M+H)^+=426$.

EXAMPLE 13

4-{[6-(1-isobutyl-tetrazol-5-yl)-1-methyl-2-oxo-1,2-dihydroquinoxalin-3-yl]-methyl}-benzamidine-hydrochloride a. 4-chloro-3-nitro-benzoic acid-isobutylamide 6 ml (0.06 mol) of isobutylamine in 60 ml tetrahydrofuran are added dropwise to a solution of 13.2 g (0.06 mol) of 4-chloro-3-nitro-benzoylchloride and 6 g (0.06 mol) of triethylamine in 150 ml tetrahydrofuran and the mixture is stirred for 1 hour. The solution is evaporated down, dissolved in methylene chloride and washed with water. The combined organic extracts are dried and evaporated down. The residue is chromatographed on silica gel and eluted with methylene chloride/ethanol (98:2). The desired fractions are combined and evaporated down.

Yield: 13.5 g (88% of theory).

b. 4-[(5-(1-isobutyl-tetrazol-5-yl)-2-nitro-chlorobenzene 10.3 g (0.04 mol) of 4-chloro-3-nitro-benzoic acid-isobutyl-amide are dissolved in 200 ml methylene chloride and mixed with 2.6 g (0.04 mol) of sodium azide. Then at 0° C. 6.7 ml (0.04 mol) of trifluoromethanesulphonic acid anhydride are added dropwise. Then the reaction mixture is stirred for 40 hours at ambient temperature and combined with 5% sodium carbonate solution. The organic phase is separated off, dried and concentrated by evaporation. The residue is chromatographed on silica gel and eluted with methylene chloride+0–1% ethanol. The desired fractions are combined and concentrated by evaporation.

Yield: 3.6 g (32% of theory), $C_{11}H_{12}ClN_5O_2$ (281.7); mass spectrum: $M^+$=281.

c. 4-[(5-(1-isobutyl-tetrazol-5-yl)-2-nitro-N-methyl-aniline

Prepared analogously to Example 12c from 4-[(5-(1-isobutyl-tetrazol-5-yl)-2-nitro-chlorobenzene and methylamine solution.

Yield: 100% of theory, $R_f$ value: 0.3 (silica gel; methylene chloride/ethanol=50:1).

d. 4-[(5-(1-isobutyl-tetrazol-5-yl)-2-amino-N-methyl-aniline

Prepared analogously to Example 1d from 4-[(5-(1-isobutyl-tetrazol-5-yl)-2-nitro-N-methyl-aniline and palladium on activated charcoal/hydrogen in methanol.

Yield: 100% of theory, $R_f$ value: 0.3 (silica gel; methylene chloride/ethanol=19:1).

e. 4-{[6-(1-isobutyl-tetrazol-5-yl)-1-methyl-2-oxo-1,2-dihydro-quinoxalin-3-yl]-methyl}-benzonitrile Prepared analogously to Example 7f from 4-[(5-(1-isobutyl-tetrazol-5-yl)-2-amino-N-methyl-aniline and 4-(2-oxo-propionic acid)-benzonitrile in ethanol.

Yield: 31% of theory, $R_f$ value: 0.53 (silica gel; methylene chloride/ethanol=19:1).

f. 4-{[6-(1-isobutyl-tetrazol-5-yl)-1-methyl-2-oxo-1,2-dihydro-quinoxalin-3-yl]-methyl}-benzamidine-hydrochloride Prepared analogously to Example 1f from 4-{[6-(1-isobutyl-tetrazol-5-yl)-1-methyl-2-oxo-1,2-dihydroquinoxalin-3-yl]-methyl}-benzonitrile and hydrochloric acid/ammonium carbonate in ethanol.

Yield: 24 % of theory, $C_{22}H_{24}N_8O\times HCl$ (416.5/452.96); mass spectrum: $(M+H)^+$=417.

EXAMPLE 14

4-[(6-phenyl-1-methyl-2-oxo-1,2-dihydroquinoxalin-3-yl)-methyl]-benzamidine-hydrochloride a. 2-nitro-4-phenyl-N-methyl-acetanilide 3.0 g (11.7 mmol) of 2-nitro-4-phenylacetanilide are dissolved in 70 ml dimethylformamide and at ambient temperature combined batchwise with 576 mg (12 mmol) of sodium hydride (50% in oil). After 30 minutes at 65° C. the reaction mixture is cooled to ambient temperature, combined with 3 ml methyl iodide and stirred for 30 minutes. The reaction mixture is stirred into saturated sodium chloride solution and extracted with ethyl acetate. The combined organic extracts are washed with water, dried and concentrated by evaporation. The residue is chromatographed on silica gel and eluted with methylene chloride+0–5% ethanol. The desired fractions are combined and concentrated by evaporation.

Yield: 3.2 g (100% of theory), $R_f$ value: 0.43 (silica gel; methylene chloride/ethanol=19:1).

b. 2-nitro-4-phenyl-N-methyl-aniline 3.2 g (11.7 mmol) of 2-nitro-4-phenyl-N-methyl-acetanilide are refluxed in 99 ml semiconcentrated hydrochloric acid for 7 hours. The solution is cooled and extracted with methylene chloride. The organic phase is washed with water and sodium hydrogen carbonate solution, dried over sodium sulphate and concentrated by evaporation. The residue is chromatographed on silica gel and eluted with methylene chloride. The desired fractions are combined and concentrated by evaporation.

Yield: 2.0 g (75% of theory), $R_f$ value: 0.8 (silica gel; methylene chloride).

c. 2-amino-4-phenyl-N-methyl-aniline

Prepared analogously to Example 1d from 2-nitro-4-phenyl-N-methyl-aniline and palladium on activated charcoal/hydrogen in methanol.

Yield: 91% of theory, $R_f$ value: 0.4 (silica gel; methylene chloride/ethanol=19:1).

d. 4-[(6-phenyl-1-methyl-2-oxo-1,2-dihydroquinoxalin-3-yl)-methyl]-benzonitrile

Prepared analogously to Example 7f from 2-amino-4-phenyl-N-methyl-aniline and 4-(2-oxo-propionic acid)-benzonitrile in ethanol.

Yield: 44% of theory, $R_f$ value: 0.76 (silica gel; methylene chloride/ethanol=19:1).

e. 4-[(6-phenyl-1-methyl-2-oxo-1,2-dihydroquinoxalin-3-yl)-methyl]-benzamidine-hydrochloride Prepared analogously to Example 1f from 4-[(6-phenyl-1-methyl-2-oxo-1,2-dihydroquinoxalin-3-yl)-methyl]-benzonitrile and hydrochloric acid/ammonium carbonate in ethanol.

Yield: 63% of theory, $C_{23}H_{20}N_4O\times HCl$ (368.4/404.9); mass spectrum: $(M+H)^+$=369.

The following compound is prepared analogously:

(1) 4-{[6-(2-methyl-phenyl)-1-methyl-2-oxo-1,2-dihydroquinoxalin-3-yl]-methyl}-benzamidine-hydrochloride Yield: 80% of theory, $C_{24}H_{22}N_4O\times HCl$ (382.47/418.94); mass spectrum: $(M+H)^+$=383.

EXAMPLE 15

4-{[6-(N-(2-ethoxycarbonylethyl)-N-isobutyl-aminocarbonyl)-1-methyl-2-oxo-1,2-dihydroquinoxalin-3-yl]-methyl}-benzamidine-hydrochloride a. Ethyl 3-isobutylamino-propionate 7.7 g (0.05 mol) of β-alanine ethylester-hydrochloride, 3.6 g (0.05 mol) of isobutyraldehyde, 5.1 g (0.05 mol) of triethylamine and 3 g palladium on activated charcoal are dissolved in 200 ml ethanol and hydrogenated under hydrogen pressure. The catalyst is suction filtered and the filtrate evaporated down. The residue is digested with ether, suction filtered and dried.

Yield: 9.3 g (100% of theory) contaminated with triethylamine-hydrochloride.

Ethyl 3-N-[isobutyl-(4-methylamino-3-nitro-benzoyl)-amino]-propionate 4.5 g (25.9 mmol) of ethyl 3-isobutylamino-propionate are suspended in 100 ml tetrahydrofuran and 5 ml triethylamine and after the addition of 3.3 g (15.3 mmol) of 4-amino-3-nitro-benzoylchloride stirred overnight at ambient temperature. The tetrahydrofuran is distilled off in vacuo, the residue dissolved in methylene chloride and extracted with water. The organic phase is dried and evaporated down. The residue is chromatographed on silica gel and eluted with methylene chloride+1–5% ethanol.

Yield: 4.7 g (87% of theory), $R_f$ value: 0.32 (silica gel; methylene chloride/ethanol=50:1).

c. Ethyl 3-N-[isobutyl-(4-methylamino-3-amino-benzoyl)-amino]-propionate

Prepared analogously to Example 1d from ethyl 3-N-[isobutyl-(4-methylamino-3-nitro-benzoyl)-amino]-propionate and palladium on activated charcoal/hydrogen in ethanol/methylene chloride.

Yield: 100% of theory, $R_f$ value: 0.78 (silica gel; methylene chloride/ethanol=19:1).

d. 4-{[6-(N-(2-ethoxycarbonylethyl)-N-isobutyl-aminocarbonyl)-1-methyl-2-oxo-1,2-dihydroquinoxalin-3-yl]-methyl}-benzonitrile Prepared analogously to Example 7f from ethyl-3-[isobutyl-(4-methylamino-3-amino-benzoyl)-amino]-propionate and 4-(2-oxo-propionic acid)-benzonitrile in ethanol.

Yield: 34% of theory, e. 4-{[6-(N-(2-ethoxycarbonylethyl)-N-isobutyl-aminocarbonyl)-1-methyl-2-oxo-1,2-dihydroquinoxalin-3-yl]-methyl}-benzamidine-hydrochloride Prepared analogously to Example 1f from 4-(6-(N-2-ethoxycarbonyl-ethyl-N-isobutyl)aminocarbonyl-1-methyl-2-oxo-1,2-dihydroquinoxalin-3-yl)-methyl-benzonitrile and hydrochloric acid/ammonium carbonate in ethanol.

Yield: 71% of theory, $C_{27}H_{35}N_5O_4 \times HCl$ (491.6/528.07); mass spectrum: $(M+H)^+=492$;

$(M+H+Na)^+=257.7$.

The following compounds are prepared analogously:

(1) 4-{[6-(N-(2-ethoxycarbonylethyl)-N-phenyl-aminocarbonyl)-1-methyl-2-oxo-1,2-dihydroquinoxalin-3-yl]-methyl}-benzamidine-hydrochloride Yield: 85% of theory, $C_{29}H_{29}N_5O_4 \times HCl$ (511.59/548.06); mass spectrum: $(M+H)^+=512$;

$(M+H+Na)^{++}=267.8$.

(2) 4-{[6-(N-(2-(1H-tetrazol-5-yl)ethyl)-N-phenyl-aminocarbonyl)-1-methyl-2-oxo-1,2-dihydroquinoxalin-3-yl]-methyl}-benzamidine-hydrochloride Yield: 37% of theory, $C_{27}H_{25}N_9O_2 \times HCl$ (507.6/544.0); mass spectrum: $(M+H)^+=508$.

(3) 4-{[6-(N-ethoxycarbonylmethyl-N-(pyridin-2-yl)-aminocarbonyl-1-methyl-2-oxo-1,2-dihydroquinoxalin-3-yl]-methyl}-benzamidine-hydrochloride Yield: 84% of theory, $C_{27}H_{26}N_6O_4 \times HCl$ (498.55/535.02); mass spectrum: $(M+H)^+=499$.

(4) 4-{[6-(N-(2-ethoxycarbonylethyl)-N-(pyridin-2-yl)-aminocarbonyl-1-methyl-2-oxo-1,2-dihydroquinoxalin-3-yl]-methyl}-benzamidine-hydrochloride Yield: 50% of theory, $C_{28}H_{28}N_6O_4 \times HCl$ (512.58/549.04); mass spectrum: $(M+H)^+=513$.

EXAMPLE 16

4-{[6-(N-ethoxycarbonylmethyl-quinolin-8-yl-sulphonylamino)-1-methyl-2-oxo-1,2-dihydroquinoxalin-3-yl]-methyl}-N'-(2-methylsulphonyl-ethyloxycarbonyl)-benzamidine 0.5 g (0.77 mmol) of 4-{[6-(N-ethoxycarbonylmethyl-quinolin-8-yl-sulphonylamino)-1-methyl-2-oxo-1,2-dihydroquinoxalin-3-yl]-methyl}-benzamidine-hydrochloride, 0.32 g (2.3 mmol) of potassium carbonate and 0.39 g (1.4 mmol) of 2-(methylsulphonyl)-ethyl-4-nitrophenyl carbonate are stirred in 40 ml tetrahydrofuran for 54 hours at ambient temperature. The solvent is distilled off and the residue is taken up in methylene chloride and sodium hydrogen carbonate solution. The combined organic extracts are dried and evaporated down. The residue is chromatographed on aluminium oxide and eluted with methylene chloride+1–5% ethanol.

Yield: 180 mg (31.8% of theory), $C_{34}H_{34}N_6O_9S_2$ (734.80); mass spectrum: $(M+H)^+=735$;

$(M+Na)^+=757$.

EXAMPLE 17

4-{[6-(N-cyclopentyl-3-carboxypropionylamino)-1-methyl-2-oxo-1,2-dihydroquinoxalin-3-yl]-methyl}-benzamidine-hydrochloride 400 mg (0.74 mmol) of 4-{[6-(N-cyclopentyl-3-ethoxycarbonyl-propionylamino)-1-methyl-2-oxo-1,2-dihydroquinoxalin-3-yl]-methyl}-benzamidine-hydrochloride are stirred for 6 hours at ambient temperature in 15 ml of semiconcentrated hydrochloric acid. Then the mixture is evaporated down in vacuo and dried over phosphorus pentoxide in a high vacuum.

Yield: 400 mg (98.5% of theory), $C_{26}H_{29}N_5O_4 \times HCl$ (475.56/512.02); mass spectrum: $(M+H)^+=476$;

$(M+Na)^+=498$.

The following compounds are prepared analogously:

(1) 4-{[6-(1-(2-carboxy-piperidin-1-yl-carbonyl)-cyclopropyl)-1-methyl-2-oxo-1,2-dihydroquinoxalin-3-yl]-methyl}-benzamidine-hydrochloride Yield: 70.2% of theory, $C_{27}H_{29}N_5O_4 \times HCl$ (487.56/524.03); mass spectrum: $(M+H)^+=488$;

$(M+Na)^+=510$.

(2) 4-{[6-(1-(N-cyclopentyl-3-carboxypropionylamino)-cyclopropyl-1-methyl-2-oxo-1,2-dihydroquinoxalin-3-yl]-methyl}-benzamidine-hydrochloride Yield: 100% of theory, $C_{29}H_{34}N_5O_4 \times HCl$ (515.62/552.08); mass spectrum: $(M+H)^+=516$;

$(M+Na)^+=538$.

(3) 4-{[6-(1-(2-carboxymethylaminocarbonyl-pyrrolidin-1-yl-carbonyl)-cyclopropyl)-1-methyl-2-oxo-1,2-dihydroquinoxalin-3-yl]-methyl}-benzamidine-hydrochloride Yield: 91.8% of theory, $C_{28}H_{30}N_6O_5 \times HCl$ (530.59/567.05); mass spectrum: $(M+H)^+=531$;

$(M+Na)^+=553$.

(4) 4-{[6-(1-(2-(2-carboxyethyl)aminocarbonyl)-pyrrolidin-1-yl-carbonyl)-cyclopropyl)-1-methyl-2-oxo-1,2-dihydroquinoxalin-3-yl]-methyl}-benzamidine-hydrochloride Yield: 99.2% of theory, $C_{29}H_{32}N_6O_5 \times HCl$ (544.62/581.09); mass spectrum: $(M+H)^+=545$;

$(M+Na)^+=567$.

(5) 4-{[6-(1-(2-carboxymethyl-piperidin-1-yl-carbonyl)-cyclopropyl)-1-methyl-2-oxo-1,2-dihydroquinoxalin-3-yl]-methyl}-benzamidine-hydrochloride Yield: 88.4% of theory, $C_{28}H_{31}N_5O_4 \times HCl$ (501.59/538.05); mass spectrum: $(M+H)^+=502$;

$(M+Na)^+=524$.

(6) 4-{[6-(1-(2-carboxymethylaminocarbonyl-pyrrolidin-1-yl-carbonyl)-cyclopropyl)-1-methyl-2-oxo-1,2-dihydroquinoxalin-3-yl]-carbonyl}-benzamidine-hydrochloride Yield: 75.9% of theory, $C_{28}H_{28}N_6O_6 \times HCl$ (544.57/581.04); mass spectrum: $(M+H)^+=545$;

$(M+Na)^+=567$.

(7) 4-{[6-(4-(1-(2-carboxy-ethyl)-piperidin-1-yl-carbonyl)-cyclopropyl)-1-methyl-2-oxo-1,2-dihydroquinoxalin-3-yl]-methyl}-benzamidine-hydrochloride Yield: 80.1% of theory, $C_{29}H_{33}N_5O_4 \times HCl$ (515.62/552.09); mass spectrum: $(M+H)^+=516$.

EXAMPLE 18

4-{[6-(1-ethoxycarbonylmethyl-4-isobutyl-imidazol-5-yl)-1-methyl-2-oxo-1,2-dihydroquinoxalin-3-yl]-methyl}-benzamidine-hydrochloride a. 1-(4-chloro-phenyl)-4-methyl-pentan-1-one A solution of 56 g (0.42 mol) of isocaproic acid chloride in 20 ml chlorobenzene is added dropwise to a suspension of 66.7 g (0.5 mol) of aluminium chloride in 300 ml chlorobenzene. The solution is stirred for 3 hours at 50° C. and subsequently evaporated down. The residue is carefully poured onto ice water, acidified with hydrochloric acid and extracted with ethyl acetate. The organic phases are washed with water, dried and evaporated down and the residue obtained is chromatographed on silica gel with petroleum ether/methylene chloride (2:8).

Yield: 72.5 g (83% of theory), $R_f$ value: 0.6 (silica gel; methylene chloride).

b. 2-bromo-1-(4-chlorophenyl)-4-methyl-pentan-1-one 55 g (0.344 mol) of bromine are added dropwise to a solution of 72.5 g (0.344 mol) of 1-(4-chlorophenyl)-4-methyl-pentan-1-one in 300 ml dioxane and 300 ml methylene chloride in such a way that decolorisation sets in immediately. After 10 minutes at ambient temperature the solvent is evaporated off.

Yield: 99 g (100% of theory), $R_f$ value: 0.76 (silica gel; methylene chloride).

c. 5-(4-chlorophenyl)-4-isobutyl-1H-imidazole 38 g (0.43 mol) of 2-bromo-1-(4-chlorophenyl)-4-methyl-pentan-1-one are heated to 160° C. in 400 ml formamide for 10 hours. After 12 hours at ambient temperature the mixture is diluted with water and combined with ammonia. The precipitate formed is filtered off, then washed with water and ether.

Yield: 19 g (66% of theory), $R_f$ value: 0.5 (silica gel; methylene chloride/methanol=9:1).

d. ethyl [5-(4-chlorophenyl)-4-isobutyl-imidazol-1-yl]-acetate 19 g (0.085 mol) of 5-(4-chlorophenyl)-4-isobutyl-1H-imidazol are dissolved in 500 ml acetone and after the addition of 41.5 g (0.3 mol) of potassium carbonate and 16.7 g (0.13 mol) of ethyl bromoacetate the mixture is refluxed for 16 hours. Then the insoluble matter is filtered off and the mother liquor is evaporated down. The residue is chromatographed on silica gel and eluted with methylene chloride/methanol (80:1). The desired fractions are combined and evaporated down.

Yield: 5.4 g (20% of theory), $R_f$ value: 0.54 (silica gel; methylene chloride/methanol=9:1).

e. [5-(4-chlorophenyl)-4-isobutyl-imidazol-1-yl]-acetic acid 4.8 g (0.015 mol) of ethyl [5-(4-chlorophenyl)-4-isobutyl-imidazol-1-yl]-acetate are dissolved in 15 ml ethanol and 40 ml water and after the addition of 2.0 g (0.05 mol) of sodium hydroxide stirred for 2 hours at ambient temperature. The alcohol is distilled off, the residue is diluted with water and adjusted to pH 5 with hydrochloric acid. The precipitate formed is filtered off, washed with water and dried.

Yield: 3.9 g (89% of theory), $R_f$ value: 0.38 (silica gel; methylene chloride/methanol=5:1).

f. [5-(4-chloro-3-nitro-phenyl)-4-isobutyl-imidazol-1-yl]-acetic acid

Prepared analogously to Example 1b from [5-(4-chlorophenyl)-4-isobutyl-imidazol-1-yl]-acetic acid and fuming nitric acid at −15° C.

Yield: 75% of theory, $R_f$ value: 0.4 (silica gel; methylene chloride/methanol=5:1).

g. [4-isobutyl-5-(4-methylamino-3-nitro-phenyl)-imidazol-1-yl]-acetic acid

Prepared analogously to Example 7a from [5-(4-chloro-3-nitro-phenyl)-4-isobutyl-imidazol-1-yl]-acetic acid and methylamine solution (40%) at 110° C.

Yield: 99% of theory, $R_f$ value: 0.42 (reversed phase RP 18; methanol/5% saline solution=6:4).

h. Ethyl [4-isobutyl-5-(4-methylamino-3-nitro-phenyl)-imidazol-1-yl]-acetate 100 ml of absolute ethanol is saturated with hydrogen chloride and, after the addition of 3.6 g (0.011 mol) of [4-isobutyl-5-(4-methylamino-3-nitro-phenyl)-imidazol-1-yl]-acetic acid, stirred for 3 hours at ambient temperature. The solution is evaporated down in vacuo, the residue is dissolved in water, made basic with ammonia and extracted with ethyl acetate. The combined organic extracts are dried and evaporated down.

Yield: 2.9 g (73% of theory), $R_f$ value: 0.64 (silica gel; methylene chloride/methanol=9:1).

i. Ethyl [4-isobutyl-5-(4-methylamino-3-amino-phenyl)-imidazol-1-yl]-acetate

Prepared analogously to Example 1d from ethyl [4-isobutyl-5-(4-methylamino-3-nitro-phenyl)-imidazol-1-yl]-acetate and palladium on activated charcoal/hydrogen in methanol.

Yield: 79% of theory, $R_f$ value: 0.44 (silica gel; methylene chloride/methanol=9:1).

k. 4-{[6-(1-ethoxycarbonylmethyl-4-isobutyl-imidazol-5-yl)-1-methyl-2-oxo-1,2-dihydroauinoxalin-3-yl]-methyl-benzonitrile Prepared analogously to Example 7f from ethyl [4-isobutyl-5-(4-methylamino-3-amino-phenyl)-imidazol-1-yl]-acetate and 4-(2-oxo-propionic acid)-benzonitrile in ethanol.

Yield: 59% of theory, $R_f$ value: 0.58 (silica gel; methylene chloride/methanol=9:1).

l. 4-{[6-(1-ethoxycarbonylmethyl-4-isobutyl-imidazol-5-yl)-1-methyl-2-oxo-1,2-dihydroquinoxalin-3-yl]-methyl}-benzamidine-hydrochloride Prepared analogously to Example 1f from 4-{[6-(1-ethoxycarbonylmethyl-4-isobutyl-imidazol-5-yl)-1-methyl-2-oxo-1,2-dihydro-quinoxalin-3-yl]-methyl}-benzonitrile and hydrochloric acid/ammonium carbonate in ethanol.

Yield: 68% of theory, $C_{28}H_{32}N_6O_3 \times HCl$ (500.61/537.07); mass spectrum: $(M+H)^+=501$.

EXAMPLE 19

4-{[6-(N-ethoxycarbonylmethyl-quinolin-8-yl-sulphonylamino)-1-methyl-2-oxo-1,2-dihydroquinoxalin-3-yl]-methyl}-N'-(methylcarbonyloxy(methyl)methyleneoxycarbonyl)-benzamidine a. (1-chloroethyl-4-nitrophenyl) carbonate To a solution of 12.6 g (90 mmol) of p-nitrophenol in 300 ml methylene chloride and 7.2 g (91 mmol) of pyridine, 14.2 g (99 mmol) of 1-chloroethyl chlorformate are added dropwise at −10° C. The solution is stirred for 72 hours at ambient temperature and subsequently extracted with water and 0.5% sodium hydroxide solution. The combined organic extracts are dried and evaporated down. The residue is chromatographed on aluminium oxide and eluted with methylene chloride. The combined fractions are evaporated down, triturated with petroleum ether and suction filtered.

Yield: 7.3 g (33% of theory), $R_f$ value: 0.58 (silica gel; ethyl acetate/petroleum ether=3:7).

b. 1-(4-nitro-phenoxycarbonyloxy)-ethyl acetate 7.2 g (29.3 mmol) of (1-chloroethyl-4-nitrophenyl)-carbonate and 10.9 g (34.2 mmol) of mercury (II)-acetate are stirred in 200 ml glacial acetic acid for 16 hours at ambient temperature. Then the mixture is evaporated to dryness, the residue is chromatographed on silica gel and extracted with methylene chloride.

Yield: 4.2 g (53% of theory), $R_f$ value: 0.48 (silica gel; methylene chloride).

c. 4-[{[6-(N-ethoxycarbonylmethyl-quinolin-8-yl-sulphonylamino)-1-methyl-2-oxo-1,2-dihydroquinoxalin-3-yl]-methyl}-N'-(methylcarbonyloxy(methyl)methylenoxycarbonyl)-benzamidine 360 mg (0.56 mmol) of 4-{[6-(N-ethoxycarbonylmethyl-quinolin-8-yl-sulphonylamino)-1-methyl-2-oxo-1,2-dihydroquinoxalin-3-yl]-methyl}-benzamidine-hydrochloride, 270 mg (1.0 mmol) of 1-(4-nitro-phenoxycarbonyloxy)-ethyl acetate, 0.17 ml (1.0 mmol) of N-ethyl-diisopropylamine and 25 ml methylene chloride are stirred for 5 hours at ambient temperature. The solvent is distilled off, the residue is chromatographed on aluminium oxide and eluted with methylene chloride+0–2% ethanol. The desired fractions are combined and evaporated down.

Yield: 260 mg (65% of theory), $C_{35}H_{34}N_6O_9S$ (714.76); mass spectrum: $(M+H)^+=715$;

$(M+Na)^+=737$.

EXAMPLE 20

4-{[6-(N-cyclopentyl-N-(2-ethoxycarbonylethylsulphonyl)-amino)-1-methyl-2-oxo-1,2-dihydroquinoxalin-3-yl]-methyl}-benzamidine-hydrochloride a. Cyclopentyl-(4-fluoro-3-nitro-phenyl)-amine 6.7 g (0.08 mol) of cyclopentanone, 12.5 g (0.08 mol) of 4-fluoro-3-nitro-aniline and 30 ml (0.1 mol) of titanium-IV-isopropoxide are stirred for 30 minutes at 40° C. and one hour at ambient temperature. After the addition of 150 ml of ethanol the reaction mixture is stirred for 30 minutes and subsequently combined batchwise with 2.4 g (0.066 mol) of sodium borohydride. After 4 hours the reaction mixture is poured onto ice water and combined with ethyl acetate. After filtration the organic phase is separated off, dried and evaporated down. The residue is chromatographed on silica gel and eluted with petroleum ether/ethyl acetate (9:1). The desired fractions are combined and evaporated down.

Yield: 8.8 g (49% of theory), $R_f$ value: 0.68 (silica gel; petroleum ether/ethyl acetate=4:1).

b. N-cyclopentyl-(4-N-methylamino-2-nitrophenyl)-amine

Prepared analogously to Example 7a from cyclopentyl-(4-fluoro-3-nitrophenyl)-amine and methylamine solution.

Yield: 100% of theory, $R_f$ value: 0.44 (silica gel; methylene chloride).

c. Methyl 3-[cyclopentyl-(4-methylamino-3-nitro-phenyl)-sulphamoyl]-propionate

Prepared analogously to Example 1e from cyclopentyl-(4-N-methyl-2-nitro-phenyl)-amine and methyl 3-chlorosulphonyl-propionate in pyridine.

Yield: 36% of theory, $R_f$ value: 0.45 (silica gel; methylene chloride/ethanol=50:1).

d. Methyl 3-[cyclopentyl-(3-amino-4-methylamino-phenyl)-sulphamoyl]-propionate

Prepared analogously to Example 1d from methyl 3-[cyclopentyl-(4-methyl-amino-3-nitro-phenyl)-sulphamoyl]-propionate and palladium on activated charcoal/hydrogen in methylene chloride/methanol.

Yield: 100% of theory, $R_f$ value: 0.52 (silica gel; methylene chloride/ethanol=50:1).

e. 4-{[6-(N-cyclopentyl-N-(2-ethoxycarbonylethylsulphonyl)-amino)-1-methyl-2-oxo-1,2-dihydroquinoxalin-3-yl]-methyl}-benzonitrile Prepared analogously to Example 7f from methyl 3-[cyclopentyl-(3-amino-4-methylamino-phenyl)-sulphamoyl]-propionate and 3-(4-cyano-phenyl)-2-oxo-propionic acid in ethanol.

Yield: 51% of theory, $R_f$ value: (silica gel; ethyl acetate/petroleum ether=3:1).

f. 4-{[6-(N-cyclopentyl-N-(2-ethoxycarbonylethylsulphonyl)-amino)-1-methyl-2-oxo-1,2-dihydroquinoxalin-3-yl]-methyl}-benzamidine-hydrochloride Prepared analogously to Example 1f from 4-{[6-(N-cyclopentyl-N-(2-ethoxycarbonylethylsulphonyl)-amino)-1-methyl-2-oxo-1,2-dihydroquinoxalin-3-yl]-methyl}-benzonitrile and hydrochloric acid/ammonium carbonate in ethanol.

Yield: 51% of theory, $C_{27}H_{33}N_5O_5S \times HCl$ (539.67/576.13); mass spectrum: $(M+H)^+=540$.

The following compounds are prepared analogously:

(1) 4-{[6-(N-(3-ethoxycarbonylpropionyl)-N-cyclopentyl-amino)-1-methyl-2-oxo-1,2-dihydroquinoxalin-3-yl]-methyl}-benzamidine-hydrochloride Yield: 83% of theory, $C_{28}H_{33}N_5O_4 \times HCl$ (503.61/540.08); mass spectrum: $(M+H)^+=504$;

$(M+H+Na)^{++}=263.7$.

(2) 4-{[6-(N-(2-ethoxycarbonylmethylcarbonyl)-N-cyclopentyl-amino)-1-methyl-2-oxo-1,2-dihydroquinoxalin-3-yl]-methyl}-benzamidine-hydrochloride Yield: 53% of theory, $C_{27}H_{31}N_5O_4 \times HCl$ (489.59/526.54); mass spectrum: $(M+H)^+=490$.

(3) 4-{[6-(N-cyclopentyl-ethoxycarbonylmethylsulphonylamino)-1-methyl-2-oxo-1,2-dihydroquinoxalin-3-yl]-methyl}-benzamidine-hydrochloride Yield: 87% of theory, $C_{26}H_{31}N_5O_5S \times HCl$ (525.64/562.11); mass spectrum: $(M+H)^+=526$.

(4) 4-{[6-(N-cyclopentyl-N-(tetrazol-5-yl-methylcarbonyl)-amino-1-methyl-2-oxo-1,2-dihydroquinoxalin-3-yl]-methyl}-benzamidine-hydrochloride Yield: 19% of theory, $C_{25}H_{27}N_9O_2 \times HCl$ (485.56/522.03); mass spectrum: $(M+H)^+=486$;

$(M+Na)^+=508$.

EXAMPLE 21

4-{[6-(1-ethoxycarbonyl-cyclohexan-1-yl)-1-methyl-2-oxo-1,2-dihydroquinoxalin-3-yl]-methyl}-benzamidine-hydrochloride a. 1-(4-chloro-3-nitrophenyl)-cyclohexanecarboxylic acid Prepared analogously to Example 1b from 1-(4-chlorophenyl)-cyclohexanecarboxylic acid and fuming nitric acid at −25° C.

Yield: 88.2% of theory.

b. 1-(4-methylamino-3-nitrophenyl)-cyclohexanecarboxylic acid

Prepared analogously to Example 7a from 1-(4-chloro-3-nitrophenyl)-cyclohexanecarboxylic acid and methylamine solution.

Yield: 90.6% of theory, $R_f$ value: 0.27 (silica gel; methylene chloride/ethanol=95:5).

c. ethyl 1-(4-methylamino-3-nitrophenyl)-cyclohexanecarboxylate

Prepared analogously to Example 18h from 1-(4-methylamino-3-nitrophenyl)-cyclohexanecarboxylic acid and ethanolic hydrochloric acid.

Yield: 87% of theory, $R_f$ value: 0.82 (silica gel; methylene chloride/ethanol=95:5).

d. ethyl 1-(3-amino-4-methylamino-phenyl)-cyclohexanecarboxylate

Prepared analogously to Example id from ethyl 1-(4-methyl-amino-3-nitrophenyl)-cyclohexanecarboxylate and palladium on activated charcoal/hydrogen in methanol/methylene chloride.

Yield: 100% of theory.

e. 4-[(6-(1-ethoxycarbonyl)cyclohexan-1-yl-1-methyl-2-oxo-1,2-dihydropuinoxalin-3-yl)-methyl]-benzonitrile Prepared analogously to Example 7f from ethyl 1-(3-amino-4-methylamino-phenyl)-cyclohexanecarboxylate and 3-(4-cyanophenyl)-2-oxo-propionic acid in ethanol.

Yield: 57.1% of theory.

f. 4-{[6-(1-ethoxycarbonyl-cyclohexan-1-yl)-1-methyl-2-oxo-1,2-dihydropuinoxalin-3-yl]-methyl}-benzamidine-hydrochloride Prepared analogously to Example 1f from 4-{[(-(1-ethoxycarbonyl-cyclohexan-1-yl)-1-methyl-2-oxo-1,2-dihydroquinoxalin-3-yl]-methyl}-benzonitrile and hydrochloric acid/ammonium carbonate in ethanol.

Yield: 84.6% of theory, $C_{26}H_{30}N_4O_3 \times HCl$ (446.55/483.01); mass spectrum: $M^+$=446.

The following compounds are prepared analogously:

(1) 4-{[6-(1-ethoxycarbonyl-1-methyl-ethyl)-1-methyl-2-oxo-1,2-dihydroquinoxalin-3-yl]-methyl}-benzamidine-hydrochloride Yield; 63% of theory, $C_{23}H_{26}N_4O_3 \times HCl$ (406.48/442.94); mass spectrum: $(M+H)^+$=407.

(2) 4-{[6-(1-ethoxycarbonyl-cyclopropyl)-1-methyl-2-oxo-1,2-dihydroquinoxalin-3-yl]-methyl}-benzamidine-hydrochloride Yield: 31.6% of theory, $C_{23}H_{24}N_4O_3 \times HCl$ (404.48/477.41); mass spectrum: $M^+$=404.

(3) 4-{[6-(1-ethoxycarbonylmethylaminocarbonyl-1-methyl-ethyl)-1-methyl-2-oxo-1,2-dihydroquinoxalin-3-yl]-methyl}-benzamidine-hydrochloride Yield: 78% of theory, $C_{25}H_{29}N_5O_4 \times HCl$ (463.55/536.48); mass spectrum: $M^+$=463.

(4) 4-{[6-(1-ethoxycarbonylmethylaminocarbonyl-cyclopropyl)-1-methyl-2-oxo-1,2-dihydroquinoxalin-3-yl]-methyl}-benzamidine-hydrochloride Yield: 55% of theory, $C_{25}H_{27}N_5O_4 \times HCl$ (461.53/534.46); mass spectrum: $M^+$=461.

(5) 4-{[6-(1-(N-methyl-ethoxycarbonylmethylaminocarbonyl)-cyclopropyl)-1-methyl-2-oxo-1,2-dihydroquinoxalin-3-yl]-methyl}-benzamidine-hydrochloride Yield: 80.6% of theory, $C_{26}H_{29}N_5O_4 \times HCl$ (475.56/512.02); mass spectrum: $(M+H)^+$=476.

(6) 4-{[6-(1-(N-methyl-ethoxycarbonylmethylaminocarbonyl)-1-methyl-ethyl)-1-methyl-2-oxo-1,2-dihydroquinoxalin-3-yl]-methyl}-benzamidine-hydrochloride Yield: 79% of theory, $C_{26}H_{31}N_5O_4 \times HCl$ (477.57/514.04); mass spectrum: $(M+H)^+$=478.

(7) 4-{[6-(1-methyl-1-(piperidin-1-yl-carbonyl)-ethyl)-1-methyl-2-oxo-1,2-dihydroquinoxalin-3-yl]-methyl}-benzamidine-hydrochloride Yield: 89% of theory, $C_{26}H_{31}N_5O_2 \times HCl$ (445.57/482.04); mass spectrum: $(M+H)^+$=446.

(8) 4-{[6-(1-methyl-1-(pyrrolidin-1-yl-carbonyl)-ethyl)-1-methyl-2-oxo-1,2-dihydroquinoxalin-3-yl]-methyl}-benzamidine-hydrochloride Yield: 69% of theory, $C_{25}H_{29}N_5O_2 \times HCl$ (431.55/468.01); mass spectrum: $(M+H)^+$=432.

(9) 4-{[6-(1-methyl-1-dimethylaminocarbonyl-ethyl)-1-methyl-2-oxo-1,2-dihydroquinoxalin-3-yl]-methyl}-benzamidine-hydrochloride Yield: 92% of theory, $C_{23}H_{27}N_5O_2 \times HCl$ (405.51/441.97); mass spectrum: $(M+H)^+$=406.

(10) 4-{[6-(1-methyl-1-(piperazin-1-yl-carbonyl)-ethyl)-1-methyl-2-oxo-1,2-dihydroquinoxalin-3-yl]-methyl}-benzamidine-dihydrochloride Yield: 59% of theory, $C_{25}H_{30}N_6O_2 \times HCl$ (446.56/483.03); mass spectrum: $(M+H)^+$=447.

(11) 4-{[6-(1-(N-(2-ethoxycarbonyl-ethyl)-N-methyl-aminocarbonyl)-cyclopropyl)-1-methyl-2-oxo-1,2-dihydroquinoxalin-3-yl]-methyl}-benzamidine-hydrochloride Yield: 66% of theory, $C_{27}H_{31}N_5O_4 \times HCl$ (489.58/526.04); mass spectrum: $(M+H)^+$=490;

$(M+H+Na)^{++}$=256.6.

(12) 4-{[6-(1-(4-methyl-piperidin-1-yl-carbonyl)-cyclopropyl)-1-methyl-2-oxo-1,2-dihydroquinoxalin-3-yl]-methyl}-benzamidine-hydrochloride Yield: 89.2% of theory, $C_{27}H_{31}N_5O_2 \times HCl$ (457.58/494.05); mass spectrum: $(M+H)^+$=458.

(13) 4-{[6-(1-(pyrrolidin-1-yl-carbonyl)-cyclopropyl)-1-methyl-2-oxo-1,2-dihydroquinoxalin-3-yl]-methyl}-benzamidine-hydrochloride Yield: 33.2% of theory, $C_{25}H_{27}N_5O_2 \times HCl$ (429.56/466.0); mass spectrum: $(M+H)^+$=430.

(14) 4-{[6-(1-(4-methyl-piperazin-1-yl-carbonyl)-cyclopropyl)-1-methyl-2-oxo-1,2-dihydroquinoxalin-3-yl]-methyl}-benzamidine-dihydrochloride Yield: 80.2% of theory, $C_{26}H_{30}N_6O_2 \times HCl$ (458.56/495.03); mass spectrum: $(M+H)^+$=459;

$(M+2H)^{++}$=230.

(15) 4-{[6-(1-(3-methyl-piperidin-1-yl-carbonyl)-cyclopropyl)-1-methyl-2-oxo-1,2-dihydroquinoxalin-3-yl]-methyl}-benzamidine-hydrochloride Yield: 77.2% of theory, $C_{27}H_{31}N_5O_2 \times HCl$ (457.58/494.05); mass spectrum: $(M+H)^+$=458;

$(M+Na)^+$=480.

(16) 4-{[6-(1-(2-ethoxycarbonyl-piperidin-1-yl-carbonyl)-cyclopropyl)-1-methyl-2-oxo-1,2-dihydroquinoxalin-3-yl]-methyl}-benzamidine-hydrochloride Yield: 79% of theory, $C_{29}H_{33}N_5O_4 \times HCl$ (515.61/552.07); mass spectrum: $(M+H)^+$=516.

(17) 4-{[6-(1-(2-ethoxycarbonyl-pyrrolidin-1-yl-carbonyl)-cyclopropyl)-1-methyl-2-oxo-1,2-dihydroquinoxalin-3-yl]-methyl}-benzamidine-hydrochloride Yield: 48.1% of theory, $C_{28}H_{31}N_5O_4 \times HCl$ (501.59/538.06); mass spectrum: $(M+H)^+$=502;

$(M+H+Na)^{++}$=262.8.

(18) 4-{[6-(1-(2,3-dihydroindol-1-yl-carbonyl)-cyclopropyl)-1-methyl-2-oxo-1,2-dihydroquinoxalin-3-yl]-methyl}-benzamidine-hydrochloride Yield: 77.6% of theory, $C_{29}H_{27}N_5O_2 \times HCl$ (477.57/514.04); mass spectrum: $(M+H)^+$=478.

(19) 4-{[6-(1-(2-hydroxymethyl-pyrrolidin-1-yl-carbonyl)-cyclopropyl)-1-methyl-2-oxo-1,2-dihydroquinoxalin-3-yl]-methyl}-benzamidine-hydrochloride Yield: 62.7% of theory, $C_{26}H_{29}N_5O_3 \times HCl$ (459.55/496.02); mass spectrum: $(M+H)^+$=460;

$(M+H+Na)^{++}$=241.6.

(20) 4-{[6-(1-(N-(2-dimethylaminoethyl)-N-methyl-aminocarbonyl)-cyclopropyl)-1-methyl-2-oxo-1,2-dihydroquinoxalin-3-yl]-methyl}-benzamidine-dihydrochloride Yield: 66.9% of theory, $C_{26}H_{32}N_6O_2 \times HCl$ (460.59/497.05); mass spectrum: $(M+H)^+$=461.

(21) 4-{[6-(1-(N-(3-dimethylaminopropyl)-N-methyl-aminocarbonyl)-cyclopropyl)-1-methyl-2-oxo-1,2-dihydroquinoxalin-3-yl]-methyl}-benzamidine-dihydrochloride Yield: 59.7% of theory, $C_{27}H_{34}N_6O_2 \times HCl$ (474.61/511,08); mass spectrum: $(M+H)^+$=475;

$(M+2H)^{++}$=238.

(22) 4-{[6-(1-(2-ethoxycarbonylmethyl-piperidin-1-yl-carbonyl)-cyclopropyl)-1-methyl-2-oxo-1,2-dihydroquinoxalin-3-yl]-methyl}-benzamidine-hydrochloride Yield: 86.8% of theory, $C_{30}H_{35}N_5O_4 \times HCl$ (529.64/566.11); mass spectrum: $(M+H)^+$=530;

$(M+H+Na)^{++}$=276.7.

(23) 4-{[6-(1-(2-(N-(2-ethoxycarbonylethyl)-aminocarbonyl)-pyrrolidin-1-yl-carbonyl)-cyclopropyl)-1-methyl-2-oxo-1,2-dihydroquinoxalin-3-yl]-methyl}-benzamidine-hydrochloride Yield: 87.3% of theory, $C_{31}H_{36}N_6O_5 \times HCl$ (572.67/609.13); mass spectrum: $(M+H)^+$=573;

(M+H+Na)$^{++}$=298.

(24) 4-{[6-(1-(2-ethoxycarbonylmethylaminocarbonyl-pyrrolidin-1-yl-carbonyl)-cyclopropyl)-1-methyl-2-oxo-1,2-dihydroquinoxalin-3-yl]-methyl}-benzamidine-hydrochloride Yield: 59.2% of theory, $C_{30}H_{34}N_6O_5 \times HCl$ (558.64/595.11); mass spectrum: (M+H)$^+$=559; (M+H+Na)$^{++}$=291.

(25) 4-{[6-(1-(4-(2-methoxycarbonyl-ethyl)-piperidin-1-yl-carbonyl)-cyclopropyl)-1-methyl-2-oxo-1,2-dihydroquinoxalin-3-yl]-methyl}-benzamidine-hydrochloride Yield: 47.4% of theory, $C_{30}H_{35}N_5O_4 \times HCl$ (529.64/566.11); mass spectrum: (M+H)$^+$=530.

(26) 4-{[6-(1-methyl-1-(pyrrolidin-1-yl-carbonyl)-ethyl)-1-methyl-2-oxo-1,2-dihydroquinoxalin-3-yl]-difluoromethyl}-benzamidine-hydrochloride

(27) 2-{[6-(1-methyl-1-(pyrrolidin-1-yl-carbonyl)-ethyl)-1-methyl-2-oxo-1,2-dihydroquinoxalin-3-yl]-methyl}-thiophen-5-yl-amidine-hydrochloride

(28) 2-{[6-(1-methyl-1-(pyrrolidin-1-yl-carbonyl)-ethyl)-1-methyl-2-oxo-1,2-dihydroquinoxalin-3-yl]-methyl}-thiazol-5-yl-amidine-hydrochloride

(29) 2-{[6-(1-methyl-1-(pyrrolidin-1-yl-carbonyl)-ethyl)-1-methyl-2-oxo-1,2-dihydroquinoxalin-3-yl]-methyl}-pyridin-5-yl-amidine-hydrochloride

(30) 5-{[6-(1-methyl-1-(pyrrolidin-1-yl-carbonyl)-ethyl)-1-methyl-2-oxo-1,2-dihydroquinoxalin-3-yl]-methyl}-pyridin-2-yl-amidine-hydrochloride

(31) 4-{[6-(1-(pyrrolidin-1-yl-carbonyl)-cyclopropyl)-1-methyl-2-oxo-1,2-dihydroquinoxalin-3-yl]-difluoromethyl}-benzamidine-hydrochloride

(32) 2-{[6-(1-(pyrrolidin-1-yl-carbonyl)-cyclopropyl)-1-methyl-2-oxo-1,2-dihydroquinoxalin-3-yl]-methyl}-thiophen-5-yl-amidine-hydrochloride

(33) 2-{[6-(1-(pyrrolidin-1-yl-carbonyl)-cyclopropyl)-1-methyl-2-oxo-1,2-dihydroquinoxalin-3-yl]-methyl}-thiazol-5-yl-amidine-hydrochloride

(34) 2-{[6-(1-(pyrrolidin-1-yl-carbonyl)-cyclopropyl)-1-methyl-2-oxo-1,2-dihydroquinoxalin-3-yl]-methyl}-pyridin-5-yl-amidine-hydrochloride

(35) 5-{[6-(1-(pyrrolidin-1-yl-carbonyl)-cyclopropyl)-1-methyl-2-oxo-1,2-dihydroquinoxalin-3-yl]-methyl}-pyridin-2-yl-amidine-hydrochloride

(36) 5-{[6-(1-(1-methyl-pyrazol-5-yl-carbonyl)-cyclopropyl)-1-methyl-2-oxo-1,2-dihydroquinoxalin-3-yl]-methyl}-benzamidine-hydrochloride Yield: 7% of theory, $C_{25}H_{24}N_6O_2 \times HCl$ (440.51/476.96); mass spectrum: (M+H)$^+$=441.

EXAMPLE 22

4-{[6-(N-ethoxycarbonylmethyl-quinolin-8-yl-sulphonylamino)-1-methyl-2-thiono-1,2-dihydroquinoxalin-3-yl]-methyl}-benzamidine-hydrochloride a. 4-[(6-(quinolin-8-yl)-sulphonyl-N-ethoxycarbonylmethyl-amino-1-methyl-2-thiono-1,2-dihydroquinoxalin-3-yl)-methyl]-benzonitrile 830 mg (1.5 mmol) of 4-{[6-(N-ethoxycarbonylmethyl-quinolin-8-yl-sulphonylamino)-1-methyl-2-oxo-1,2-dihydroquinoxalin-3-yl]-methyl}-benzonitrile and 310 mg (0.75 mmol) of 2,4-bis-(4-methoxyphenyl)-1,3-dithia-2,4-diphosphetan-2,4-disulphide are refluxed for 16 hours in 20 ml toluene. The solvent is distilled off, the residue chromatographed on silica gel and eluted with methylene chloride/ethanol (99:1).

Yield: 34.1% of theory, $C_{30}H_{25}N_5O_4S_2$ (583.68); mass spectrum: M$^+$=583.

b. 4-{[6-(N-ethoxycarbonylmethyl-quinolin-8-yl-sulphonyl-amino)-1-methyl-2-thiono-1,2-dihydroquinoxalin-3-yl]-methyl}-benzamidine-hydrochloride Prepared analogously to Example 1f from 4-{[6-(N-ethoxycarbonylmethyl-quinolin-8-yl-sulphonylamino)-1-methyl-2-thiono-1,2-dihydroquinoxalin-3-yl]-methyl}-benzonitrile and hydrochloric acid/ammonium carbonate in ethanol.

Yield: 19.4% of theory, $C_{30}H_{28}N_6O_4S_2 \times HCl$ (600.72/637.17); mass spectrum: (M+H)$^+$=601.

EXAMPLE 23

4-{[6-(1-carboxy-cyclopropyl)-1-methyl-2-oxo-1,2-dihydroquinoxalin-3-yl]-methyl}-benzamidine-hydrochloride a. 4-{[6-(1-carboxy-cyclopropyl)-1-methyl-2-oxo-1,2-dihydroquinoxalin-3-yl]-methyl}-N-hydroxybenzamidine 1.0 g (2.78 mmol) of 4-{[6-(1-carboxy-cyclopropyl)-1-methyl-2-oxo-1,2-dihydroquinoxalin-3-yl]-methyl}-benzonitrile, 0.47 g (6.76 mmol) of hydroxylamine hydrochloride and 0.35 g (3.3 mmol) of potassium carbonate are refluxed for 25 hours in 100 ml methanol and 10 ml water. The solvent is distilled off, the residue chromatographed on silica gel and eluted with methylene chloride+5–10% ethanol. The desired fractions are combined and evaporated down.

Yield: 0.34 g (31% of theory), Rf value: 0.6 (silica gel; methylene chloride/ethanol=9:1).

b. 4-{[6-(1-carboxy-cyclopropyl)-1-methyl-2-oxo-1,2-dihydroquinoxalin-3-yl]-methyl}-benzamidine 300 mg (0.76 mmol) of 4-{[6-(1-carboxy-cyclopropyl)-1-methyl-2-oxo-1,2-dihydroquinoxalin-3-yl]-methyl}-N-hydroxybenzamidine are dissolved in 30 ml of 90% acetic acid and after the addition of 400 mg palladium on activated charcoal hydrogenated with hydrogen at 60° C. The catalyst is filtered off, the solution is evaporated down. The residue is chromatographed on silica gel and eluted with methanol. The desired fractions are evaporated down, triturated with ether, suction filtered and dried.

Yield: 70 mg (24% of theory), $C_{21}H_{20}N_4O_3$ (376.42); mass spectrum: (M+H)$^+$=377.

EXAMPLE 24

4-{[6-(1-(pyrrolidin-1-yl-carbonyl)-2-ethoxycarbonylmethyl-ethyl)-1-methyl-2-oxo-1,2-dihydroquinoxalin-3-yl]-methyl}-benzamidine-hydrochloride a. 2-(4-chlorophenyl)-1-(pyrrolidin-1-yl)-ethanone Prepared analogously to Example 2a from p-chlorophenylacetic acid, pyrrolidine, O-(benzotriazol-1-yl)-N,N,N'N'-tetramethyluroniumtetrafluoroborate and N-methylmorpholine in dimethylformamide.

Yield: 75% of theory, R$_f$ value: 0.5 (silica gel; methylene chloride/ethanol=19:1).

b. Ethyl 3-(4-chlorophenyl)-4-oxo-4-(pyrrolidin-1-yl)-butyrate 16.8 g (0.075 mol) of 2-(4-chlorophenyl)-1-(pyrrolidin-1-yl)-ethanone are dissolved in 175 ml dimethylsulphoxide and after the addition of 8.9 g (0.08 mol) of potassium tert.butoxide, stirred for 15 minutes at ambient temperature. After the addition of 18.1 ml (0.085 mol) of ethyl iodoacetate the reaction mixture is stirred for 45 hours at ambient temperature. The solution is poured onto ice water and extracted with ethyl acetate. The combined organic extracts are washed with sodium chloride solution, dried and evaporated down. The residue is chromatographed on silica gel, eluting first with petroleum ether and later with petroleum ether/ethyl acetate (8:2 and 1:1). The desired fractions are combined and evaporated down.

Yield: 11.0 g (48% of theory), $R_f$ value: 0.73 (silica gel; ethyl acetate/petroleum ether=7:3).

c. Ethyl 3-(4-chloro-3-nitrophenyl)-4-oxo-4-(pyrrolidin-1-yl)-butyrate and ethyl 3-(4-chloro-2-nitrophenyl)-4-oxo-4-(pyrrolidin-1-yl)-butyrate 7.8 g (0.025 mol) of ethyl 3-(4-chlorophenyl)-4-oxo-4-(pyrrolidin-1-yl)-butyrate are added batchwise to 40 ml of fuming nitric acid at −30° C. The solution is stirred for 15 minutes at −30° C. and subsequently poured onto ice water. The supernatant water is decanted off, the residue is taken up in ethyl acetate and sodium hydrogen carbonate solution and extracted. The combined organic extracts are dried and evaporated down.

Yield: 7.9 g (89% of theory) of ethyl 3-(4-chloro-3-nitrophenyl)-4-oxo-4-(pyrrolidin-1-yl)-butyrate and ethyl 3-(4-chloro-2-nitrophenyl)-4-oxo-4-(pyrrolidin-1-yl)-butyrate as an isomer mixture in the ratio 1:9; $R_f$ value: 0.68 (silica gel; methylene chloride/ethanol=19:1).

d. Ethyl 3-(4-methylamino-3-nitrophenyl)-4-oxo-4-(pyrrolidin-1-yl)-butyrate 7.9 g (23 mmol) of ethyl 3-(4-chloro-3-nitrophenyl)-4-oxo-4-(pyrrolidin-1-yl)-butyrate and ethyl 3-(4-chloro-2-nitrophenyl)-4-oxo-4-(pyrrolidin-1-yl)-butyrate (isomer mixture) are dissolved in 65 ml ethanol and after the addition of 5 ml methylamine heated to 80° C. in a pressure vessel for 1 hour. After cooling to ambient temperature and adding 5 g silica gel, the mixture is evaporated to dryness. The residue is chromatographed on silica gel, eluting first with petroleum ether and later with petroleum ether/ethyl acetate (9:1).

Yield: 330 mg (3.6% of theory), $R_f$ value: 0.58 (silica gel; methylene chloride/ethanol=19:1); $C_{17}H_{23}N_3O_5$ (349.4); mass spectrum: $M^+$=349.

e. Ethyl 3-(4-methylamino-3-amino-phenyl)-4-oxo-4-(pyrrolidin-1-yl)-butyrate 300 mg (8.6 mmol) of ethyl 3-(4-methylamino-3-nitrophenyl)-4-oxo-4-(pyrrolidin-1-yl)-butyrate are dissolved in 60 ml ethyl acetate and 10 ml methanol and after the addition of 600 mg Raney nickel hydrogenated with hydrogen for 2.5 hours at ambient temperature. The catalyst is filtered off and the filtrate is concentrated by evaporation.

Yield: 260 mg (94% of theory), $R_f$ value: 0.28 (silica gel; methylene chloride/ethanol=19:1).

f. 4-{[6-(1-(pyrrolidin-1-yl-carbonyl)-2-ethoxycarbonylmethyl-ethyl)-1-methyl-1H-benzimidazol-2-yl]-methyl}-benzonitrile and 4-{[5-(1-pyrrolidin-1-yl-carbonyl)-2-ethoxycarbonylmethyl-ethyl)-1-methyl-2-oxo-1,2-dihydroquinoxalin-3-yl]-methyl}-benzonitrile 260 mg (0.81 mmol) of ethyl 3-(3-amino-4-methylamino-phenyl)-4-(pyrrolinocarbonyl)-butyrate and 189 mg (1.0 mmol) of 3-(4-cyano-phenyl)-2-oxo-propionic acid are refluxed for 1 hour in 10 ml ethanol. The reaction solution is combined with 5 g silica gel and evaporated to dryness. The residue is chromatographed on silica gel, eluting first with petroleum ether and later with petroleum ether/ethyl acetate (9:1 and 8:2). The desired fractions are combined and evaporated down.

Yield: 100 mg (28% of theory) of 4-{[5-(1-(pyrrolidin-1-yl-carbonyl)-2-ethoxycarbonylmethyl-ethyl)-1-methyl-1H-benzimidazol-2-yl]-methyl}-benzonitrile, $R_f$ value: 0.28 (silica gel; methylene chloride/ethanol=19:1); $C_{26}H_{28}N_4O_3$ (444.5), mass spectrum: $M^+$=444; and 200 mg (52% of theory) of 4-{[6-(1-(pyrrolidin-1-yl-carbonyl-2-ethoxycarbonylmethyl-ethyl)-1-methyl-2-oxo-1,2-dihydroquinoxalin-3-yl]-methyl}-benzonitrile, $C_{27}H_{28}N_4O_4$ (472.5); mass spectrum: $M^+$=472.

g. 4-{[6-(1-(pyrrolidin-1-yl-carbonyl)-2-ethoxycarbonylmethyl-ethyl)-1-methyl-2-oxo-1,2-dihydroquinoxalin-3-yl]-methyl}-benzamidine-hydrochloride Prepared analogously to Example 1f from 4-{[6-(1-(pyrrolidin-1-yl-carbonyl)-2-ethoxycarbonylmethyl-ethyl)-1-methyl-2-oxo-1,2-dihydroquinoxalin-3-yl]-methyl}-benzonitrile and hydrochloric acid/ammonium carbonate in ethanol.

Yield: 29.6% of theory, $C_{27}H_{31}N_5O_4 \times HCl$ (489.57/526.03); mass spectrum: $(M+H)^+$=490.

EXAMPLE 25

4-{[6-(1-(N-cyclopentyl-ethoxycarbonylmethylcarbonylamino)-cyclopropyl)-1-methyl-2-oxo-1,2-dihydroquinoxalin-3-yl)-methyl]-benzamidine-hydrochloride a. 4-{[6-(1-(N-tert.butyloxycarbonylamino)-cyclopropyl)-1-methyl-2-oxo-1,2-dihydroquinoxalin-3-yl)-methyl]-benzonitrile A suspension of 10.6 g (0.03 mol) of 4-{[6-(1-carboxy-cyclopropyl)-1-methyl-2-oxo-1,2-dihydroquinoxalin-3-yl]-methyl}-benzonitrile in 110 ml tert.butanol is combined with 4.2 ml (0.03 mol) of triethylamine and 7 ml (0.03 mol) of phosphoric acid diphenylester azide under a nitrogen atmosphere and refluxed for 3 hours. The suspension is cooled to 20° C. and combined with 2.7 g (0.024 mol) of potassium tert.butoxide within 30 minutes. After 2 hours the mixture is stirred with ice water and extracted with ethyl acetate. The organic phase is washed with sodium hydrogen carbonate solution and citric acid, dried and evaporated down.

Yield: 12.5 g (97% of theory), $R_f$ value: 0.6 (silica gel; methylene chloride/ethanol=9:1).

b. 4-{[6-(1-amino-cyclopropyl)-1-methyl-2-oxo-1,2-dihydroquinoxalin-3-yl)-methyl]-benzonitrile 12.5 g (0.03 mol) of 4-{[6-(1-(N-tert.butyloxycarbonylamino)-cyclopropyl)-1-methyl-2-oxo-1,2-dihydroquinoxalin-3-yl]-methyl}-benzonitrile are suspended in 160 ml dioxane and after the addition of 400 ml of 6N hydrochloric acid stirred for 4 hours at ambient temperature. The reaction mixture is poured onto ice water and made alkaline with conc. ammonia. Then the mixture is extracted with ethyl acetate, the combined organic extracts are washed with sodium chloride solution, dried and evaporated down. The residue is chromatographed on silica gel and eluted with methylene chloride/ethanol/ammonia (100:2:0.05, 20:1:0.025 and 10:1:0). The desired fractions are combined and evaporated down.

Yield: 6.6 g (69% of theory), $R_f$ value: 0.28 (silica gel; methylene chloride/ethanol=9:1).

c. 4-{[6-(1-cyclopentylamino-cyclopropyl)-1-methyl-2-oxo-1,2-dihydroquinoxalin-3-yl]-methyl}-benzonitrile 3.0 g (9 mmol) of 4-{[6-(1-amino-cyclopropyl)-1-methyl-2-oxo-1,2-dihydroquinoxalin-3-yl]-methyl}-benzonitrile and 1.0 ml (11.2 mmol) of cyclopentanone are dissolved in 150 ml tetrahydrofuran and 0.54 ml (9 mmol) of glacial acetic acid, combined batchwise with 2.5 g (12 mmol) of sodium triacetoxyborohydride under a nitrogen atmosphere at 22° C. and stirred for 24 hours at ambient temperature. Then the mixture is poured onto ice water, acidified with hydrochloric acid and extracted with ethyl acetate. The aqueous phase is made alkaline with conc. ammonia and extracted with ethyl acetate. The combined organic extracts are washed with sodium chloride solution, dried and evaporated down.

Yield: 3.3 g (92% of theory), $R_f$ value: 0.58 (silica gel; ethyl acetate/ethanol=9:1).

d. 4-{[6-(1-(N-cyclopentyl-ethoxycarbonylmethylcarbonylamino)-cyclopropyl)-1-methyl-2-oxo-1,2-dihydroquinoxalin-3-yl]-methyl}-benzonitrile To a solution of 2.0 g (5 mmol) of {[(6-(1-cyclopentyl-amino-cyclopropyl)-1-methyl-2-oxo-1,2-dihydroquinoxalin-3-yl]-methyl}-benzonitrile in 40 ml tetrahydrofuran are added 0.77 ml (5.5 mmol) of triethylamine and then 0.7 ml (5.5 mmol) of monoethyl malonate chloride are added dropwise. The reaction mixture is cooled to 20° C., stirred for 30 minutes and combined with ice water. Then the mixture is made alkaline with conc. ammonia, extracted with ethyl acetate, the organic phases are washed with hydrochloric acid and water, dried and evaporated down. The residue is chromatographed on silica gel and eluted with cyclohexane/ethyl acetate/glacial acetic acid (1:1:0.001). The desired fractions are combined and evaporated down.

Yield: 2.1 g (82% of theory), $R_f$ value: 0.22 (silica gel; cyclohexane/ethyl acetate=1:1).

e. 4-{[6-(N-cyclopentyl-ethoxycarbonylmethylcarbonylamino)-cyclopropyl)-1-methyl-2-oxo-1,2-dihydroquinoxalin-3-yl]-methyl}-benzamidine-hydrochloride Prepared analogously to Example 1f from 4-{[6-(1-(N-cyclopentyl-ethoxycarbonylmethylcarbonylamino)-cyclopropyl)-1-methyl-2-oxo-1,2-dihydroquinoxalin-3-yl]-methyl}-benzonitrile and hydrochloric acid/ammonium carbonate in ethanol.

$C_{30}H_{35}N_5O_4 \times HCl$ (529.64/566.11); mass spectrum: $(M+H)^+=530$;

$(M+H+Na)^{++}=276.7$.

The following compound is prepared analogously:

(1) 4-{[6-(1-(N-cyclopentyl-N-(3-ethoxycarbonylpropionyl)-amino)-cyclopropyl)-1-methyl-2-oxo-1,2-dihydroquinoxalin-3-yl]-methyl}-benzamidine-hydrochloride Yield: 98% of theory, $C_{31}H_{37}N_5O_4 \times HCl$ (543.67/580.13); mass spectrum: $(M+H)^+=544$.

EXAMPLE 26

4-{[6-(1-ethoxycarbonylmethylcarbonylamino-1-(pyrrolidin-1-yl-carbonyl)-ethyl)-1-methyl-2-oxo-1,2-dihydroquinoxalin-3-yl]-methyl}-benzamidine-hydrochloride a. 5-(4-chloro-3-nitrophenyl)-5-methyl-imidazolidin-2,4-dione 10.0 g (4.45 mmol) of 5-(4-chlorophenyl)-5-methyl-imidazolidin-2,4-dione are added batchwise to 50 ml of fuming nitric acid at −25° C. to −35° C. After 45 minutes at −25° C. to −20° C. the reaction mixture is poured onto ice water. The crystalline product is suction filtered, washed with water and dried.

Yield: 10.5 g (100% of theory), melting point: 173–178° C.; $R_f$ value: 0.30 (silica gel; cyclohexane/ethyl acetate= 1:1).

b. 2-amino-2-(4-chloro-3-nitrophenyl)-propionic acid 10.5 g (0.044 mol) of 5-(4-chloro-3-nitrophenyl)-5-methyl-imidazolidin-2,4-dione are refluxed for 5 days in 200 ml dioxane and 700 ml 6N hydrochloric acid. The solution is cooled and evaporated down, taken up in water and extracted with ethyl acetate. The aqueous phase is evaporated down, combined with toluene and evaporated to dryness. The residue is triturated with ether, suction filtered and dried.

Yield: 6.8 g (63% of theory), $R_f$ value: 0.24 (reversed phase RP8; 5% saline solution/methanol=1:1).

c. 2-tert.butoxycarbonylamino-2-(4-chloro-3-nitrophenyl)-propionic acid 6.8 g (0.028 mol) of 2-amino-2-(4-chloro-3-nitrophenyl)-propionic acid are dissolved in 100 ml dioxane, 20 ml water and 0.5 ml (0.061 mol) of triethylamine and, after the addition of 7.3 g (0.033 mol) of pyrocarbonic acid-di-tert.butyldicarbonate, stirred for 16 hours at ambient temperature. Then the mixture is diluted with ethyl acetate and washed with potassium hydrogen sulphate solution and water. The organic extracts are combined, dried and evaporated down.

Yield: 9.6 g (100% of theory), $R_f$ value: 0.31 (reversed phase RP8; 5% saline solution/methanol=1:2).

d. tert. Butyl [1-(4-chloro-3-nitrophenyl)-1-methyl-2-oxo-2-pyrrolidin-1-yl-ethyl]-carbaminate Prepared analogously to Example 2a from 2-tert.butoxycarbonylamino-2-(4-chloro-3-nitrophenyl)-propionic acid, O-(benzotriazol-1-yl)-N,N,N'N'-tetramethyluroniumtetrafluoroborate, pyrrolidine and N-methylmorpholine in dimethylformamide.

Yield: 94% of theory, $R_f$ value: 0.11 (silica gel; cyclohexane/ethyl acetate 1:1).

e. tert. Butyl [1-(4-methylamino-3-nitrophenyl)-1-methyl-2-oxo-2-pyrrolidin-1-yl-ethyl]-carbaminate Prepared analogously to Example 7a from tert.butyl [1-(4-chloro-3-nitrophenyl)-1-methyl-2-oxo-2-pyrrolidin-1-yl-ethyl]-carbaminate and methylamine solution in dimethylformamide at 160° C. $R_f$ value: 0.79 (silica gel; ethyl acetate/ethanol=9:1).

f. tert.butyl [1-(3-amino-4-methylamino-phenyl)-1-methyl-2-oxo-2-pyrrolidin-1-yl-ethyl]-carbaminate Prepared analogously to Example 1d from tert.butyl [1-(4-methylamino-3-nitrophenyl)-1-methyl-2-oxo-2-pyrrolidin-1-yl-ethyl]-carbaminate and palladium on activated charcoal/hydrogen in methanol.

Yield: 100% of theory, $R_f$ value: 0.63 (silica gel; ethyl acetate/ethanol=9:1).

g. 4-{[6-(1-tert.butoxycarbonylamino-1-(pyrrolidin-1-yl-carbonyl)-ethyl)-1-methyl-2-oxo-1,2-dihydroquinoxalin-3-yl]-methyl}-benzonitrile Prepared analogously to Example 7f from tert.butyl [1-(3-amino-4-methylamino-phenyl)-1-methyl-2-oxo-2-pyrrolidin- 1-yl-ethyl]-carbaminate and 4-(2-oxo-propionic acid)-benzonitrile in ethanol.

Yield: 54% of theory, $R_f$ value: 0.18 (silica gel; cyclohexane/ethyl acetate=1:1).

4-{[6-(1-amino-1-(pyrrolidin-1-yl-carbonyl)-ethyl)-1-methyl-2-oxo-1,2-dihydroquinoxalin-3-yl]-methyl}-benzonitrile Prepared analogously to Example 25b from 4-{[6-(1-tert.butoxycarbonylamino-1-(pyrrolidin-1-yl-carbonyl)-ethyl)-1-methyl-2-oxo-1,2-dihydroquinoxalin-3-yl]-methyl}-benzonitrile and 6N hydrochloric acid in dioxane.

Yield: 89% of theory, $R_f$ value: 0.11 (silica gel; ethyl acetate/ethanol/ammonia=9:1:0.01).

i. 4-{[6-(1-ethoxycarbonylmethylcarbonylamino-1-(pyrrolidin-1-yl-carbonyl)-ethyl)-1-methyl-2-oxo-1,2-dihydroquinoxalin-3-yl]-methyl}-benzonitrile Prepared analogously to Example 25d from 4-{[6-(1-amino-1-(pyrrolidin-1-yl-carbonyl)-ethyl)-1-methyl-2-oxo-1,2-dihydroquinoxalin-3-yl]-methyl}-benzonitrile, monoethyl malonate chloride and triethylamine in tetrahydrofuran.

Yield: 78% of theory, $R_f$ value: 0.58 (silica gel; ethyl acetate/ethanol=9:1).

k. 4-{[6-(1-ethoxycarbonylmethylcarbonylamino-1-(pyrrolidin-1-yl-carbonyl)-ethyl)-1-methyl-2-oxo-1,2-dihydroquinoxalin-3-yl]-methyl}-benzamidine-hydrochloride Prepared analogously to Example 1f from 4-{[6-(1-ethoxycarbonylmethylcarbonylamino-1-(pyrrolidin-1-yl-carbonyl)-ethyl)-1-methyl-2-oxo-1,2-dihydroquinoxalin-3-yl]-methyl}-benzonitrile and hydrochloric acid/ammonium carbonate in ethanol.

Yield: 73% of theory, $C_{29}H_{34}N_6O_5{\times}HCl$ (546.63/583.11); mass spectrum: $(M+H)^+=547$;

$(M+H+Na)^{++}=285$.

The following compounds were prepared analogously:

(1) 5-{[6-(1-(2-ethoxycarbonyl-ethylcarbonylamino)-1-ethoxy-carbonyl-ethyl)-1-methyl-2-oxo-1,2-dihydroquinoxalin-3-yl]-methyl}-benzamidine-hydrochloride Yield: 93% of theory, $C_{28}H_{33}N_5O_6{\times}HCl$ (535.61/572.08); mass spectrum: $(M+H)^+=536$;

$(M+H+Na)^{++}=279.5$.

(2) 5-{[6-(1-ethoxycarbonylmethylamino-1-(pyrrolidin-1-yl-carbonyl)-ethyl)-1-methyl-2-oxo-1,2-dihydroquinoxalin-3-yl]-methyl}-benzamidine-hydrochloride Yield: 85% of theory, $C_{27}H_{35}N_7O_3{\times}HCl$ (512.62.=/555.08); mass spectrum: $(M+H)^+=519$;

$(M+Na)^+=541$.

EXAMPLE 27

4-{[7-(4-methyl-phenyl)-4-methyl-quinolin-2-yl]-oxo}-benzamidine-hydrochloride a. N-(3-bromo-phenyl)-3-oxo-butyramide 10.9 g (0.1 mol) of 3-bromaniline are added dropwise at 160° C. to 52 ml (0.4 mol) of ethyl acetate. After 15 minutes at 160° C. the excess ethyl acetate is distilled off under high vacuum. After cooling the residue is dissolved in methylene chloride and chromatographed on silica gel, eluting with methylene chloride/ethanol 9:1. The desired fractions are combined and evaporated down.

Yield: 17.7 g (69% of theory), $R_f$ value: 0.83 (silica gel; ethyl acetate/ethanol=9:1).

b. 7-bromo-4-methyl-1H-quinolin-2-one 3.5 g (0.013 mol) of N-(3-bromo-phenyl)-3-oxo-butyramide are added batchwise at 85° C. to 4.7 ml conc. sulphuric acid and then stirred for 15 minutes at 105° C. Then the mixture is cooled to 60° C., stirred into ice water and made alkaline with conc. Ammonia. The product precipitated is suction filtered, washed with water and dried.

Yield: 2.2 g (68% of theory), $R_f$ value: 0.66 (silica gel; ethyl acetate/ethanol=9:1).

c. 7-bromo-2-chloro-4-methyl-quinoline 2.1 g (9.2 mmol) of 7-bromo-4-methyl-1H-quinolin-2-one are refluxed in 30 ml of phosphorus oxychloride for 30 minutes and subsequently mixed with water at 30 to 50° C. After the addition of conc. ammonia, the product precipitated is suction filtered, washed with water and dried.

Yield: 2.0 g (85% of theory), $R_f$ value: 0.71 (silica gel; cyclohexane/ethyl acetate=2:1).

d. 4-[(7-bromo-4-methyl-quinolin-2-yl)oxyl-benzonitrile 1.9 g (7.4 mmol) of 7-bromo-2-chloro-4-methyl-quinoline are melted with 1.8 g (14.8 mmol) of 4-hydroxybenzonitrile for 1 hour at 175° C. After cooling the reaction product is decocted with ethyl acetate. After filtration the mother liquor is washed with sodium hydroxide solution and water, dried and evaporated down. The residues are chromatographed over silica gel, eluting with cyclohexane/ethyl acetate (9:1 and 5:1). The desired fractions are combined and evaporated down.

Yield: 1.6 g (66% of theory), $R_f$ value: 0.46 (silica gel; petroleum ether/ethyl acetate=4:1).

e. 4-[(7-(4-methyl-phenyl)-4-methyl-quinolin-2-yl)-oxo]-benzonitrile

To a suspension of 1.5 g (4.4 mmol) of 4-[(7-bromo-4-methyl-quinolin-2-yl)oxy]-benzonitrile in 20 ml toluene and 0.94 g (8.8 mmol) of sodium carbonate in 6 ml water are added 0.14 g (0.12 mmol) of tetrakis-(triphenylphosphine)-palladium (0) and 0.6 g (4.4 mmol) of 4-methylphenylboric acid. The suspension is refluxed for 6 hours and stirred for 3 days at ambient temperature. Then it is extracted with ethyl acetate and washed with water and sodium chloride solution, the organic phase is dried and evaporated down. The residue is chromatographed on silica gel and eluted with cyclohexane/ethyl acetate (1:0 and 9:1). The desired fractions are combined and evaporated down.

Yield: 1.1 g (71% of theory), $R_f$ value: 0.43 (silica gel; petroleum ether/ethyl acetate=4:1).

f. 4-{[7-(4-methyl-phenyl)-4-methyl-quinolin-2-yl)-oxo]-benzamidine-hydrochloride Prepared analogously to Example 1f from 4-{[7-(4-methyl-phenyl)-4-methyl-quinolin-2-yl)-oxo3-benzonitrile and hydrochloric acid/ammonium carbonate in ethanol.

Yield: 11% of theory, $C_{24}H_{31}N_4O{\times}HCl$ (367.46/403.92); mass spectrum: $(M+H)^+=368$;

$(2M+H)^+=735$.

The following compounds are prepared analogously:

(1) 4-[(7-bromo-4-methyl-quinolin-2-yl)-oxo]-benzamidine-hydrochloride

Yield: 75% of theory, $C_{17}H_{14}BrN_3O \times HCl$ (356.24/392.70); mass spectrum: $(M+H)^+=356/8$ (Br).

(2) 4-{[7-(2-methyl-phenyl)-4-methyl-quinolin-2-yl]-oxo}-benzamidine-hydrochloride Yield: 71% of theory, $C_{24}H_{21}N_3O{\times}HCl$ (367.46/403.92); mass spectrum: $(M+H)^+=368$.

(3) 4-{[7-(2-ethoxycarbonyl-phenyl)-4-methyl-quinolin-2-yl]-oxo}-benzamidine-hydrochloride Yield: 16% of theory, $C_{26}H_{23}N_3O_3{\times}HCl$ (425.49/461.95); mass spectrum: $(M+H)^+=426$.

(4) 4-{[7-(4-ethoxycarbonyl-phenyl)-4-methyl-quinolin-2-yl]-oxo}-benzamidine-hydrochloride Yield: 61% of theory, $C_{26}H_{23}N_3O_3{\times}HCl$ (425.49/461.95); mass spectrum: $(M+H)^+=426$.

(5) 4-{[7-(3-ethoxycarbonyl-phenyl)-4-methyl-quinolin-2-yl]-oxo}-benzamidine-hydrochloride Yield: 57% of theory, $C_{26}H_{23}N_3O_3{\times}HCl$ (425.49/461.95); mass spectrum: $(M+H)^+=426$.

(6) 4-{[7-(3-amino-phenyl)-4-methyl-quinolin-2-yl]-oxo}-benzamidine-hydrochloride Yield: 93% of theory, $C_{23}H_{20}N_4O{\times}HCl$ (368.45/404.91); mass spectrum: $(M+H)^+=369$.

(7) 4-{[7-(3-ethoxycarbonylmethylamino-phenyl)-4-methyl-quinolin-2-yl]-oxo}-benzamidine-hydrochloride Yield: 98% of theory, $C_{27}H_{26}N_4O_3{\times}HCl$ (454.54/491.00); mass spectrum: $(M+H)^+=455$.

(8) 4-{[7-(3-nitro-phenyl)-4-methyl-quinolin-2-yl]-oxo}-benzamidine-hydrochloride Yield: 79% of theory, $C_{23}H_{18}N_4O_3{\times}HCl$ (398.43/434.89); mass spectrum: $(M+H)^+=399$.

(9) 4-{[7-(4-ethoxycarbonylmethylaminocarbonyl-phenyl)-4-methyl-quinolin-2-yl]-oxo}-benzamidine-hydrochloride Yield: 86% of theory, $C_{28}H_{26}N_4O_4{\times}HCl$ (482.54/519.0); mass spectrum: $(M+H)^+=483$.

(10) 4-[(4-methyl-quinolin-2-yl)-oxo]-benzamidine-hydrochloride

Yield: 35% of theory, $C_{17}H_{15}N_3O \times HCl$ (277.33/313.79); mass spectrum: $M^+=277$.

(11) 4-[(7-bromo-4-methyl-quinolin-2-yl)-thio]-benzamidine-hydrochloride

Yield: 100% of theory, $C_{17}H_{14}BrN_3S \times HCl$ (372.31/408.77); mass spectrum: $(M+H)^+=372/4$ (Br).

(12) 4-{[7-(N-(2-ethoxycarbonylpropionyl)-N-ethyl-amino)-4-methyl-quinolin-2-yl]-oxo}-benzamidine-hydrochloride Yield: 43% of theory, $C_{25}H_{28}N_4O_4 \times HCl$ (448.5/484.97); mass spectrum: $(M+H)^+=449$.

(13) 4-{[7-(N-ethyl-ethoxycarbonylmethylcarbonylamino)-4-methyl-quinolin-2-yl]-oxo}-benzamidine-hydrochloride Yield: 60% of theory, $C_{24}H_{26}N_4O_4 \times HCl$ (434.49/470.96); mass spectrum: $(M+H)^+=435$.

(14) 4-{[7-(N-ethoxycarbonylmethylaminocarbonyl-N-ethyl-amino)-4-methyl-quinolin-2-yl]-oxo}-benzamidine-hydrochloride Yield: 73% of theory, $C_{24}H_{27}N_5O_4 \times HCl$ (449.51/485.97); mass spectrum: $(M+H)^+=450$.

(15) 4-{[7-(N-(1H-tetrazol-5-yl-methylcarbonyl)-N-ethyl-amino)-4-methyl-quinolin-2-yl]-amino}-benzamidine-hydrochloride Yield: 42.8% of theory, $C_{22}H_{23}N_9O \times HCl$ (429.49/465.96); mass spectrum: $(M+H)^+=430$.

(16) 4-{[7-(1-ethoxycarbonylmethylcarbonylamino-ethyl)-4-methyl-quinolin-2-yl]-oxy}-benzamidine-hydrochloride Yield: 10.6% of theory, $C_{24}H_{26}N_4O_4 \times HCl$ (434.49/470.97); mass spectrum: $(M+H)^+=435$.

(17) 4-{[7-(1-(2-ethoxycarbonylethylcarbonylamino)-ethyl)-4-methyl-quinolin-2-yl]-oxy}-benzamidine-hydrochloride Yield: 12.4% of theory, $C_{25}H_{28}N_4O_4 \times HCl$ (448.53/485.00); mass spectrum: $(M+H)^+=449$.

(18) 4-{[7-(1-acetylamino-ethyl)-4-methyl-quinolin-2-yl]-oxy}-benzamidine-hydrochloride Yield: 55% of theory, $C_{21}H_{22}N_4O_2 \times HCl$ (362.44/398.9); mass spectrum: $(M+H)^+=363$.

EXAMPLE 28

4-{[7-(2-(2-(E)-ethoxycarbonylethenyl)-phenyl)-4-methyl-quinolin-2-yl]-oxo}-benzamidine-hydrochloride a. 4-{[7-(2-formyl-phenyl)-4-methyl-quinolin-2-yl]-oxy}-benzonitrile Prepared analogously to Example 27e from 4-[(7-bromo-4-methyl-quinolin-2-yl)oxy]-benzonitrile, 2-formylbenzeneboric acid, sodium carbonate and tetrakis-(triphenylphosphine)-palladium (0) in toluene/water.

Yield: 73% of theory, $R_f$ value: 0.29 (silica gel; petroleum ether/ethyl acetate=4:1).

b. 4-{[7-(2-(2-(E)-carboxyethenyl)-phenyl)-4-methyl-quinolin-2-yl]-oxo}-benzonitrile A suspension of 1.8 g (5 mmol) of 4-[[7-(2-formyl-phenyl)-4-methyl-quinolin-2-yl]oxy}-benzonitrile in 8 ml pyridine is heated to 125° C. with 0.9 g (8.6 mmol) of malonic acid and 0.05 ml of piperidine for 2.5 hours. After cooling the solution formed is poured onto ice water and adjusted to pH 3–4 with citric acid. Then the mixture is extracted with ethyl acetate, the organic phase is washed with water and sodium chloride solution, dried and evaporated down.

Yield: 1.6 g (79% of theory), $R_f$ value: 0.59 (silica gel; ethyl acetate/ethanol=9:1).

c. 4-{[7-(2-(2-(E)-ethoxycarbonylethenyl)-phenyl-4)-methyl-quinolin-2-yl]-oxo}-benzamidine-hydrochloride Prepared analogously to Example 1f from 4-{[7-(2-(2-(E)-carboxyethenyl)-phenyl)-4-methyl-quinolin-2-yl]-oxo}-benzonitrile and hydrochloric acid/ammonium carbonate in ethanol.

Yield: 87% of theory, $C_{28}H_{27}N_3O_3 \times HCl$ (453.55/490.01); mass spectrum: $(M+H)^+=454$.

EXAMPLE 29

4-{[7-(2-(2-ethoxycarbonylethyl)-phenyl)-4-methyl-quinolin-2-yl]-oxo}-benzamidine-hydrochloride a. 4-{[7-(2-(2-carboxyethyl)-phenyl)-4-methyl-quinolin-2-yl]-oxo}-benzonitrile 0.8 g (2 mmol) of 4-{[7-(2-(2-(E)-carboxyethenyl)-phenyl)-4-methyl-quinolin-2-yl]-oxo}-benzonitrile are dissolved in 20 ml dimethylformamide and, after the addition of 0.2 g palladium on activated charcoal, hydrogenated with hydrogen at ambient temperature. The catalyst is filtered off, the mother liquor is evaporated down, combined with ice water and extracted with ethyl acetate. The combined organic extracts are washed with water and sodium chloride solution, dried and evaporated down.

Yield: 0.8 g (98% of theory), $R_f$ value: 0.68 (silica gel; ethyl acetate).

b. 4-{[7-(2-(2-ethoxycarbonylethyl)-phenyl)-4-methyl-quinolin-2-yl]-oxo}-benzamidine-hydrochloride Prepared analogously to Example 1f from 4-{[7-(2-(2-ethoxycarbonylethyl)-phenyl)-4-methyl-quinolin-2-yl]-oxo}-benzonitrile and hydrochloric acid/ammonium carbonate in ethanol.

Yield: 87% of theory, $C_{28}H_{27}N_3O_3 \times HCl$ (453.55/490.01); mass spectrum: $(M+H)^+=454$.

The following compounds are prepared analogously:

(1) 4-{[7-(2-ethoxycarbonyl-2-methyl-ethyl)-4-methyl-quinolin-2-yl]-oxo}-benzamidine-hydrochloride Yield: 71.8% of theory, $C_{23}H_{25}N_3O_3 \times HCl$ (391.48/427.94); mass spectrum: $(M+H)^+=392$.

(2) 4-{[7-(2-ethoxycarbonyl-1-methyl-ethyl)-4-methyl-quinolin-2-yl]-oxo}-benzamidine-hydrochloride Yield: 93.7% of theory, $C_{23}H_{25}N_3O_3 \times HCl$ (391.48/427.94); mass spectrum: $(M+H)^+=392$.

(3) 4-{[7-(2-ethoxycarbonylmethylaminocarbonyl-1-methyl-ethyl)-4-methyl-quinolin-2-yl]-oxo}-benzamidine-hydrochloride Yield: 14.8% of theory, $C_{25}H_{28}N_4O_4 \times HCl$ (448.52/484.98); mass spectrum: $(M+H)^+=449$.

(4) 4-[(7-methoxycarbonyl-4-methyl-quinolin-2-yl)-oxo]-benzamidine-hydrochloride Yield: 86% of theory, $C_{19}H_{17}N_3O_3 \times HCl$ (335.37/371.83); mass spectrum: $(M+H)^+=336$.

(5) 4-{[7-(N-(2-ethoxycarbonyl-ethyl)-N-(pyridine-2-yl)-aminocarbonyl)-4-methyl-quinolin-2-yl]-oxo}-benzamidine-hydrochloride Yield: 61% of theory, $C_{28}H_{27}N_5O_4 \times HCl$ (497.56/534.03); mass spectrum: $(M+H)^+=498$; $(M+2H)^{++}=249.6$.

EXAMPLE 30

4-{[7-(2-methyl-phenyl)-4-methyl-quinolin-2-yl]-amino}-benzamidine-hydrochloride a. 4-[(7-bromo-4-methyl-quinolin-2-yl)-amino]-benzonitrile 17.7 g (0.069 mol) of 7-bromo-2-chloro-4-methyl-quinoline and 9.0 g (0.076 mol) of 4-aminobenzonitrile are refluxed in 150 ml glacial acetic acid for 5 hours. The solvent is distilled off, the residue is stirred with water and made alkaline with ammonia. The crude product is suction filtered and then chromatographed on silica gel, eluting with methylene chloride/ethanol (99:1 and 98:2).

Yield: 17.5 g (75% of theory), $R_f$ value: 0.41 (silica gel; methylene chloride/ethanol=98:2).

b. 4-{[7-(2-methyl-phenyl)-4-methyl-quinolin-2-yl]-amino}-benzonitrile

Prepared analogously to Example 27e from 4-[(7-bromo-4-methyl-quinolin-2-yl)-amino]-benzonitrile, 2-methylphenylboric acid, tetrakis-(triphenylphosphine)-palladium (0) and sodium carbonate in toluene/water.

Yield: 68% of theory, $R_f$ value: 0.21 (silica gel; petroleum ether/ethyl acetate=4:1).

c. 4-{[7-(2-methyl-phenyl)-4-methyl-quinolin-2-yl]-amino}-benzamidine-hydrochloride Prepared analogously to Example 1f from 4-{[7-(2-methyl-phenyl)-4-methyl-quinolin-2-yl]-amino}-benzonitrile and hydrochloric acid/ammonium carbonate in ethanol.

Yield: 68.4% of theory, $C_{24}H_{22}N_4 \times HCl$ (366.47/402.93); mass spectrum: $M^+=366$.

The following compounds are prepared analogously:
(1) 4-{[7-(N-ethoxycarbonylmethylcarbonyl-N-ethyl-amino)-4-methyl-quinolin-2-yl]-amino}-benzamidine-hydrochloride Yield: 2.3% of theory, $C_{24}H_{28}N_6O_3 \times HCl$ (448.52/484.99); mass spectrum: $(M+H)^+=449$.

(2) 4-[(7-acetyl-4-methyl-quinolin-2-yl)-amino]-benzamidine-hydrochloride

Yield: 100% of theory, $C_{19}H_{18}N_4O \times HCl$ (318.39/354.85); mass spectrum: $(M+H)^+=319$.

(3) 4-[(7-bromo-4-methyl-quinolin-2-yl)-amino]-benzamidine-hydrochloride

Yield: 77.9% of theory, $C_{17}H_{15}BrN_4 \times HCl$ (355.26/391.72); mass spectrum: $(M+H)^+=355/7$ (Br).

EXAMPLE 31

4-{[7-(4-carboxy-phenyl)-4-methyl-quinolin-2-yl]-oxo}-benzamidine-hydrochloride 250 mg (0.5 mmol) of 4-{[7-(4-ethoxycarbonyl-phenyl)-4-methyl-quinolin-2-yl]-oxo}-benzamidine-hydrochloride are stirred in 6 ml of 1-molar lithium hydroxide solution and 6 ml of tetrahydrofuran for 5 hours at ambient temperature and combined with 10 ml of 1N hydrochloric acid. The organic solvent is distilled off, 10 ml ammonium chloride solution are added and the mixture is stirred overnight at ambient temperature. The product precipitated is suction filtered and dried.

Yield: 140 mg (60% of theory), $C_{24}H_{19}N_3O_3 \times HCl$ (397.44/433.9); mass spectrum: $(M+H)^+=398$.

EXAMPLE 32

4-{[7-((E/Z)-2-ethoxycarbonyl-2-methyl-ethylenyl)-4-methyl-quinolin-2-yl]-oxo}-benzamidine-hydrochloride a. 4-{[7-((E/Z)-2-ethoxycarbonyl-2-methyl-ethylenyl)-4-methyl-quinolin-2-yl]-oxo}-benzonitrile 1.7 g (5 mmol) of 4-[(7-bromo-4-methyl-quinolin-2-yl)-oxo]-benzonitrile, 0.71 g (6,25 mmol) of ethyl methacrylate, 1.3 g (12.5 mmol) of triethylamine, 0.26 g (0.1 mmol) of triphenylphosphine and 0.11 g (0.05 mmol) of palladium (II)-acetate are heated to 120° C. in 10 ml xylene under a nitrogen atmosphere for 7 hours. Then the mixture is cooled, diluted with water and extracted with ethyl acetate. The organic phases are dried and evaporated down. The residue is chromatographed on silica gel and eluted with petroleum ether/ethyl acetate (4:1). The desired fractions are combined and evaporated down.

Yield: 0.48 g (25.8% of theory), $R_f$ value: 0.55 (silica gel; petroleum ether/ethyl acetate=4:1).

b. 4-{[7-((E/Z)-2-ethoxycarbonyl-2-methyl-ethylenyl)-4-methyl-quinolin-2-yl]-oxo}-benzamidine-hydrochloride Prepared analogously to Example 1f from 4-{[7-((E/Z)-2-ethoxycarbonyl-2-methyl-ethylenyl)-4-methyl-quinolin-2-yl]-oxo}-benzonitrile and hydrochloric acid/ammonium carbonate in ethanol.

Yield: 78.8% of theory, $C_{23}H_{23}N_3O_3 \times HCl$ (389.46/425.92); mass spectrum: $(M+H)^+=390$.

The following compound is prepared analogously:
(1) 4-{[7-((E)-2-ethoxycarbonyl-1-methyl-ethylenyl)-4-methyl-quinolin-2-yl]-oxo}-benzamidine-hydrochloride Yield: 24% of theory, $C_{23}H_{23}N_3O_3 \times HCl$ (389.46/425.92); mass spectrum: $(M+H)^+=390$.

EXAMPLE 33

4-[(7-ethoxycarbonylmethyl-4-methyl-quinolin-2-yl)-oxo]-benzamidine-hydrochloride a. 4-[(7-allyl-4-methyl-quinolin-2-yl)-oxy]-benzonitrile 6.8 g (0.02 mol) of 4-[(7-bromo-4-methyl-quinolin-2-yl)-oxy]-benzonitrile, 6.8 g (5.9 mmol) of tetrakis-(triphenylphosphine)-palladium (0) and 6.8 ml (0.022 mol) of allyltributyltin are refluxed in 50 ml toluene under a nitrogen atmosphere for 2 hours. The toluene is distilled off, the residue triturated with ether and suction filtered. The mother liquor is combined with silica gel and evaporated down. Then the mixture is chromatographed on silica gel and eluted with cyclohexane/ethyl acetate (95:5 and 9:1). The desired fractions are combined and evaporated down.

Yield: 6.0 g (88% of theory), $R_f$ value: 0.51 (silica gel; petroleum ether/ethyl acetate=4:1).

b. 4-[(7-ethoxycarbonylmethyl-4-methyl-quinolin-2-yl)-oxo]-benzonitrile 3 g (0.01 mol) of 4-[(7-allyl-4-methyl-quinolin-2-yl)-oxy]-benzonitrile are dissolved in 50 ml methylene chloride and 40 ml acetonitrile and combined with a solution of 15.7 g (0.073 mol) of sodium periodate and 50 mg of ruthenium trichloride in 90 ml water with stirring. After 24 hours at ambient temperature the mixture is diluted with water and extracted with methylene chloride. The organic extracts are dried and evaporated down. The residue is chromatographed on silica gel and eluted with methylene chloride/ethanol (1:0 and 50:1). The desired fractions are combined and evaporated down.

Yield: 1.25 g (40% of theory), $R_f$ value: 0.12 (silica gel; methylene chloride/ethanol=30:1).

c. 4-[(7-ethoxycarbonylmethyl-4-methyl-quinolin-2-yl)-oxo]-benzamidine-hydrochloride Prepared analogously to Example 1f from 4-[(7-ethoxycarbonylmethyl-4-methyl-quinolin-2-yl)-oxo]-benzonitrile and hydrochloric acid/ammonium carbonate in ethanol.

Yield: 43% of theory, $C_{21}H_{21}N_3O_3 \times HCl$ (363.42/399.89); mass spectrum: $(M+H)^+=364$;

The following compounds are prepared analogously:
(1) 4-[(7-allyl-4-methyl-quinolin-2-yl)-oxo]-benzamidine-hydrochloride Yield: 88% of theory, $C_{20}H_{19}N_3O \times HCl$ (317.4/353.86); mass spectrum: $(M+H)^+=318$.

(2) 4-{[7-(1-ethoxycarbonyl-cyclopentyl)-4-methyl-quinolin-2-yl]-oxo}-benzamidine-hydrochloride Yield: 88% of theory, $C_{25}H_{27}N_3O_3 \times HCl$ (417.52/453.98); mass spectrum: $(M+H)^+=418$.

(3) 4-{[7-(1-hydroxy-but-3-yl-4-yl)-4-methyl-quinolin-2-yl]-oxo}-benzamidine-hydrochloride Yield: 47.2% of theory, $C_{21}H_{19}N_3O_2 \times HCl$ (345.4/381.86); mass spectrum: $(M+H)^+=346$.

(4) 4-{[7-(1-methoxycarbonyl-1-methyl-ethyl)-4-methyl-quinolin-2-yl]-oxo}-benzamidine-hydrochloride Yield: 72% of theory, $C_{22}H_{23}N_3O_3 \times HCl$ (377.45/413.92); mass spectrum: $(M+H)^+=378$.

(5) 4-{[7-(1-ethoxycarbonyl-propyl)-4-methyl-quinolin-2-yl]-oxo}-benzamidine-hydrochloride Yield: 81% of theory, $C_{23}H_{25}N_3O_3 \times HCl$ (391.48/427.94); mass spectrum: $(M+H)^+=392$.

(6) 4-{[7-(Bis-ethoxycarbonyl-methyl)-4-methyl-quinolin-2-yl]-oxo}-benzamidine-hydrochloride Yield: 91% of theory, $C_{24}H_{25}N_3O_5 \times HCl$ (435.49/471.95); mass spectrum: $(M+H)^+=436$.

(7) 4-{[7-(1-aminocarbonyl-1-methyl-ethyl)-4-methyl-quinolin-2-yl]-oxo}-benzamidine-hydrochloride Yield: 87% of theory, $C_{21}H_{22}N_4O_2 \times HCl$ (362,44/398.9); mass spectrum: $(M+H)^+=363$.

(8) 4-{[7-(1-(N-(2-hydroxyethyl)-aminocarbonyl)-1-methyl-ethyl)-4-methyl-quinolin-2-yl]-oxo}-benzamidine-hydrochloride Yield: 82% of theory, $C_{23}H_{26}N_4O_3 \times HCl$ (406.49/442.96); mass spectrum: $(M+H)^+=407$.

(9) 4-{[7-(1-ethoxycarbonylmethylaminocarbonyl-1-methyl-ethyl)-4-methyl-quinolin-2-yl]-oxo}-benzamidine-hydrochloride Yield: 44% of theory, $C_{25}H_{28}N_4O_4 \times HCl$ (448.53/485.0); mass spectrum: $M^+=448$.

(10) 4-{[7-(cyclopenten-1-yl)-4-methyl-quinolin-2-yl]-oxo}-benzamidine-hydrochloride Yield: 92% of theory, $C_{22}H_{21}N_3O \times HCl$ (343.3/379.9); mass spectrum: $(M+H)^+=344$.

(11) 4-{[7-(1-(N-(2-ethoxycarbonyl-ethylcarbonyl)-amino)-1-methyl-ethyl)-4-methyl-quinolin-2-yl]-oxo}-benzamidine-hydrochloride Yield: 91% of theory, $C_{26}H_{30}N_4O_4 \times HCl$ (462.56/499.02); mass spectrum: $(M+H)^+=463$.

EXAMPLE 34

4-{[7-(2-methyl-5-ethoxycarbonyl-phenyl)-4-methyl-quinolin-2-yl]-oxo}-benzamidine-hydrochloride a. 4-carboxy-2-methyl-phenylboric acid 11.3 ml (18 mmol) of n-butyllithium (1.6 molar in hexane) are added dropwise to a solution of 0.9 g (4 mmol) of 3-bromo-4-methyl-benzoic acid in 15 ml n-hexane under a nitrogen atmosphere at −78° C. After 1 hour at −78° C., 0.6 ml (5 mmol) of trimethylborate is added dropwise. After a further 2 hours at −78° C., the reaction mixture is heated to ambient temperature and combined with ethyl acetate and ice water. Then it is acidified with hydrochloric acid, the organic phase is separated off, dried and evaporated down.

Yield: 0.43 g (60% of theory), $R_f$ value: 0.1 (silica gel; cyclohexane/ethyl acetate=1:1).

b. 4-{[7-(2-methyl-5-carboxy-phenyl)-4-methyl-quinolin-2-yl]-oxo}-benzonitrile

A solution of 0.75 g (2.2 mmol) of 4-[(7-bromo-4-methyl-quinolin-2-yl)oxy]-benzonitrile and 75 mg (0.064 mmol) of tetrakis-(triphenylphosphine)-palladium (0) in 9 ml toluene are combined under a nitrogen atmosphere with a solution of 0.47 g (4.4 mmol) of sodium carbonate in 3 ml water and 0.4 g (2.2 mmol) of 4-carboxy-2-methyl-phenylboric acid in 5 ml methanol and stirred for 4 hours at 95° C. After 12 hours at ambient temperature the reaction mixture is mixed with ice water, adjusted to pH 5 with glacial acetic acid and extracted with ethyl acetate. The organic phase is washed with sodium hydrogen carbonate, dried and evaporated down. The residue is chromatographed on silica gel and eluted with methylene chloride/ethanol (1:0, 100:1 and 30:1). The desired fractions are combined and evaporated down.

Yield: 0.13 g (15% of theory), $R_f$ value: 0.36 (silica gel; cyclohexane/ethyl acetate=1:1).

c. 4-{[7-(2-methyl-5-ethoxycarbonyl-phenyl)-4-methyl-quinolin-2-yl]-oxo}-benzamidine-hydrochloride Prepared analogously to Example 1f from 4-{[7-(2-methyl-5-carboxy-phenyl)-4-methyl-quinolin-2-yl]-oxo}-benzonitrile and hydrochloric acid/ammonium carbonate in ethanol.

Yield: 75% of theory, $C_{27}H_{25}N_3O_3 \times HCl$ (439.52/475.99); mass spectrum: $(M+H)^+=440$.

The following compound is prepared analogously:

(1) 4-{[7-(2-methyl-5-ethoxycarbonylmethylaminocarbonyl-phenyl)-4-methyl-quinolin-2-yl]-oxo}-benzamidine-hydrochloride Yield: 90% of theory, $C_{29}H_{28}N_4O_4 \times HCl$ (496.58/533.04); mass spectrum: $(M+H)^+=497$.

EXAMPLE 35

4-[(7-acetylamino-4-methyl-quinolin-2-yl)-oxo]-benzamidine-hydrochloride 225 mg (6.9 mmol) of 4-[(7-amino-4-methyl-quinolin-2-yl)-oxo]-benzamidine-hydrochloride are refluxed with 2 ml methanol and 10 ml acetic anhydride for 40 minutes. The solution is cooled, diluted with ether, the precipitate is suction filtered and dried.

Yield: 90 mg (29.7% of theory), $C_{19}H_{18}N_4O_2 \times HCl$ (334.38/370.84); mass spectrum: $(M+H)^+=335$.

EXAMPLE 36

4-{[7-(3-ethoxycarbonylmethyl-4,5-dihydroimidazol-2-on-1-yl)-4-methyl-quinolin-2-yl]-oxo}-benzamidine-hydrochloride a. 4-{[7-(2-chlorethylaminocarbonylamino)-4-methyl-quinolin-2-yl)-oxo]-benzonitrile 2.25 g (8.5 mmol) of 4-[(7-amino-4-methyl-quinolin-2-yl)-oxo]-benzonitrile are dissolved in 25 ml dimethylformamide and after the addition of 2.25 g (21 mmol) of chloroethyl isocyanate the mixture is stirred for 20 hours at ambient temperature. Then it is stirred into ice water and extracted with ethyl acetate. The organic extracts are washed with sodium chloride solution, dried, combined with silica gel and evaporated down. Then the mixture is chromatographed on silica gel and eluted with ethyl acetate/petroleum ether (1:9 and 3:7). The desired fractions are combined and evaporated down.

Yield: 1.8 g (56 Q% of theory); $R_f$ value: 0.61 (silica gel; methylene chloride/ethanol=19:1).

b. 4-{[7-(4,5-dihydroimidazol-2-on-1-yl)-4-methyl-quinolin-2-yl]-oxo}-benzonitrile 1.8 g (6 mmol) of 4-{[(7-(2-chloroethylaminocarbonylamino)-4-methyl-quinolin-2-yl]-oxo}-benzonitrile are dissolved in 75 ml tert.butanol and combined batchwise with 1.1 g (0.01 mol) of potassium-tert.butoxide. Then the mixture is stirred for a further 1 hour, the precipitate formed is suction filtered, washed with 2N acetic acid and water and dried.

Yield: 1.55 g (75% of theory), $R_f$ value: 0.57 (silica gel; methylene chloride/ethanol=19:1).

c. 4-{[7-((3-ethoxycarbonylmethyl-4,5-dihydroimidazol-2-on-1-yl)-4-methyl-quinolin-2-yl]-oxo}-benzonitrile 1.5 g (6.1 mmol) of 4-{[7-(4,5-dihydroimidazol-2-on-1-yl)-4-methyl-quinolin-2-yl]-oxo}-benzonitrile and 3.6 g (0.026 mol) of potassium carbonate are taken up in 250 ml acetone and refluxed. After 30 minutes 3.2 g (0.02 mol) of ethyl bromoacetate are added. The reaction mixture is refluxed for 30 hours, then, after cooling, it is filtered and evaporated down. The residue is chromatographed on silica gel and eluted with methylene chloride/ethanol (1:0 and 50:1). The desired fractions are combined and evaporated down.

Yield: 675 mg (56.8% of theory).

d. 4-{[7-(3-ethoxycarbonylmethyl-4,5-dihydroimidazol-2-on-1-yl)-4-methyl-quinolin-2-yl]-oxo}-benzamidine-hydrochloride Prepared analogously to Example 1f from 4-{[7-(3-ethoxycarbonylmethyl-4,5-dihydroimidazol-2-on-1-yl)-4-methyl-quinolin-2-yl]-oxo}-benzonitrile and hydrochloric acid/ammonium carbonate in ethanol.

Yield: 41.5% of theory, $C_{24}H_{25}N_5O_4 \times HCl$ (447.49/483.97); mass spectrum: $(M+H)^+$ 448.

EXAMPLE 37

4-{[7-(1-ethoxycarbonylmethyloxyimino-ethylene)-4-methyl-quinolin-2-yl]-amino}-benzamidine-hydrochloride a. 4-{[7-(1-ethoxy-vinyl)-4-methyl-quinolin-2-yl]amino}-benzonitrile 6.8 g (0.02 mol) of 4-(7-bromo-4-methyl-quinolin-2-yl)-amino-benzonitrile are dissolved in 40 ml of dimethylformamide at 100° C. and after the addition of 7.2 g (0.02 mol) of (1-ethoxy-vinyl)-tributyltin and 0.7 g of bis(triphenylphosphine)-palladium (II)-chloride the mixture is stirred for 5 hours at 100° C. Then it is evaporated down, the residue is combined with 400 ml of saturated methanolic potassium fluoride solution and stirred overnight at ambient temperature. The methanol is distilled off and the residue chromatographed on silica gel, eluting with petroleum ether/ethyl acetate (9:1). The desired fractions are combined and evaporated down.

Yield: 4.6 g (69.8% of theory), $R_f$ value: 0.54 (silica gel; petroleum ether/ethyl acetate=2:1).

b. 4-[(7-acetyl-4-methyl-quinolin-2-yl)amino]-benzonitrile 3.2 g (0.01 mol) of 4-{[7-(1-ethoxy-vinyl)-4-methyl-quinolin-2-yl]amino}-benzonitrile are dissolved in 85 ml acetone and after the addition of 21 ml of 1N hydrochloric acid the mixture is stirred overnight at ambient temperature. The crystalline precipitate is diluted with water, suction filtered and dried.

Yield: 2.3 g (78.5% of theory), $R_f$ value: 0.42 (silica gel; methylene chloride/ethanol=95:5).

c. 4-{[7-(1-carboxymethyloxyimino-ethylene)-4-methyl-quinolin-2-yl]-amino}-benzonitrile 300 mg (1.0 mmol) of 4-[(7-acetyl-4-methyl-quinolin-2-yl)-amino]-benzonitrile, 330 mg (1.5 mmol) of carboxymethoxyamine and 0.21 ml (1.5 mmol) of triethylamine are refluxed for 3 hours in 20 ml methanol and 10 ml toluene after the addition of 3 g each of molecular sieve 3A and 4A. The solvent is distilled off and the residue is chromatographed on silica gel, eluting with methylene chloride/ethanol (4:1).

Yield: 370 mg (100% of theory), $R_f$ value: 0.23 (silica gel; methylene chloride/ethanol 4:1).

d. 4-{[7-(1-ethoxycarbonylmethyloxyimino-ethylene)-4-methyl-quinolin-2-yl)-amino]-benzamidine-hydrochloride Prepared analogously to Example if from 4-{[7-(1-ethoxycarbonylmethyloxyimino-ethylene)-4-methyl-quinolin-2-yl)-amino]-benzonitrile and hydrochloric acid/ammonium carbonate in ethanol.

Yield: 41% of theory, $C_{23}H_{25}N_5O_3 \times HCl$ (419.49/455.88); mass spectrum: $(M+H)^+$=420.

EXAMPLE 38

4-[(6-ethoxycarbonylmethyloxy-4-methyl-quinolin-2-yl)-oxo]-benzamidine-hydrochloride a. 2-chloro-6-hydroxy-4-methyl-quinoline 22.1 g (0.106 mol) of 2-chloro-6-methoxy-4-methyl-quinoline are refluxed for 4 hours in 210 ml of 48% hydrobromic acid. After cooling the precipitate formed is suction filtered, washed and dried.

Yield: 20.5 g (100% of theory), $R_f$ value: 0.72 (silica gel; methylene chloride/ethanol=9:1).

b. 2-chloro-6-ethoxycarbonylmethyloxy-4-methyl-quinoline 2.0 g (10.3 mmol) of 2-chloro-6-hydroxy-4-methyl-quinoline are dissolved in 10 ml dimethylformamide and after the addition of 1.7 g (12 mmol) of potassium carbonate and 1.3 ml (12 mmol) of ethyl bromoacetate the mixture is refluxed under a nitrogen atmosphere for 4 hours. The solvent is distilled off, the residue is triturated with water, suction filtered and dried.

Yield: 2.6 g (80% of theory), $R_f$ value: 0.65 (silica gel; methylene chloride/ethanol=95:5).

c. 4-[(6-ethoxycarbonylmethyloxy-4-methyl-quinolin-2-yl)-oxo]-benzonitrile

Prepared analogously to Example 27d from 2-chloro-6-ethoxycarbonylmethyloxy-4-methyl-quinoline, 4-hydroxybenzonitrile and potassium carbonate in dimethylformamide at 170° C.

Yield: 29% of theory, $R_f$ value: 0.51 (silica gel; methylene chloride/ethanol/glacial acetic acid=95:5:0.01).

d. 4-[(6-ethoxycarbonylmethyloxy-4-methyl-quinolin-2-yl)-oxo]-benzamidine-hydrochloride Prepared analogously to Example 1f from 4-[(6-ethoxycarbonylmethyloxy-4-methyl-quinolin-2-yl)-oxo]-benzonitrile and hydrochloric acid/ammonium carbonate in ethanol.

Yield: 14.2% of theory, $C_{21}H_{21}N_3O_4 \times HCl$ (379.42/415.89); mass spectrum: $M^+$=379.

EXAMPLE 39

4-[(4-methylamino-quinazolin-2-yl)-methyl]-benzamidine-acetate a. 2-[2-(4-cyano-phenyl)-acetylamino]-benzamide 11.8 g (0.06 mol) of 4-cyanophenylacetic acid chloride are dissolved in 250 ml chlorobenzene and after the addition of 8.2 g (0.06 mol) of anthranilic acid amide the mixture is refluxed for 2 hours. After cooling it is diluted with water and the crystalline precipitate is suction filtered.

Yield: 10.5 g (63% of theory), $R_f$ value: 0.63 (silica gel; methylene chloride/ethanol=19:1).

b. 4-[(4-oxo-3,4-dihydroquinazolin-2-yl)methyl]-benzonitrile 9.9 g (0.034 mol) of 2-[2-(4-cyano-phenyl)-acetylamino]-benzamide are dissolved in a solution of 3.9 g sodium in 400 ml ethanol and refluxed for 1 hour. The solvent is distilled off down to 100 ml, the residue is diluted with ice water and neutralised with hydrochloric acid. The crystalline precipitate is suction filtered and dried.

Yield: 6.9 g (74.8% of theory), $R_f$ value: 0.44 (silica gel; methylene chloride/ethanol=19:1).

c. 4-[(4-chloro-quinazolin-2-yl)-methyl]-benzonitrile

Prepared analogously to Example 27c from 4-[(4-oxo-3,4-dihydroquinazolin-2-yl)methyl]-benzonitrile and phosphorus oxychloride.

Yield: 51.2% of theory, $R_f$ value: 0.72 (silica gel; methylene chloride/ethanol=19:1).

d. 4-[(4-methylamino-quinazolin-2-yl)-methyl]-benzonitrile

Prepared analogously to Example 12c from 4-[(4-chloro-quinazolin-2-yl)methyl]-benzonitrile, methylamine solution and isopropanol at 100° C.

Yield: 86.5% of theory, $R_f$ value: 0.58 (silica gel; methylene chloride/ethanol=8:2).

e. 4-[(4-methylamino-quinazolin-2-yl)-methyl]-benzamidine-acetate

Prepared analogously to Examples 23a and 23b from 4-[(4-methylamino-quinazolin-2-yl)-methyl]-benzonitrile, hydroxylamine in methanol and palladium on activated charcoal in acetic acid.

Yield: 21.8% of theory, $C_{17}H_{17}N_5 \times CH_3COOH$ (291.35/351.4); mass spectrum: $(M+H)^+=292$.

EXAMPLE 40

4-[(4-methyl-quinazolin-2-yl)-aminol-benzamidine-hydrochloride a. 4-methyl-1H-quinazolin-2-one 17.4 g (0.128 mol) of 2-amino-acetophenone are dissolved in 250 ml glacial acetic acid and combined within 1 hour with a solution of 12.5 g (0.155 mol) of potassium cyanate in 50 ml water and stirred for 60 hours at ambient temperature. The precipitate is suction filtered, dried, dissolved in 170 ml conc. hydrochloric acid, combined with 950 ml water and stirred for 12 hours at 5° C. Then the mixture is adjusted to pH 7 with sodium hydroxide solution at 5 to 10° C., the crystalline precipitate is suction filtered and dried.

Yield: 3.85 g (18.8% of theory), $C_9H_8N_2O$ (160.2); mass spectrum: $M^+=160$.

b. 2-chloro-4-methyl-quinazoline

Prepared analogously to Example 27c from 4-methyl-1H-quinazolin-2-one and phosphorus oxychloride in hydrochloric acid.

Yield: 67% of theory, $R_f$ value: 0.81 (silica gel; petroleum ether/ethyl acetate=7:3).

c. 4-[(4-methyl-quinazolin-2-yl)-amino]-benzonitrile

Prepared analogously to Example 30a from 2-chloro-4-methyl-quinazoline and 4-aminobenzonitrile in glacial acetic acid.

Yield: 15.9% of theory, d. 4-[(4-methyl-quinazolin-2-yl)-amino]-benzamidine-hydrochloride Prepared analogously to Example if from 4-[(4-methyl-quinazolin-2-yl)-amino]-benzonitrile and hydrochloric acid/ammonium carbonate in ethanol.

Yield: 24.8% of theory, $C_{16}H_{15}N_5 \times HCl$ (277.33/313.79); mass spectrum: $M^+=277$.

EXAMPLE 41

4-[(7-bromo-4-methyl-quinoxalin-2-on-3-yl)-amino]-benzamidine-hydrochloride a. 5-bromo-2-methylamino-nitrobenzene Prepared analogously to Example 7a from 2,5-dibromo-nitrobenzene and methylamine solution in ethanol.

Yield: 92.8% of theory, $R_f$ value: 0.45 (silica gel; ethyl acetate/petroleum ether=1:9).

b. 5-bromo-2-methylamino-aniline

Prepared analogously to Example 3d from 5-bromo-2-methylamino-nitrobenzene and Raney nickel/hydrogen in ethyl acetate/ethanol.

Yield: 76.7% of theory, $R_f$ value: 0.55 (silica gel; methylene chloride/ethanol=19:1).

c. 6-bromo-1-methyl-1,4-dihydro-quinoxalin-2,3-dione 360 mg (4.12 mmol) of oxalic acid dichloride are placed in 30 ml of o-dichlorobenzene and comb ined batchwise with 760 mg (3.8 mmol) of 5-bromo-2-methylamino-aniline at 60° C. Then the mixture is stirred for 30 minutes at 60° C. and for 60 minutes at 130° C. After cooling the crystalline product is suction filtered and washed with ether.

Yield: 650 mg (67.7% of theory), $R_f$ value: 0.3 (silica gel; methylene chloride/ethanol=19:1).

d. 6-bromo-3-chloro-1-methyl-1H-quinoxalin-2-one

Prepared analogously to Example 27c from 6-bromo-1-methyl-1,4-dihydro-quinoxalin-2,3-dione and phosphorus oxychloride.

Yield: 64.5% of theory, $R_f$ value: 0.8 (silica gel; methylene chloride/ethanol=19:1).

e. 4-[(7-bromo-4-methyl-quinoxalin-2-on-3-yl)-amino]-benzonitrile 270 mg (1 mmol) of 6-bromo-3-chloro-1-methyl-1H-quinoxalin-2-one and 240 mg (2 mmol) of 4-aminobenzonitrile are heated to 100° C. in 3 ml methanol. The precipitate is cooled to 40° C., diluted with methanol and suction filtered.

Yield: 350 mg (98.6% of theory), $R_f$ value: 0.28 (silica gel; ethyl acetate/petroleum ether 2:8).

f. 4-[(7-bromo-4-methyl-quinoxalin-2-on-3-yl)-amino]-benzamidine-hydrochloride

Prepared analogously to Example 1f from 4-[(7-bromo-4-methyl-quinoxalin-2-on-3-yl)-amino]-benzonitrile and hydrochloric acid/ammonium carbonate in ethanol.

Yield: 48.5% of theory, $C_{16}H_{14}BrN_5O \times HCl$ (372.23/408.69); mass spectrum: $(M+H)^+=372/4$ (Br).

EXAMPLE 42

4-[(7-amino-4-methyl-1,8-naphthyridin-2-yl)-oxy]-benzamidine-hydrochloride a. 7-amino-4-methyl-1H-[1,8]naphthyridin-2-one 20 g (0.184 mol) of 2,6-diaminopyridine are refluxed in 28 g (0.215 mol) of ethyl acetate for 2 hours using a water separator. After cooling the crystalline precipitate is suction filtered, washed with ether and dried.

Yield: 18.5 g (46.2% of theory), $C_9H_9N_3O \times HCl$ (175.2/211.66); mass spectrum: $M^+=175$.

b. 2-chloro-4-methyl-7-amino-[1,8]naphthyridine

Prepared analogously to Example 27c from 7-amino-4-methyl-1H-[1,8]naphthyridin-2-one and phosphorus oxychloride.

Yield: 95.5% of theory, $R_f$ value: 0.38 (silica gel; methylene chloride/ethanol=9:1).

c. 4-[(7-amino-4-methyl-1,8-naphthyridin-2-yl)-oxy]-benzonitrile

Prepared analogously to Example 27d from 2-chloro-4-methyl-7-amino-[1,8]naphthyridine and 4-hydroxybenzonitrile.

Yield: 37.9% of theory, $R_f$ value: 0.76 (silica gel; methylene chloride/ethanol/glacial acetic acid=4:1: 0.01).

d. 4-[(7-amino-4-methyl-1,8-naphthyridin-2-yl)-oxy]-benzamidine-hydrochloride

Prepared analogously to Example 1f from 4-[(7-amino-4-methyl-1,8-naphthyridin-2-yl)-oxy]-benzonitrile and hydrochloric acid/ammonium carbonate in ethanol.

Yield: 52.8% of theory, $C_{16}H_{15}N_5O \times HCl$ (293.3/329.76); mass spectrum: $(M+H)^+=294$.

The following compounds are prepared analogously:

(1) 4-{[7-(4-ethoxycarbonyl-n-butylamino)-4-methyl-1,8-naphthyridin-2-yl]-oxy}-benzamidine-hydrochloride Yield: 24.2% of theory, $C_{23}H_{27}N_5O_3 \times HCl$ (421.5/457.96); mass spectrum: $(M+H)^+=422$.

(2) 4-[(7-acetylamino-4-methyl-1,8-naphthyridin-2-yl)-oxy]-benzamidine-hydrochloride Yield: 44.4% of theory, $C_{18}H_{17}N_5O_2 \times HCl$ (335.36/371.87); mass spectrum: $(M+H)^+=336$.

EXAMPLE 43

4-[(7-bromo-4-methyl-3-oxo-3,4-dihydro-pyrido[2,3-b]-pyrazin-2-yl)methyl]-benzamidine-hydrochloride a. 5-bromo-3-nitro-pyridine-2-ol-hydrobromide 3.6 ml of bromine are added dropwise to a suspension of 10.0 g (0.071 mol) of 2-hydroxy-3-nitro-pyridine in 25 ml of carbon tetrachloride whilst cooling with ice. The reaction mixture is refluxed for 2 hours. The solvent is distilled off in vacuo, the crystalline product is suction filtered and recrystallised from water.

Yield: 7.5 g (35.1% of theory).

b. 5-bromo-2-chloro-3-nitro-pyridine

Prepared analogously to Example 27c from 5-bromo-3-nitro-pyridine-2-ol-hydrobromide and phosphorus oxychloride/phosphorus pentachloride by refluxing.

Yield: 53.5% of theory, $R_f$ value: 0.77 (silica gel; methylene chloride/ethanol=4:1).

c. 5-bromo-3-nitro-2-methylamino-pyridine

Prepared analogously to Example 12c from 5-bromo-2-chloro-3-nitro-pyridine, methylamine solution and isopropanol at 100° C.

Yield: 83% of theory, $R_f$ value: 0.51 (silica gel; methylene chloride/ethanol=19:1).

d. 3-amino-5-bromo-2-methylamino-pyridine

Prepared analogously to Example 3d from 5-bromo-3-nitro-2-methylamino-pyridine and Raney nickel/hydrogen in ethyl acetate.

Yield: 92.5% of theory, $R_f$ value: 0.18 (silica gel; methylene chloride/ethanol=19:1).

e. 4-[(7-bromo-4-methyl-3-oxo-3,4-dihydro-pyrido[2,3-b]-pyrazin-2-yl)methyl]-benzonitrile Prepared analogously to Example 7f from 3-amino-5-bromo-2-methylamino-pyridine and 3-(4-cyano-phenyl)-2-oxo-propionic acid in ethanol.

Yield: 26.2% of theory, $R_f$ value: 0.68 (silica gel; methylene chloride/ethanol/glacial acetic acid=4:1:0,01).

f. 4-[(7-bromo-4-methyl-3-oxo-3,4-dihydro-pyrido[2,3-b]-pyrazin-2-yl)methyl]-benzamidine-hydrochloride Prepared analogously to Example 1f from 4-[(7-bromo-4-methyl-3-oxo-3,4-dihydro-pyrido[2,3-b]pyrazin-2-yl)methyl]-benzonitrile and hydrochloric acid/ammonium carbonate in ethanol.

Yield: 20.5% of theory, $C_{16}H_{14}BrN_5O \times HCl$ (372.22/408.72); mass spectrum: $(M+H)^+=372/4$ (Br).

EXAMPLE 44

4-[(6-chloro-1-methyl-2-oxo-1,2-dihydro-pyrido[2,3-b]-pyrazin-3-yl)methyl]-benzamidine-hydrochloride a. 2-amino-3-benzyloxycarbonylamino-6-chloro-pyridine 1.2 g (8.8 mmol) of 2,3-diamino-6-chloro-pyridine are dissolved in 20 ml tetrahydrofuran and, after the addition of 2 ml pyridine at 0° C., mixed with 2 ml of benzyl chloroformate. After heating to ambient temperature the mixture is combined with ice water, adjusted to pH 4 with glacial acetic acid and extracted with ethyl acetate. The combined organic extracts are dried and evaporated down. The residue is chromatographed on silica gel and eluted with petroleum ether/ethyl acetate (9:1 and 1:1).

Yield: 0.55 g (22.5% of theory), $R_f$ value: 0.62 (silica gel; ethyl acetate/petroleum ether=1:1).

b. 2-amino-3-methylamino-6-chloro-pyridine 7.0 g (25.4 mmol) of benzyl (2-amino-4-chlorophenyl)-carbaminate are dissolved in 250 ml tetrahydrofuran, combined batchwise with 3.8 g (0.1 mol) of lithium aluminium hydride and then refluxed for 15 minutes. The mixture is then combined with ice water, a djusted to pH 4 with glacial acetic acid, filtered over kieselguhr and extracted with ethyl acetate. The combined organic extracts are dried and evaporated down. The residue is chromatographed on silica gel and eluted with petroleum ether/ethyl acetate (9:1, 8:2 and 1:1).

Yield: 1.95 g (48.6% of theory), $R_f$ value: 0.35 (silica gel; methylene chloride/ethanol=19:1).

c. 4-[(6-chloro-1-methyl-2-oxo-1,2-dihydro-pyrido[2,3-b]-pyrazin-3-yl)methyl]-benzonitrile Prepared analogously to Example 7f from 2-amino-3-methylamino-2-chloro-pyridine and 3-(4-cyano-phenyl)-2-oxo-propionic acid in ethanol.

Yield: 26.2% of theory, $R_f$ value: 0.66 (silica gel; methylene chloride/ethanol/glacial acetic acid=8:2:0,01).

d. 4-[(6-chloro-1-methyl-2-oxo-1,2-dihydro-pyrido[2,3-b]-pyrazin-3-yl)methl]-benzamidine-hydrochloride Prepared analogously to Example 1f from 4-[(6-chloro-1-methyl-2-oxo-1,2-dihydro-pyrido[2,3-b]pyrazin-3-yl)methyl]-benzonitrile and hydrochloric acid/ammonium carbonate in ethanol.

Yield: 2.5% of theory, $C_{16}H_{14}ClN_5O \times HCl$ (327.78/364.25); mass spectrum: $(M+H)^+=328/30$ (Cl).

EXAMPLE 45

5-{[6-(1-(N-ethoxycarbonylmethylcarbonyl-methylamino)-1-(pyrrolidin-1-yl-carbonyl)-ethyl)-2-oxo-1,2-dihydroquinoxalin-3-yl]-methyl}-benzamidine-hydrochloride a. Methyl 2-(4-chloro-phenyl)-3-hydroxy-2-methyl-propionate 35 ml of a 1.6 molaric solution of n-butyl lithium (61 mmol) in hexane were dropped to a solution of 8.1 ml (85 mmol) of diisopropylamine in 20 ml of tetrahydrofurane at −78° C. Subsequently, a solution of 10.0 g (50 mmol) of methyl 2-(4-chloro-phenyl)-propionate in 30 ml of tetrahydrofurane were dropped into the reaction mixture at −78° C. and subsequenty formaldehyde was introduced as gas at −20° C. within 30 minutes. The reaction mixture was extracted with ethyl acetate after addition of 5 percent citric acid and glacial acetic acid. The organic phase was washed with 1N sulfuric acid, water, saturated sodium bicarbonate solution and sodium chloride solution and died over magnesium sulfate. The raw product was purified over silica gel whereby the eluation was carried out with cyclohexane/ethyl acetate (19:1; 9:1; 4:1; 1:1; and 0:1). The uniform fractions were combined and evaporated down.

Yield: 9.7 g (84% of theory) yellow oil, $R_f$ value: 0.25 (silica gel; petroleum ether/ethyl acetate=4:1).

b. (4-chloro-phenyl)-3-hydroxy-2-methyl-propionic acid

Prepared analogously to Example 10 from methy 2-(4-chloro-phenyl)-3-hydroxy-2-methyl-propionate and sodium hydroxide solution in ethanol.

Yield: 83% of theory, $R_f$ value: 0.55 (silica gel; ethyl acetate/Cyclohexan=2:1+glacial acetic acid).

c. 2-(4-chloro 3-nitro-phenyl)-2-methyl-3-nitrooxy-propionic acid

Prepared analogously to Example 1b aus 2-(4-chlorophenyl)-3-hydroxy-2-methyl-propionic acid and nitric acid.

Yield: 90% of theory, melting point: 129° C.–132° C.; $C_{10}H_9ClN_2O_7$ (304.64).

d. 2-(4-chloro-3-nitro-phenyl)-2-methyl-3-hydroxy-propionic acid

Prepared analogously to Example 14b from 2-(4-chloro-3-nitro-phenyl)-3-nitrooxy-2-methyl-propionic acid and 6N hydrochloric acid in dioxan.

Yield: 98% of theory, $C_{10}H_{10}ClNO_5$ (259.65); mass spectrum: $(M-H)^-=258/60$ (Cl);

$(2M-H)^-=517/9$ (Cl2).

e. 2-[4-(N-benzyl-methylamino)-3-nitro-phenyl]-2-methyl-3-hydroxy-propionic acid Prepared analogously to Example 7a from 2-(4-chloro-3-nitro-phenyl)-3-hydroxy-2-methyl-propionic acid and N-methyl-benzylamine.

Yield: 81% of theory, $C_{18}H_{20}ClN_2O_5$ (344.37); mass spectrum: $M^+$=344.

f. 2-[4-(N-benzyl-methylamino)-3-nitro-phenyl]-2-methyl-3-hydroxy-(1-pyrrolidin-1-yl-propan-1-one Prepared analogously to Example 2a from 2-[4-(N-benzyl-methylamino)-3-nitro-phenyl]-3-hydroxy-2-methyl-propionic acid and pyrrolidine.

Yield: 96% of theory, $C_{22}H_{27}N_3O_4$ (397.48); mass spectrum: $M^+$=398;

$(M+Na)^+$=420.

g. 2-[4-(N-benzyl-methylamino)-3-nitro-phenyl]-2-methyl-3-methanesulfonyloxy-1-pyrrolidin-1-yl-propan-1-one A solution of 1.2 g (3.0 mmol) of 2-[4-(N-benzyl-methylamino)-3-nitro-phenyl]-2-methyl-3-hydroxy-1-pyrrolidin-1-yl-propan-1-one in 20 ml of tetrahydrofuran was mixed with 1.3 ml of (9.3 mmol) of triethylamine at room temperature. Subsequently, 0.27 ml (3.5 mmol) of methanesulfonylchloride were dropped to the reaction mixture at 2–5° C. The formed precipitate was filtered after 2 hours at room temperature and the filtrate evaporated down. The raw product was further processed without purification.

Yield: 1.4 g (98% of theory).

h. 2-[4-(N-benzyl-methylamino)-3-nitro-phenyl]-2-methyl-3-methylamino-1-pyrrolidin-1-yl-propan-1-one A solution of 1.4 g (2.9 mmol) of 2-[4-(N-Benzyl-methylamino)-3-nitro-phenyl]-2-methyl-3-methansulfonyloxy-1-pyrrolidin-1-yl-propan-1-one in 10 ml of dimethylformamide was mixed with 20 ml of a 40 percent aqueous solution of methylamine and heaed up to 100° C. for 70 minutes. After cooling the reaction mixture was mixed with ice water and extracted with ethyl acetate. The organic phase was washed with water and sodium chloride solution, dried over magnesium sulfate and evaporated down. The raw product was purified on silica gel, whereby the eluation was carried out with ethyl acetate/ethanol (10:1, 9:1, 4:1+1% conc. ammonia). The uniform fractions were combined and evaporated down.

Yield: 740 mg (61% of theory), $R_f$ value: 0.45 (silica gel; methylene chloride/ethanol=9:1+0.1% ammonia).

i. 2-[4-(N-benzyl-methylamino)-3-nitro-phenyl]-2-methyl-3-(N-methoxycarbonylmethylcarbonyl-methylamino)-1-pyrrolidin-1-yl-propan-1-one Prepared analogously to Example 7d from 2-[4-(N-benzyl-methylamino)-3-nitro-phenyl]-2-methyl-3-methylamino-1-pyrrolidin-1-yl-propan-1-one and methyl malonate acid chloride.

Yield: 84% of theory, $R_f$ value: 0.65 (silica gel; ethyl acetate/ethanol 9:1+0.1% ammonia); $C_{27}H_{34}N_4O_6$ (510.60); mass spectrum: $(M-H)^-$=509;

$(M+Na)^+$=533.

j. 2-(4-methylamino-3-amino-phenyl)-2-methyl-3-(N-methoxy-carbonylmethylcarbonyl-methylamino)-1-pyrrolidin-1-yl-propan-1-one Prepared analogously to Example 1d from 2-[4-(N-benzyl-methylamino)-3-nitro-phenyl]-2-methyl-3-(N-methoxycarbonylmethylcarbonyl-methylamino)-1-pyrrolidin-1-yl-propan-1-one and hydrogen/palladium on charcoal.

Yield: 100% of theory, $R_f$ value: 0.40 (silica gel; ethyl acetate/ethanol 9:1+0.1% ammonia); $C_{20}H_{30}N_4O_4$ (390.49); mass spectrum: $M^+$=390.

k. 5-{[6-(1-(N-ethoxycarbonylmethylcarbonyl-methylamino)-1-(pyrrolidin-1-yl-carbonyl)-ethyl)-2-oxo-1,2-dihydroquinoxalin-3-yl)-methyl]-benzonitrile Prepared analogously to Example 7f from 2-(4-methylamino-3-amino-phenyl)-2-methyl-3-(N-methoxycarbonylmethylcarbonyl-methylamino)-1-pyrrolidin-1-yl-propan-1-one and 3-(4-cyanophenyl)-oxo-propionic acid in ethanol.

Yield: 23% of theory, $R_f$ value: 0.55 (silica gel; ethyl acetate/ethanol 9:1); $C_{31}H_{39}N_5O_5$ (557.65); mass spectrum: $(M-H)^+$=556;

$(M+Na)^+$=580.

l. 5-{[6-(1-(N-ethoxycarbonylmethylcarbonyl-methylamino)-1-(pyrrolidin-1-yl-carbonyl)-ethyl)-2-oxo-1,2-dihydroquinoxalin-3-yl]-methyl}-benzamidine-hydrochloride Prepared analogously to Example 1f from 5-{[6-(1-(N-ethoxycarbonylmethylcarbonyl-methylamino)-1-(pyrrolidin-1-yl-carbonyl)-ethyl)-2-oxo-1,2-dihydroquinoxalin-3-yl]-methyl}-benzonitrile and hydrochloric acid/ammonium carbonate.

Yield: 35% of theory, $C_{31}H_{38}N_6O_5 \times HCl$ (574.69/611.14); mass spectrum: $(M+H)^+$=575;

$(M-H)^+$=573;

$(M+Na)^+$=609/611.

EXAMPLE 46

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 47

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 48

Tablet Containing 50 mg of Active Substance

Composition:

| | | |
|---|---|---|
| (1) Active substance | 50.0 | mg |
| (2) Lactose | 98.0 | mg |
| (3) Maize starch | 50.0 | mg |
| (4) Polyvinylpyrrolidone | 15.0 | mg |
| (5) Magnesium stearate | 2.0 | mg |
| | 215.0 | mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 49

Tablet Containing 350 mg of Active Substance

Preparation:

| | | |
|---|---|---|
| (1) Active substance | 350.0 | mg |
| (2) Lactose | 136.0 | mg |
| (3) Maize starch | 80.0 | mg |
| (4) Polyvinylpyrrolidone | 30.0 | mg |
| (5) Magnesium stearate | 4.0 | mg |
| | 600.0 | mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 50

Capsules Containing 50 mg of Active Substance

Composition:

| | | |
|---|---|---|
| (1) Active substance | 50.0 | mg |
| (2) Dried maize starch | 58.0 | mg |
| (3) Powdered lactose | 50.0 | mg |
| (4) Magnesium stearate | 2.0 | mg |
| | 160.0 | mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 51

Capsules Containing 350 mg of Active Substance

Composition:

| | | |
|---|---|---|
| (1) Active substance | 350.0 | mg |
| (2) Dried maize starch | 46.0 | mg |
| (3) Powdered lactose | 30.0 | mg |
| (4) Magnesium stearate | 4.0 | mg |
| | 430.0 | mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 52

Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

What is claimed is:

1. A compound of the formula I $$R_a\text{—Het—A—Ar—}R_b \quad (I)$$

wherein

A denotes an oxygen or sulphur atom, a difluoromethylene group, an imino group optionally substituted by a $C_{1-3}$-alkyl group, or a methylene group optionally mono- or disubstituted by a carboxy-$C_{1-3}$-alkyl group, Ar denotes a phenylene group optionally substituted by a fluorine, chlorine or bromine atom, by a trifluoromethyl, $C_{1-3}$-alkyl or $C_{1-3}$-alkoxy group, Het denotes a quinoxazolinylene ring, which may be substituted in the aromatic heterocyclic moiety by a $C_{1-3}$-alkyl, amino, $C_{1-3}$-alkylamino or di-($C_{1-3}$-alkyl) amino group, a quinoxazolinylene ring, which is di- or tetrahydrogenated in the heterocyclic moiety, whilst the dihydrogenated rings, which may additionally be substituted by a $C_{1-3}$-alkyl group, a methylene group adjacent to a nitrogen atom is replaced by a carbonyl or thiocarbonyl group, or in the tetrahydrogenated ring, which may additionally be substituted by one or two $C_{13}$-alkyl groups, two methylene groups adjacent to a nitrogen atom are each replaced by a carbonyl group, and the phenyl moiety of the abovementioned bicyclic rings linked to the group $R_a$, $R_a$ denotes a $C_{1-3}$-alkyl group, which is substituted by a $C_{1-3}$-alkanoylamino or carboxy-$C_{1-3}$-alkylcarbonylamino group, a $R_1$—CO—$CH_2$ group which may be substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, carboxy-$C_{1-3}$-alkylaminocarbonyl or di-($C_{1-3}$-alkyl)-amino-n-$C_{2-4}$-alkyl group and a phenyl group may additionally be fused to the abovementioned pyrrolidino and piperidino moieties via two adjacent carbon atoms, a phenyl, naphthyl or monocyclic 5 or 6 membered heteroaryl group optionally substituted by a $C_{1-3}$-alkyl group, whereby a 6 membered heteroaryl group contains one, two or three nitrogen atoms and a 5 membered heteroaryl group contains an imino group optionally substituted by a $C_{1-3}$-alkyl group, an oxygen or sulphur atom group or an imino group optionally substituted by a $C_{1-3}$-alkyl group and an oxygen or sulphur atom or one or two nitrogen atoms and the before mentioned alkyl substituent may be substituted by a carboxy, carboxy-$C_{1-3}$-alkoxy, carboxy-$C_{1-3}$-alkylamino or N—($C_{1-3}$-alkyl)-carboxy-$C_{1-3}$-alkylamino group, a $C_{1-4}$-alkyl group which is substituted by one or two carboxy groups, a $C_{1-4}$-alkyl group which is substituted
by a $C_{1-3}$-alkyl-$Y_1$—$C_{1-3}$-alkyl, HOOC—$C_{1-3}$-alkyl-$Y_1$-$C_{1-3}$-alkyl, tetrazoly-$C_{1-3}$-alkyl-$Y_2$—, $R_2NR_3$— or $R_2NR_3$—$C_{1-3}$-alkyl group and
by a carboxy, aminocarbonyl, $C_{1-3}$-alkylaminocarbonyl, di-($C_{1-3}$-alkyl)-aminocarbonyl or $C_{5-7}$-cycloalkyleniminocarbonyl group, whereby the $C_{5-7}$-cycloalkylenimino moiety in the before mentioned groups may be substituted by one or two $C_{1-3}$-alkyl groups and at the same time additionally one alkyl moiety or alkyl substituent of the before mentioned $C_{1-3}$-alkylaminocarbonyl, di-($C_{1-3}$-alkyl)-aminocarbonyl or $C_{5-7}$cycloalkyleniminocarbonyl groups may be substituted by a carboxy group, and the remaining hydrogen atoms of a $C_{1-4}$-alkyl group may be totally or partly replaced by fluorine atoms, wherein
$R_2$ denotes a hydrogen atom or a $C_{1-3}$-alkyl group optionally substituted by a carboxy group and
$R_3$ denotes a $C_{1-3}$-alkyl-$Y_1$—$C_{1-3}$-alkyl-$Y_2$, carboxy-$C_{1-3}$-alkyl-$Y_1$—$C_{1-3}$-alkyl-$Y_2$, $C_{1-3}$-alkyl-$Y_2$ or carboxy-$C_{1-3}$-alkyl-$Y_2$ group or
$R_2$ and $R_3$ together with the attached nitrogen atom denotes a $C_{3-7}$-cycloalkylenimino group optionayly substituted by a carboxy, $C_{1-3}$-alkyl or carboxy-$C_{1-3}$-alkyl group, wherein
$Y_1$ denotes a carbon—carbon bond, an oxygen atom, a sulphenyl, sulphinyl, sulphonyl, —NH—, —NH—CO— or —NH—CO—NH— group and
$Y_2$ denotes a carbon-nitrogen bond or a carbonyl, sulphonyl or —NH—CO— group, whereby the carbonyl group of the —NH—CO— group is attached to the nitrogen atom of the $R_2NR_3$ group, and the imino groups mentioned at the definition of the radicals $Y_1$ and $Y_2$ may be additionally substituted by a $C_{1-3}$-alkyl or carboxy-$C_{1-3}$-alkyl group, a hydroxyimino-$C_{1-3}$-alkylene group which may be substituted at the oxygen atom by a carboxy-$C_{1-3}$-alkyl group, a phenyl group which may be substituted by a $C_{1-3}$-alkyl, $C_{2-3}$-alkenyl, carboxy, nitro or amino group, whilst the amino group may additionally be substituted by a $C_{1-3}$-alkanoyl, carboxy-$C_{1-3}$-alkyl, carboxy-$C_{1-3}$-alkylcarbonyl or carboxy-$C_{1-3}$-alkylaminocarbonyl group, a phenyl group which is substituted by a $C_{1-3}$-alkyl group and by a carboxy or carboxy-$C_{1-3}$-alkylaminocarbonyl group, a carbonyl group which is substituted by a $C_{1-6}$-alkyl, $C_{5-7}$-cycloalkyl, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl or tetrazolyl-$C_{1-3}$-alkyl group, a carboxy-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, carboxy-$C_{1-3}$-alkylsulphonyl, tetrazolyl-$C_{1-3}$-alkylcarbonyl or carboxy-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl group, which may additionally be substituted by a $C_{1-5}$-alkyl group, a phenylsulphonyl group or a $C_{1-5}$-alkylsulphonyl group wherein the alkyl moiety may be substituted by an amino, $C_{1-3}$-alkylamino or di-($C_{1-3}$-alkyl)-amino group, an imidazolidin-2-on-1-yl group which may be substituted in the 3 position by a carboxy-$C_{1-3}$-alkyl group, a $C_{3-7}$-cycloalkyl group which is substituted in the 1 position by a $C_{4-7}$-cycloalkylamino or $C_{1-4}$-alkylamino group, wherein the hydrogen atom of the amino moiety may be replaced by a carboxy-$C_{1-3}$-alkylcarbonyl group, and $R_b$ denotes a cyano group or an amidino group, whereby the carboxy groups mentioned above at the definition of the radicals may be replaced by a group convertable in-vivo into a carboxy group or by a group convertable under physiologically conditions into a negatively charged group or the amino or imino groups groups mentioned above at the definition of the radicals may be substituted by a group which can be splitt off in-vivo, or a tautomer or salt thereof.

2. A compound of the formula I, as claimed in claim 1, wherein

A denotes an oxygen or sulphur atom, a difluoromethylene group, an imino group optionally substituted by a $C_{1-3}$-alkyl group, or a methylene group optionally mono- or disubstituted by a carboxy-$C_{1-3}$-alkyl or $C_{1-3}$-alkoxycarbonyl-$C_{1-3}$-alkyl group, Ar denotes a phenylene group optionally substituted by a fluorine, chlorine or bromine atom, by a trifluoromethyl, $C_{1-3}$-alkyl or $C_{1-3}$-alkoxy group, Het denotes a quinoxazolinylene ring, which may be substituted in the aromatic heterocyclic moiety by a $C_{1-3}$-alkyl, amino, $C_{1-3}$-alkylamino or di-($C_{1-3}$-alkyl) amino group, a quinoxazolinylene ring, which is di- or tetrahydrogenated in the heterocyclic moiety, whilst the dihydrogenated ring, which may additionally be substituted by a $C_{1-3}$-alkyl group, a methylene group adjacent to a nitrogen atom is replaced by a carbonyl or thiocarbonyl group, or in the tetrahydrogenated ring, which may additionally be substituted by one or two $C_{1-3}$-alkyl groups, two methylene groups adjacent to a nitrogen atom are each replaced by a carbonyl group, and the phenyl moiety of the abovementioned bicyclic rings is linked to the group $R_a$, $R_a$ denotes a $C_{1-3}$-alkyl group, which is substituted by a $C_{1-3}$-alkanoylamino, carboxy-$C_{1-3}$-alkylcarbonylamino or $C_{1-3}$-alkoxycarbonyl-$C_{1-3}$-alkylcarbonylamino group, a $C_{1-4}$-alkyl group which is substituted by one or two carboxy or $C_{1-3}$-alkoxycarbonyl groups or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylcarbonyl, $C_{1-3}$-alkoxycarbonyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a phenylsulphonyl group or a $C_{1-5}$-alkylsulphonyl group wherein the alkyl moiety may be substituted by an amino, $C_{1-3}$-alkylamino or di-($C_{1-3}$-alkyl)-amino group, an imidazolidin-2-on-1-yl group which may be substituted in the 3 position by a carboxy-$C_{1-3}$-alkyl or $C_{1-3}$-alkoxycarbonyl-$C_{1-3}$-alkyl group, a $C_{3-7}$-cycloalkyl group which is substituted in the 1 position by a $C_{4-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, a $R_1$—CO—CH$_2$ group which may be substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl, $C_{1-3}$-alkoxycarbonyl-$C_{1-3}$-alkylaminocarbonyl or di-($C_{1-3}$-alkyl)-amino-n-$C_{2-4}$-alkyl group and a phenyl group may additionally be fused to the abovementioned pyrrolidino and piperidino moieties via two adjacent carbon atoms, or a pyrazolyl group optionally substituted by a $C_{1-3}$-alkyl group, and $R_b$ denotes a cyano group or an amidino group optionally substituted by a hydroxy, by one or two $C_{1-3}$-alkyl groups or by a $C_{1-16}$-alkoxycarbonyl group, or a tautomer or salt thereof.

3. A compound of the formula I, in accordance with claim 1, wherein

Het denotes a 2-oxo-1,2-dihydro-quinoxalin-3-yl or 2-thio-1,2-dihydro-quinoxalin-3-yl, or a tautomer or salt thereof.

4. A compound of the formula I, in accordance with claim 1, wherein

A denotes an oxygen atom, a methylene or imino group,

Ar denotes a phenylene group optionally substituted by a fluorine, chlorine or bromine atom, by a trifluoromethyl, $C_{1-3}$-alkyl or $C_{1-3}$-alkoxy group, Het denotes a 1-($C_{1-3}$-alkyl)-2-oxo-1,2-dihydro-quinazolin-3-yl or 1-($C_{1-3}$-alkyl)-2-thio-1,2-dihydro-quinazolin-3-yl-group each attached via the phenyl moiety with the radical $R_a$, $R_a$ denotes a $C_{1-3}$-alkyl group, which is substituted by a $C_{1-3}$-alkanoylamino, carboxy-$C_{1-3}$-alkylcarbonylamino or $C_{1-3}$-alkoxycarbonyl-$C_{1-3}$-alkylcarbonylamino group, a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-alkylcarbonyl, $C_{1-3}$-alkoxycarbonyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl, amino-$C_{1-3}$-alkyl, $C_{1-3}$-alkylamino-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a piperidino group, wherein a methylene group in the 2 position is replaced by a carbonyl or sulphonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a phenylsulphonyl group or a $C_{1-5}$-alkylsulphonyl group wherein the alkyl moiety may be substituted by a di-($C_{1-3}$-alkyl)-amino group, an imidazolidin-2-on-1-yl group which may be substituted in the 3 position by a carboxy-$C_{1-3}$-alkyl or $C_{1-3}$-alkoxycarbonyl-$C_{1-3}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, a $R_1$—CO—$CH_2$ group which is substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, morpholino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fused to the abovementioned pyrrolidino and piperidino moieties via two adjacent carbon atoms, or a pyrazolyl group optionally substituted by a $C_{1-3}$-alkyl group, and $R_b$ denotes a cyano group or an amidino group optionally substituted by a hydroxy, $C_{1-16}$-alkoxycarbonyl or 17-(1,5-dimethyl-hexyl)-10,13-dimethyl-2,3,4,7,8,9,10,11,12,13,14,15,16,17-tetradecahydro-1H-cyclopenta[a]phe-nanthren-3-yl]-oxycarbonyl group, or a tautomer or salt thereof.

5. A compound of the formula I, in accordance with claim 1, wherein

A denotes an oxygen atom, a methylene or imino group,

Ar denotes a phenylene group,

Het denotes a 1-($C_{1-3}$-alkyl)-2-oxo-1,2-dihydro-quinazolin-3-yl group attached via the phenyl moiety with the radical $R_a$, $R_a$ denotes a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two $C_{1-3}$-alkyl groups, a $R_1$—CO—$CH_2$ group which is substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino, piperazino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fused to the abovementioned pyrrolidino and piperidino moieties via two adjacent carbon atoms, or a pyrazolyl group optionally substituted by a $C_{1-3}$-alkyl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl, nitro or amino group, whilst the amino group may additionally be substituted by a $C_{1-3}$-alkanoyl, carboxy-$C_{1-3}$-alkyl, $C_{1-3}$-alkoxycarbonyl-$C_{1-3}$-alkyl, carboxy-$C_{1-3}$-aklylaminocarbonyl or $C_{1-3}$-alkoxycarbonyl-$C_{1-3}$-alkylaminocarbonyl group, a phenyl group which is substituted by a $C_{1-3}$-alkyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, and $R_b$ denotes an amidino group optionally substituted by a hydroxy, $C_{1-16}$-alkoxycarbonyl or 17-(1,5-dimethyl-hexyl)-10,13-dimethyl-2,3,4,7,8,9,10,11,12,13,14,15,16,17-tetradecahydro-1H-cyclopenta[a]phenanthren-3-yl]-oxycarbonyl group, or a tautomer or salt thereof.

6. A compound of the formula I, in accordance with claim 1, wherein

A denotes an oxygen atom, a methylene or imino group,

Ar denotes a 1,4-phenylene group,

Het denotes a 1-methyl-2-oxo-1,2-dihydro-quinazolin-3-yl group attached via the phenyl moiety with the radical $R_a$, $R_a$ denotes a $C_{1-4}$-alkyl group which is substituted by a carboxy or $C_{1-3}$-alkoxycarbonyl group or by a pyrrolidinocarbonyl or piperidinocarbonyl group and by a carboxy, $C_{1-3}$-alkoxycarbonyl, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whereby the before mentioned pyrrolidino and piperidino moieties may be additionally substituted by one or two methyl groups, a $R_1$—CO—$CH_2$ group which is substituted in the methylene moiety by one or two $C_{1-3}$-alkyl groups, or a $C_{3-6}$-cycloalkylene group which is substituted in the 1 position by an $R_1$—CO group, whilst $R_1$ is a hydroxy, $C_{1-3}$-alkoxy, amino, $C_{1-3}$-alkylamino, pyrrolidino, piperidino or N—($C_{1-3}$-alkyl)-piperazino group, whilst the abovementioned amino, $C_{1-3}$-alkylamino, pyrrolidino and piperidino groups may additionally be substituted by a $C_{1-3}$-alkyl, carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group and a phenyl group may additionally be fuised to the abovementioned pyrrolidino and piperidino moieties via two adjacent carbon atoms, or a 1-($C_{1-3}$-alkyl)-pyrazol-5-yl group, a hydroxyimino-$C_{1-3}$-alkylene group which may be substituted at the oxygen atom by a carboxy-$C_{1-3}$-alkyl or $C_{1-3}$-alkoxycarbonyl-$C_{1-3}$-alkyl group, a phenyl group which may be substituted by a $C_{1-3}$-alkyl, $C_{2-3}$-alkenyl, carboxy, $C_{1-3}$-alkoxycarbonyl or amino group, whilst the amino group may additionally be substituted by a carboxy-$C_{1-3}$-alkyl, $C_{1-3}$-alkoxycarbonyl-$C_{1-3}$-alkyl, carboxy-$C_{1-3}$-alkylaminocarbonyl or $C_{1-3}$-alkoxycarbonyl-$C_{1-3}$-alkylaminocarbonyl group, a phenyl group which is substituted by a methyl group and by a carboxy, $C_{1-3}$-alkoxycarbonyl, carboxy-$C_{1-3}$-alkylaminocarbonyl or $C_{1-3}$-alkoxycarbonyl-$C_{1-3}$-alkylaminocarbonyl group, a carbonyl group which is substituted by a $C_{1-6}$-alkyl, $C_{5-7}$-cycloalkyl group, $C_{1-6}$-alkylamino, phenylamino or pyridylamino group, whilst in the abovementioned groups the cycloalkyl moiety may additionally be substituted by a $C_{1-3}$-alkyl group and the hydrogen atom of the abovementioned amino groups is replaced by a carboxy-$C_{1-3}$-alkyl, $C_{1-3}$-alkoxycarbonyl-$C_{1-3}$-alkyl or tetrazolyl-$C_{1-3}$-alkyl group, a carboxy-$C_{1-3}$-alkylsulphonamido, $C_{1-3}$-alkoxycarbonyl-$C_{1-3}$-alkylsulphonamido, phenylsulphonylamido, naphthylsulphonylamido, quinolinesulphonamido or isoquinolinesulphonamido group, wherein the hydrogen atom of the amido moiety may be substituted by a carboxy-$C_{1-3}$-alkyl, $C_{1-3}$-alkoxycarbonyl-$C_{1-3}$-alkyl or di-($C_{1-3}$-alkyl)-amino-$C_{1-3}$-alkyl group, a $C_{1-6}$-alkylamino or $C_{3-7}$-cycloalkylamino group, wherein the hydrogen atom of the amino group is replaced by a carboxy-$C_{1-3}$-alkylcarbonyl, $C_{1-3}$-alkoxycarbonyl-$C_{1-3}$-alkylcarbonyl, carboxy-$C_{1-3}$-alkylsulphonyl, $C_{1-3}$-alkoxycarbonyl-$C_{1-3}$-alkylsulphonyl, tetrazolyl-$C_{1-3}$-alkylcarbonyl, carboxy-$C_{1-3}$-alkylaminocarbonyl or $C_{1-3}$-alkoxycarbonyl-$C_{1-3}$-alkylaminocarbonyl group, a tetrazolyl group optionally substituted by a $C_{1-5}$-alkyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{3-7}$-cycloalkyl group which is substituted in the 1 position by a $C_{5-7}$-cycloalkylamino or $C_{1-4}$-alkylamino group, wherein the hydrogen atom of the amino moiety may be replaced by a carboxy-$C_{1-3}$-alkylcarbonyl or $C_{1-3}$-alkoxycarbonyl-$C_{1-3}$-alkylcarbonyl group, and $R_b$ denotes an amidino group optionally substituted by a hydroxy, $C_{1-16}$-alkoxycarbonyl or 17-(1,5- dimethyl-hexyl)-10,13-dimethyl-2, 3, 4, 7, 8, 9, 10, 11, 12, 13, 14, 15, 16, 17-tetradecahydro-1H-cyclopenta[a]phe-nanthren-3-yl]-oxycarbonyl group, or a tautomer or salt thereof.

7. A compound selected from the group consisting of:
 (a) 4-{[6-(N-carboxymethyl-quinolin-8-yl-sulphonylamino)-1-methyl-2-oxo-1,2-dihydroquinoxalin-3-yl]-methyl}-benzamidine,
 (b) 4-{[6-(1-(N-cyclopentyl-carboxymethylcarbonylamino)-cyclo-propyl)-1-methyl-2-oxo-1,2-dihydroquinoxalin-3-yl]-methyl}-benzamidine,
 (c) 4-{[6-(1-methyl-1-(pyrrolidin-1-yl-carbonyl)-ethyl)-1-methyl-2-oxo-1,2-dihydroquinoxalin-3-yl]-methyl}-benzamidine,
 (d) 4-{[6-(1-(pyrrolidin-1-yl-carbonyl)-cyclopropyl)-1-methyl-2-oxo-1,2-dihydroquinoxalin-3-yl]-methyl}-benzamidine,
 (e) 4-{[6-(1-(N-methyl-carboxymethylcarbonylaminomethyl)-1-(pyrrolidin-1-yl-carbonyl)-ethyl)-1-methyl-2-oxo-1,2-dihydroquinoxalin-3-yl]-methyl}-benzamidine or a salt thereof.

8. A physiologically acceptable salt of a compound of the formula I, in accordance with claim 1, wherein $R_b$ denotes an amidino mentioned in claim 1.

9. 4-{[6-(1-(pyrrolidin-1-yl-carbonyl)-cyclopropyl)-1-methyl-2-oxo-1,2-dihydroquinoxalin-3-yl]-methyl}-benzamidine or a salt thereof.

10. A pharmaceutical composition containing a compound in accordance with claim 1, 2, 3, 4, 5, 6, 7 or 9, wherein $R_b$ denotes one of the amidino groups mentioned in claim 1, 2, 3, 4, 5, 6, 7 or 9, or a salt thereof in accordance with claim 8.

11. A method for inhibiting thrombus formation in a host in need of such treatment which comprises administering to said host an antithrombotic amount of a compound in accordance with claim 1, 2, 3, 4, 5, 6, 7 or 9, wherein $R_b$ denotes one of the amidino groups mentioned in claim 1, 2, 3, 4, 5, 6, 7 or 9, or a salt according to claim 8.

* * * * *